United States Patent
Belaid-Sandal et al.

(10) Patent No.: US 11,965,028 B1
(45) Date of Patent: Apr. 23, 2024

(54) NEUROPILIN-1-PEPTIDE BASED ANTIBODY, HIGHLIGHTING NEW EPITOPE ASSOCIATED TO GLYCOSAMINOGLYCAN-MODIFIED NEUROPILIN-1 AND METHODS OF USE THEREOF

(71) Applicant: Theranovir, Evry Courcouronees (FR)

(72) Inventors: Zakia Belaid-Sandal, Paris (FR); Elie Matta, Fresnes (FR); Flavien Berthou, Palaiseau (FR)

(73) Assignee: Theranovir, Evry Courcouronees (FR)

( * ) Notice: Subject to any disclaimer, the term of this patent is extended or adjusted under 35 U.S.C. 154(b) by 0 days.

(21) Appl. No.: 18/340,774

(22) Filed: Jun. 23, 2023

(30) Foreign Application Priority Data

Jan. 19, 2023 (EP) .................................... 23152550

(51) Int. Cl.
*A61P 35/00* (2006.01)
*C07K 16/28* (2006.01)

(52) U.S. Cl.
CPC .......... *C07K 16/2857* (2013.01); *A61P 35/00* (2018.01); *C07K 2317/565* (2013.01); *C07K 2317/77* (2013.01)

(58) Field of Classification Search
CPC .................................................. C07K 16/2857
USPC ...................................................... 424/133.1
See application file for complete search history.

(56) References Cited

FOREIGN PATENT DOCUMENTS

| WO | 2015/124588 A1 | 8/2015 |
| WO | 2017/050793 A1 | 3/2017 |
| WO | 2018/119171 A1 | 6/2018 |

OTHER PUBLICATIONS

Ahrens et al., The Role of Proteoglycans in Cancer Metastasis and Circulating Tumor Cell Analysis, Frontiers in Cell and Developmental Biology, vol. 8, (Aug. 2020), 27 pages.
Alix Panabieres et al, Molecular Portrait of Metastasis-Competent Circulating Tumor Cells in Colon Cancer Reveals the Crucial Role of Genes Regulating Energy Metabolism and DNA Repair, Clinical Chemistry, (2017), vol. 63, No. 3, pp. 700-713.
Bankhead et al., QuPath: Open Source Software for Digital Pathology Image Analysis, Scientific Reports, (2017), vol. 7, 7 pages.
Belaid-Choucair et al., Human Bone Marrow Adipocytes Block Granlopoiesis Through Neuropilin-1-Induced Granulocyte Colony-Stimulating Factor Inhibitition, Stem Cells, (2008), vol. 26, pp. 1556-1564.
Boxus et al., Hot the DNA Damage Response Determines the Fate of HTLV-1 Tax-Expressing Cells, Retrovirology, (2012), vol. 5, No. 9, 5 pages.
Cackowski et al., Identification of Two Novel Alternatively Spliced Neuropilin-1 Isoforms, Genomics, (2004), vol. 84, No. 82, 21 pages.
Cantuti-Castelvetrie et al., Neuropilin-1 Facilitates SARS-CoV-2 Cell Entry and Infectifity, Science., (2020), vol. 370, pp. 856-860.
Cayrefourcq et al., Establishment and Characterization of a Cell Line from Human Circulating Colon Cancer Cells, Cancer Res., (2015), vol. 75, pp. 892-901.
Cayrefourcq et al., Selective Treatment Pressure in Colon Cancer Drives the Molecular Profile of Resistant Circulating Tumor Cell Clones, Mol Cancer, (2021), vol. 20, 6 pages.
Chabanon et al., Targeting the DNA Damage Response in Immuno-Oncoloty: Developments and Opportunities, Nat Rev Cancer., (2021), vol. 21, pp. 701-717.
Chatterjee et al., Mechanisms of DNA Damage, Repair and Mutagenesis, Environ Mol Mutagen. 2017, vol. 58, No. 5, pp. 235-263.
Chaudhary et al., Neuropilin 1: Function and Therapeutic Potential in Cancer, Cancer Immunol Immunother., (2014), vol. 63, pp. 81-99.
Chen et al., Proteoglycans and Glycosaminoglycans in Stem Cell Homeostasis and Bone Tissue Regeneration, Front Cell Dev Biol., (2021), vol. 30, No. 9, 19 pages.
Chuckran et al., ., Neuropilin-1: A Checkpoint Target with Unique Implications for Cancer Immunology and Immunotherapy, J Immunother Cancer, (2020), vol. 8, 12 pages.
De Candia et al., The Pleiotropic Roles of Leptin in Metabolism, Immunity, and Cancer, J Exp Med., (2021), vol. 218, 17 pages.
Delgoffe et al., Stability and Function of Regulatory T Cells is Maintained by a Neuropilin-1-Semapohorin-4a Axis, Nature, (2013), vol. 501, pp. 252-256.
Dumond et al., Neuropilins, as Relevant Oncology Target: Their Role in the Tumoral Microenvironment, Front Cell Dev Biol., (2020), vol. 8, 10 pages.
Frankel et al., Chondroitin Sulphate-Modified Neuropilin 1 is Expressed in Human Tumour Cells and Modulates 3D Invasion in the U87MG Human Glioblastoma Cell Line through a p130Cas-Mediated Pathway, EMBO Rep., (2008), vol. 9, pp. 983-989.
Fucikova et al., Detection of Immunogenic Cell Death and its Relevance for Cancer Therapy, Cell Death Dis., (2020), vol. 11, No. 11, 13 pages.
Gagnon et al., Identification of a Natural Soluble Neuropilin-1 that Binds Vascular Endothelial Growth Factor: In Vivo Expression and Antitumor Activity, Proc Natl Acad Sci USA, (2000), vol. 97, pp. 2573-2578.

(Continued)

*Primary Examiner* — Sean E Aeder
(74) *Attorney, Agent, or Firm* — TraskBritt

(57) ABSTRACT

Disclosed are NRP-1 peptides vaccines corresponding to epitopes associated to diseases and capable of triggering the immune response such as production of anti-NRP-1 antibodies with specificity to GAG-modified NRP-1 that are able to block DNA damages response (DDR). In particular, NRP-1 peptides vaccines and their derived anti-NRP-1 antibodies (NRP-1 peptides antibodies) specific for an epitope located in the binding domain of leptin on NRP-1 that are able to enter into the nucleus and to block DNA damages response (DDR) and having properties of interest in the treatment of diseases involving NRP-1/OBR complex. The NRP-1 peptide vaccines and the NRP-1 peptides antibodies are of interest in therapies; especially in diseases related to DNA damage response and Glycosaminoglycans.

15 Claims, 18 Drawing Sheets
Specification includes a Sequence Listing.

(56) References Cited

OTHER PUBLICATIONS

Galluzzi et al., Consensus Guidelines for the Definition, Detection and Interpretation of Immunogenic Cell Death, J Immunother Cancer, (2020), vol. 8, No. 1, 22 pages.

Geretti et al., Neuropilin Structure Governs VEGF and Semaphorin Binding Regulates Angiogenesis, Angiogenesis, (2008), 1vol. 1, pp. 31-39.

Ghez et al., Early-Onset Invasive Aspergillosis and Other Fungal Infections in Patients Treated with Ibrutinib, J Virol., (2006), vol. 80, pp. 6844-6854.

Giglia-Mari et al., DNA Damage Response, ., Cold Spring Harb Perspect Biol., (2011), vol. 3, No. 1, 21 pages.

Gu et al., Characterization of Neuropilin-1 Structural Features that Confer Binding to Semaphorin 3A and Vascular Endothelial Growth Factor 165*, J Biol Chem., (2002), vol. 277, pp. 18069-18076.

Gudowska-Sawczuk et al., the Role of Neuropilin-1 (NRP-1) in SARS-CoV-2 Infection: Review, J Clin Med., (2021), vol. 10, 8 pages.

He et al., Neuropilin is a Receptor for the Axonal Chemorepellent Semaphorin III, Cell, (Aug. 22, 1997), vol. 90, pp. 739-751.

Hendricks et al., A Novel Physiological Glycosaminoglycan-Deficient Splice Variant of Neuropilin-1 is Anti-Tumorigenic In Vitro and In Vivo, PLoS One, (2016), vol. 11, No. 10, 13 pages.

Hörmann et al., Vascular Endothelial Growth Factor Confers Endothelial Resistance to Apoptosis through Poly(ADP-ribose) Polymerase, Journal of Thrombosis and Haemostasis, (2010), vol. 9, pp. 1391-1403, 13 pages.

Huang et al., N-Glycosylation-Defective Splice Variants of Neuropilin-1 Promote Metastasis by Activating Endosomal Signals, Nat Commun., (2019), vol. 10, No. 1, 16 pages.

Jinno et al., Role of Glycosaminoglycans in Infectious Disease, Methods Mol Biol., (2015), pp. 567-585.

Jones et al., Molecular Aspects of HTLV-1 Entry: Functional Domains of the HTLV-1 Surface Subunit (SU) and Their Relationships to the Entry Receptors, Viruses, (2011), vol. 3, No. 6, pp. 794-810.

Juan et al., The Chemistry of Reactive Oxygen Species (ROS) Revisited: Outlining Their Role in Biological Macromolecules (DNA, Lipids and Proteins) and Induced Pathologies, International Journal of Molecular Sciences, Int. J. Mol. Sci. (2021), vol. 22, 21 pages.

Kaddour et al., Transmission of Induced Chromosomal Aberrations through Successive Mitotic Divisons in Human Lymphocytes after In Vitro and In Vivo Radiation, Scientific REorts, (2017), vol. 7, 9 pages.

Kamhi et al., Glycosaminoglycans in Infectious Disease, Biol Rev Camb Philos Soc. (2013), vol. 88, No. 4, pp. 928-943.

Kay et al., Inflammation-Induced DNA Damage, Mutations and Cancer, DNA Repair (Amst)., (2019), vol. 83, 7 pages.

Kitsukawa et al., Overexpression of a Membrane Protein, Neuropilin, In Chimeric Mice Causes Anomalies in the Cardiovascular System, Nervous System and Limbs, Development, vol. 121, pp. 4309-4318.

Lepelletier et al., Control of Human Thymocyte Migration by Neuropilin-1/Semaphorin-3A-Mediated Interactions, Proc Natl Acad Sci U S A., (2007), vol. 104, pp. 5545-5550.

Lepelletier et al., Immunosuppressive Role of Semaphorin-3A on T Cell Profliferation is Mediated by Inhibition of Actin Cytoskeleton Reorganization, Eur J Immunol., (2006), vol. 36, pp. 1782-1793.

Liang et al., Function Blocking Antibodies to Neuropilin-1 Generated from a Designed Human Synthetic Antibody Phage Library, J Mol Biol, (2007), vol. 366, pp. 815-829.

Liu et al., Targeting Neuropilin-1 Interactions is a Promising Anti-Tumor Strategy, Chinese Medical Journal, (2020), vol. 134, pp. 508-517.

Lu et al., Development of Therapeutic Antibodies for the Treatment of Diseases, J Biomed Sci., (2020), vol. 27, No. 1, 30 pages.

Martin et al., DNA Damage and Repair: Relevance to Mechanisms of Neurodegeneration, J Neuropathol Exp Neurol., (2008), vol. 67, No. 5, pp. 377-387.

Meier et al., Parallel Accumulation-Serial Fragmentation (PASEF): Multiplying Sequencing Speed and Sensitivity by Synchronized Scans in a Trapped Ion Mobility Device, J. Proteome Res. (2015), vol. 14, vol. 12, pp. 5378-5387.

Mey et al., Neuropilin-1 Modulates Vascular Endothelial Growth Factor-Induced Poly(ADP-Ribose)-Polymerase Leading to Reduced Cerebrovascular Apoptosis, Neurobiol Dis., (2013), vol. 59 pp. 111-125.

Mishra et al., Leptin Signals via TGFB1 to Promote Metastatic Potential and Stemness in Breast Cance, PLoS One, (2017), vol. 12, 21 pages.

Morla et al., Glycosaminoglycans and Glycosaminoglycan Mimetics in Cancer and Inflammation, Int J Mol Sci., (2019), vol. 20, No. 8, 19 pages.

Palet et al., Germline Humanization of a Non-Human Primate Antibody that Neutralizes the Anthrax Toxin, by in Vitro and in Silico Engineering, Journal of Molecular Biology, (Dec. 2008), vol. 384, No. 5, pp. 1400-1407.
Poplawski et al., DNA Damage Response as a Pharmacological Target for Cancer and Infectious Diseases, Curr Med Chem., (2019), vol. 26, pp. 1423-1422.
Prahst et al., Neuropilin-1-VEGFR-2 Complexing Requires the PDZ-Binding Domain of Neuropilin-1, J Biol Chem, (2008) , vol. 283, pp. 25110-25114.
Ren et al., Letpin Upregulates Telomerase Activity and Transcription of Human Telmerase Reverse Transcriptase in MCF-7 Breast Cancer Cells, Biochem Biophys Res Commun., (2010), vol. 394, No. 1, pp. 59-63.
Rossignol et al., Genomic organization of human neuropilin-1 and neuropilin-2 genes: identification and distribution of splice variants and soluble isoforms, Genomics., (2000), vol. 70, pp. 211-222.
Rossignol et al., Neuropilin-1 Cooperates with PD-1 in CD8+ Cells Predicting Outcomes in Melanoma Patients Treated with Anti-PD1, iScience., (2022), vol. 25, No. 6, 18 pages.
Ryan et al., Activation of the NCA Damage Response by RNA Viruses, Biomolecules, (2016), vol. 6, No. 1, 24 pages.
Shintani et al., Glycosaminoglycan Modification of Neuropilin-1 Modulates BEGFR2 Signaling, EMBO J., (2006), vol. 25, pp. 3045-3055.
Shumaker et al., Effect of Lenvatinib (E7080) on the QTc interval: Results from a Thorough QT Study in Healthy Volunteers, Pharmacol., (2014), vol. 73, pp. 1109-1117.
Soker et al., Neuropilin-1 is Expressed by Endothelial and Tumor Cells as an Isoform-Specific Receptor for Vascular Endothelial Growth Factor, ., Cell., (1998), vol. 92, pp. 735-745.
Soler et al., Autologous Cell Lines From Circulating Colon Cancer Cells Captured from Sequential Liquid Biopsies as Model to Study Therapy-Driven Tumor Changes, Sci Rep., (2018), vol. 8, 12 pages.
Song et al., Glycosaminoglycans, Adv Exp Med Biol., (2021), vol. 1325, pp. 103-116.
Stefanou et al., Leptin as a Critical Regulator of Hepatocellular Carcinoma Development through Modulation of Human Telomerase reverse Transcriptase, BMC Cancer, (2010), vol. 10, 10 pages.
Takakura, Nobuyuki, Formation and Regulation of the Cancer Stem Cell Niche, Cancer Sci., (2012), vol. 103, pp. 1177-1181.
Tang et al., Neuropilin-1 is Over-Expressed in Claudin-Low Breast Cancer and Promotes Tumor Progression Through Acquisition of Stem Cell Characteristics and RAS/MAPK Pathway Activation, Breast Cancer Res., (2022), vol. 24, 17 pages.
Tao et al., Characterization of a New Alternatively Spliced Neuropilin-1 Isoform, Angiogenesis, (2003), vol. 6, pp. 39-45.
Tay et al., Revisiting the Role of CD4+ T Cells in Cancer Immunotherapy—New Insights into old paradigms, Cancer Gene Therapy, (2021, vol. 28, pp. 5-17.).
Tayoun et al., Targeting Genome Integrity Dysfunctions Impedes Metastatic Potency in Non-Small Cell Lung Cancer Circulating Tumor Cell-Derived Explants, T et al., JCI Insight, (2022), vol. 7, 21 pages.
Tordjman et al., A Neuronal Receptor, Neuropilin-1, is Essential for the Initiation of the Primary Immune Response, Nat Immunol., (2002), vol. 3, pp. 477-482.

(56) References Cited

OTHER PUBLICATIONS

Tordjman et al., Neuropilin-1 is Expressed on Bone Marrow Stromal Cells: A Novel Interaction with Hematopoietic Cells?, ., Blood, (1999), vol. 94, pp. 2301-2309.

Trier et al., Peptides, Antibodies, Peptide Antibodies and More, Int J Mol Sci., (2019), vol. 20, 22 pages.

Tubbs et al., Endogenous DNA Damage as a Source of Genomic Instability in Cancer, Cell, (2017), vol. 168, No. 4, pp. 644-656.

Van Den Boogaard et al., Chemotherapy Side-Effects: Not All DNA Damage is Equal, Cancers, (2022), vol. 14, No. 3, 27 pages.

Vescarelli et al., MIR-200c Sensitizes Oaparib-Resistant Ovarian Cancer Cells by Targeting Neuropilin 1, J Exp Clin Cancer Res., (2020), vol. 39, 15 pages.

Vitale et al., Proteoglycans and Glycosaminoglycans as Regulators of Cancer Stem Cell Function and Therapeutic Resistance, FEBS, (2019), vol. 286, pp. 2870-2882.

Wang et al., Neuropilin 1 is an entry Factor that Promotes EBV Infection of Nasopharyngeal Epithelial Cells, Nat Commun., (2015), vol. 6, 29 pages.

Weekes et al., A Phase I Study of the Human Monoclonal Anti-NRP1 Antibody MNRP1685A in Patients with Advanced Solid Tumors, Invest New Drugs, (2014), vol. 32, pp. 653-660.

Wilson et al., Neuropilin-1 Expression in Adipose Tissue Macrophages Protects Against Obesity and Metabolic Syndrome, Sci Immunol., (2018), vol. 3, 20 pages.

Windwarder et al., Detailed Characterization of the O-Linked Glycosylation of the Neuropilin-1 c/MAM-Domain, Glycoconjugate Journal, (2016), vol. 33, pp. 387-397.

Wood et al., Mutation Research/Fundamental and Molecular Mechanisms of Mutagenesis, Mutat Res., (2005), vol. 577, Nos. 1-2, pp. 275-283.

Wu et al., Glycosylation-Dependent Galextin-1/Neuropilin-1 Interactions Promote Liver Fibrosis through Activation of TGF-ß-and PDGF-like Signals in Hepatic Stellate Cells, Sci. Rep., (2017), vol. 7, 26 pages.

Xin et al., pharmacokinetic and Pharmacodynamic Analysis of Circulating Biomarkers of Anti-NRP1, a Novel Antiangiogenesis Agent, in Two Phase 1 Trials in Patients with Advanced Solid Tumors, Clin Cancer Res., (2012), vol. 18, pp. 6040-6048.

Yano et al., Intratumoral Regulatory T Cells: Markers, Subsets and Their Impact on Anti-Tumor Immunity, Immunology, (2019), vol. 157, pp. 232-247.

Zacchi et al., A Novel High-Throughput Yeast Genetic Screen for Factors Modifying Protein Levels of the Early-Onset Torsion Dystonia-Associated Variant TorsinA?E, Glycoconj J., (2016), vol. 33, pp. 359-376.

Zhang et al., Peptide-Based Materials for Cancer Immunotherapy, Theranostics, (2019), vol. 9, No. 25, pp. 7807-7825.

Zheng et al., Leptin Receptor Maintains Cancer Stem-Like Properties in Triple Negative Breast Cancer Cells, Endocr Relat Cancer, (2013), vol. 20, pp. 797-808.

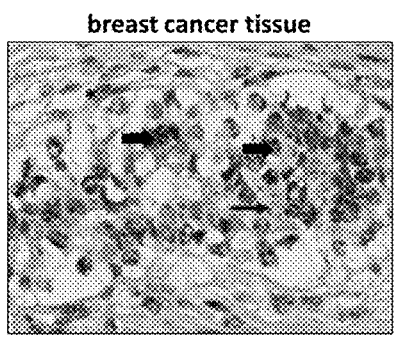
FIG. 1A breast cancer tissue
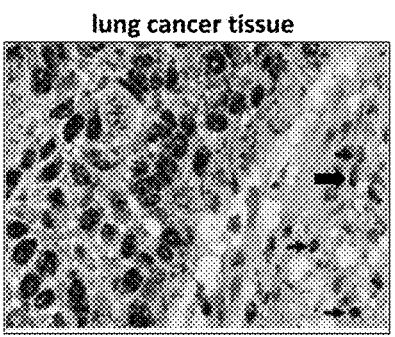
FIG. 1B lung cancer tissue
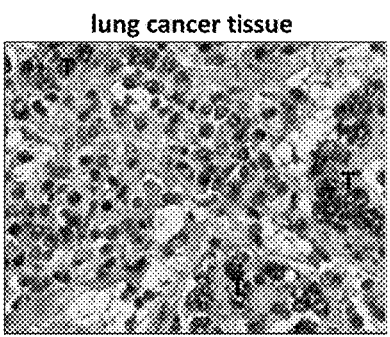
FIG. 1C lung cancer tissue
FIG. 1D colon cancer tissue
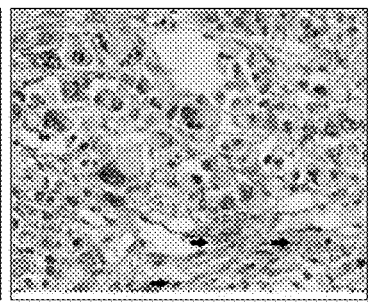
FIG. 1E metastatic colon cancer tissue

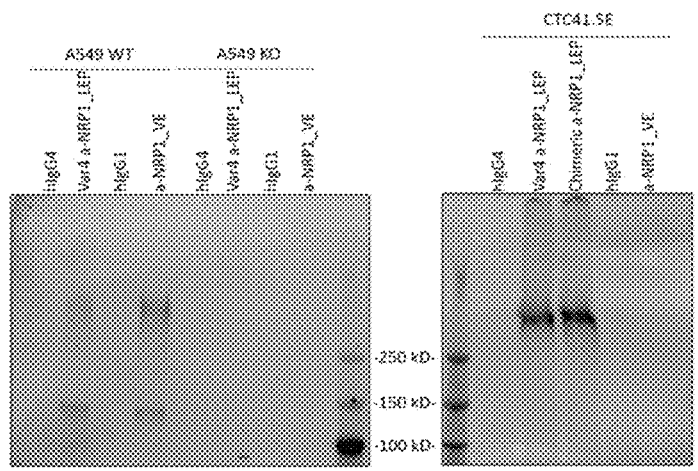
*FIG. 4A*
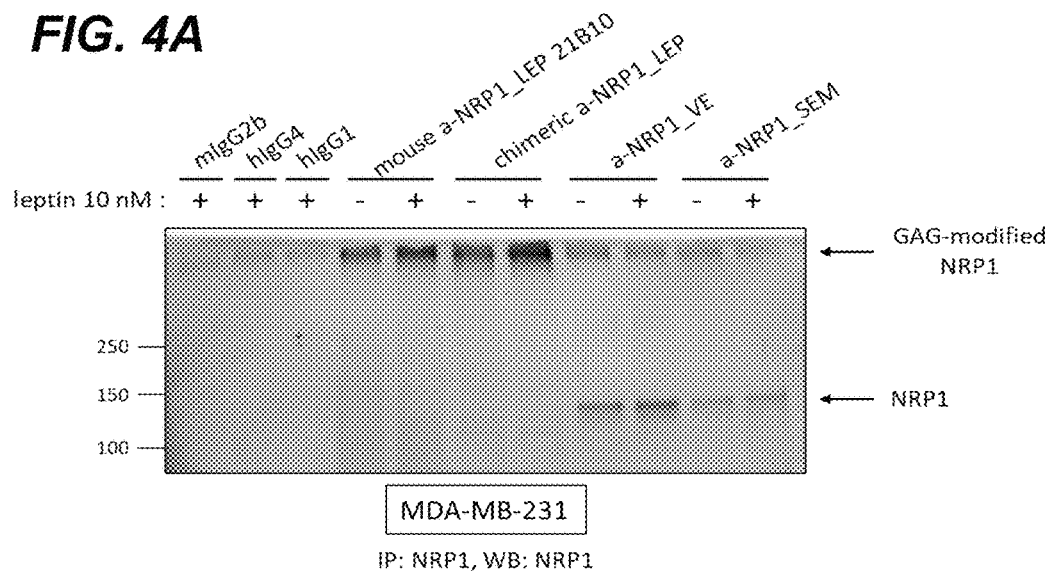
*FIG. 4B*
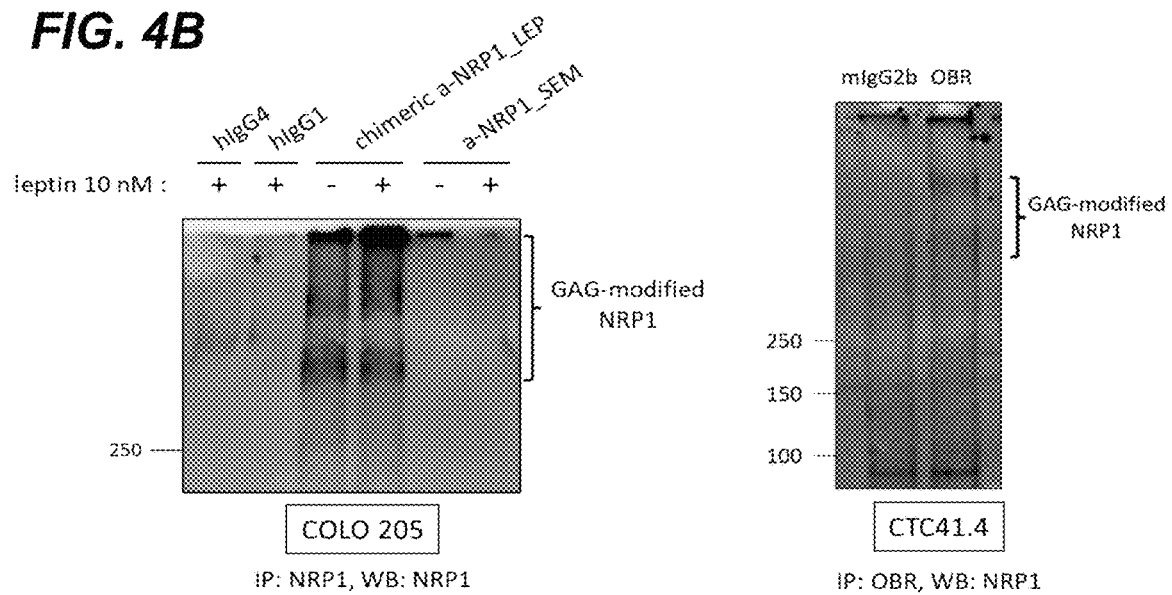
*FIG. 4C*  *FIG. 4D*

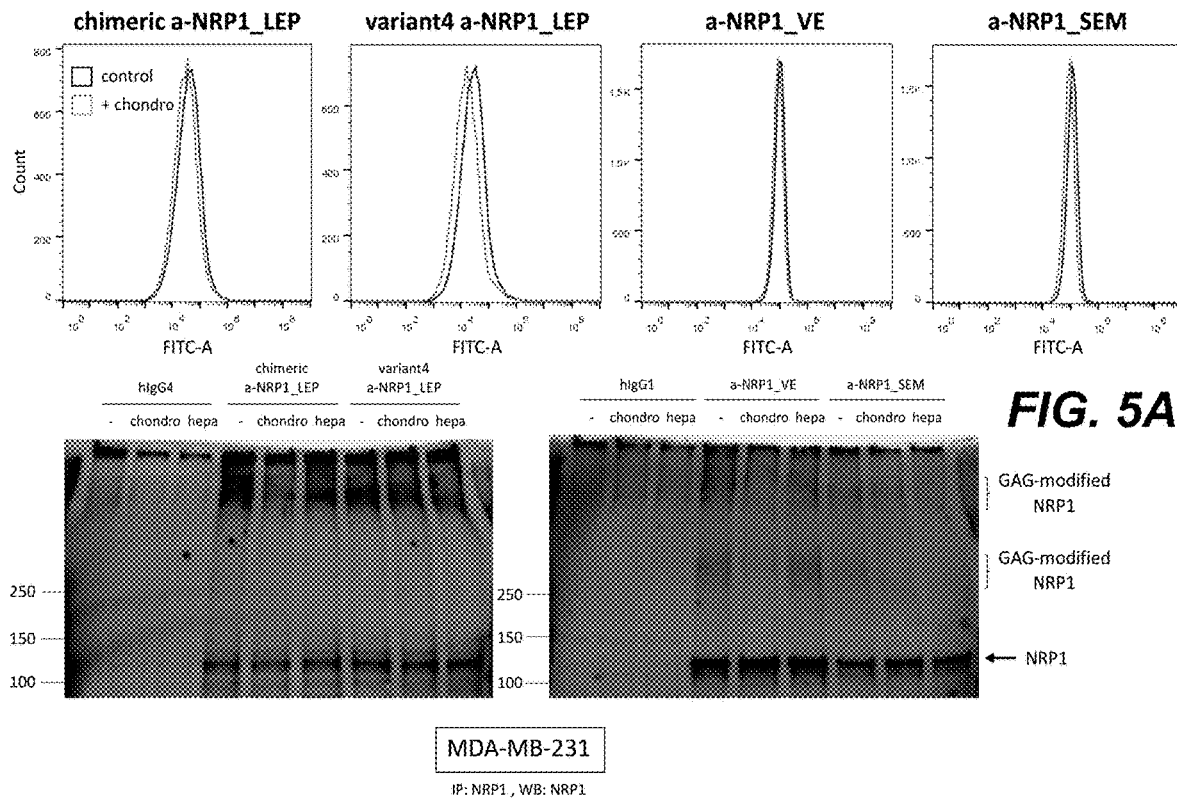
FIG. 5A
FIG. 5B
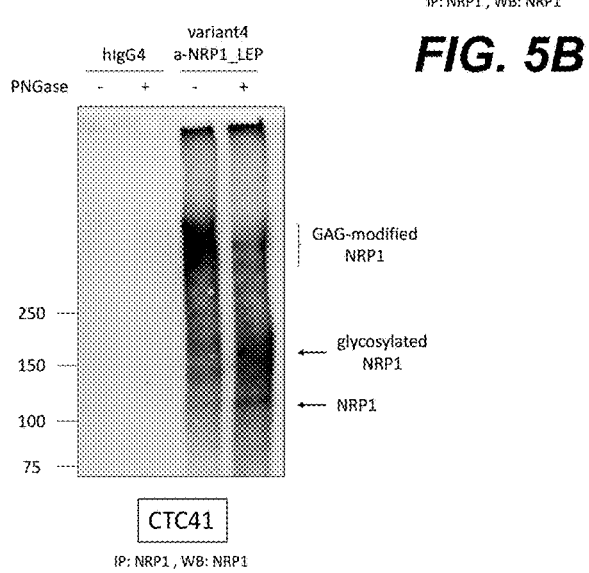
FIG. 5C

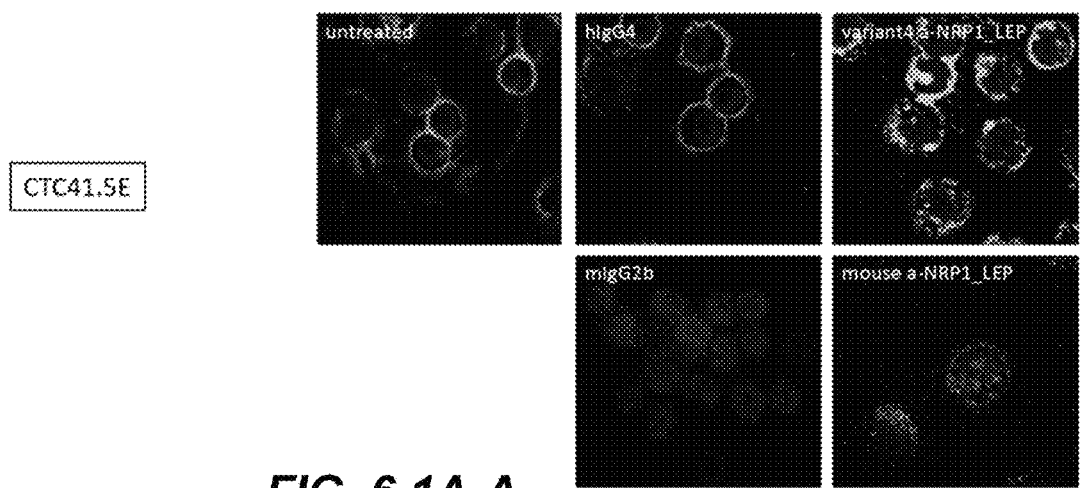
FIG. 6.1A-A
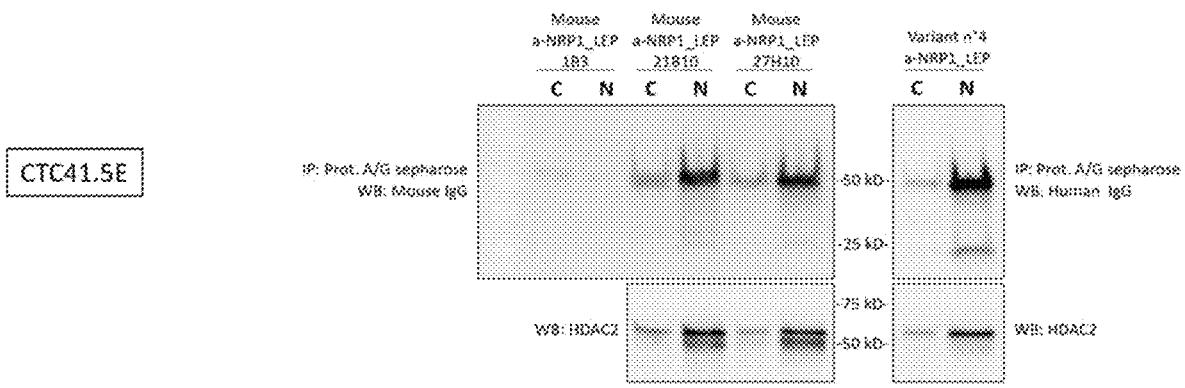
FIG. 6.1A-B

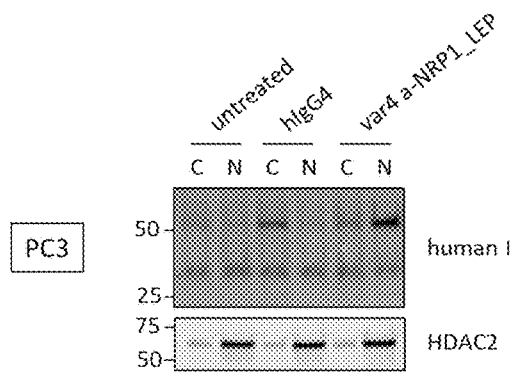
FIG. 6.2B
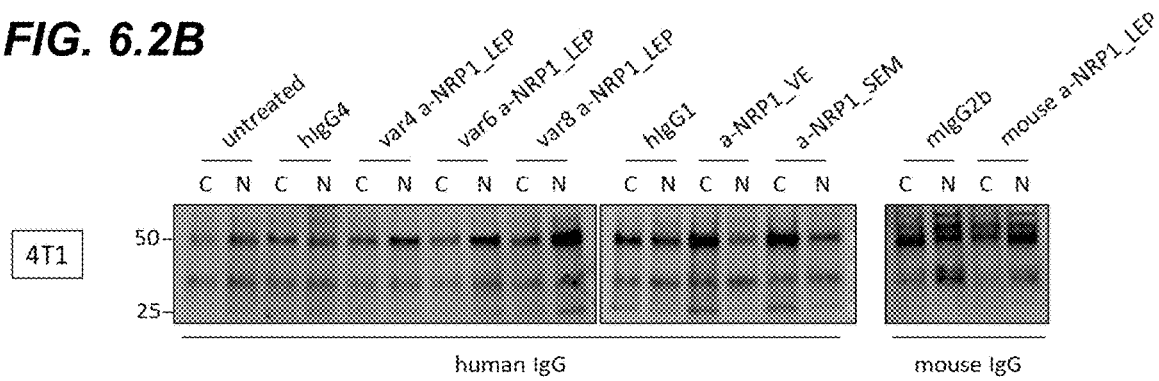
FIG. 6.2C
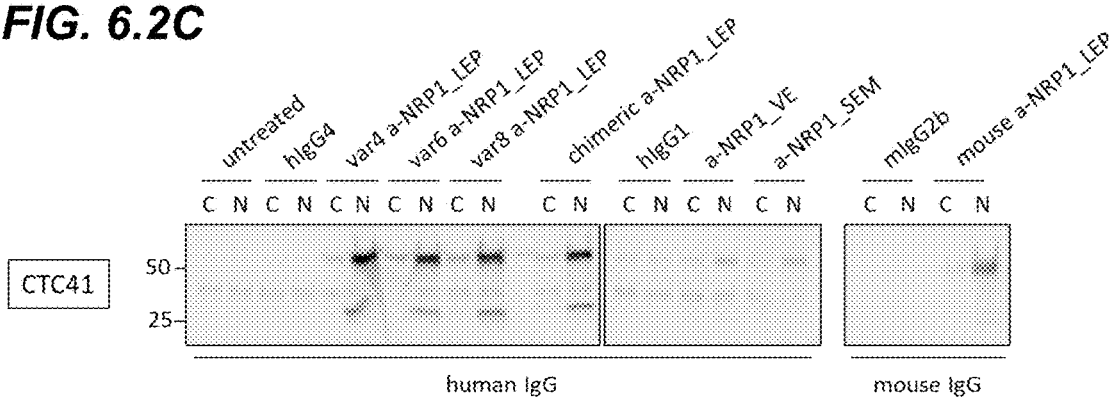
FIG. 6.2D
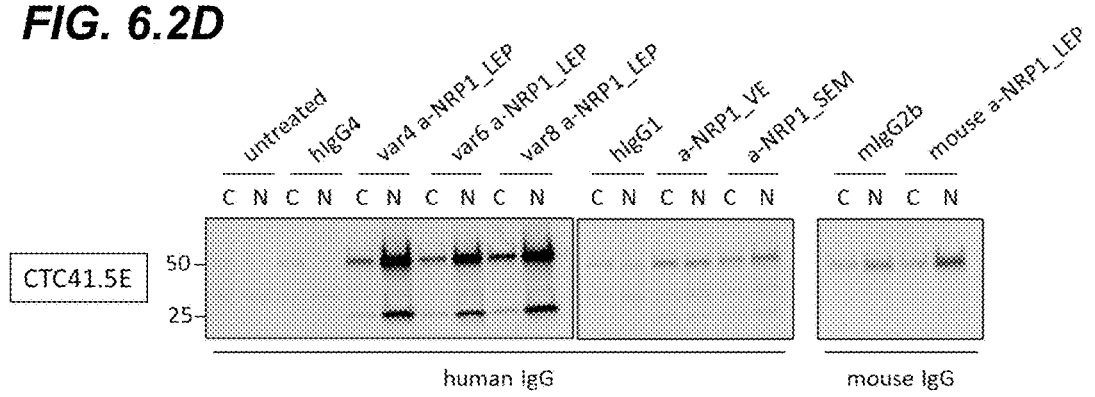
FIG. 6.2E

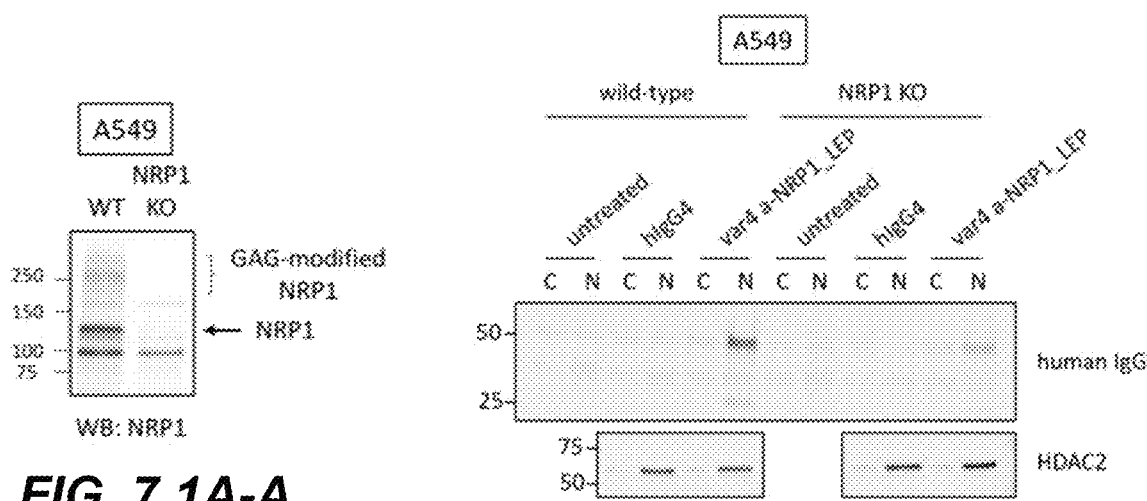
FIG. 7.1A-A
FIG. 7.1A-B
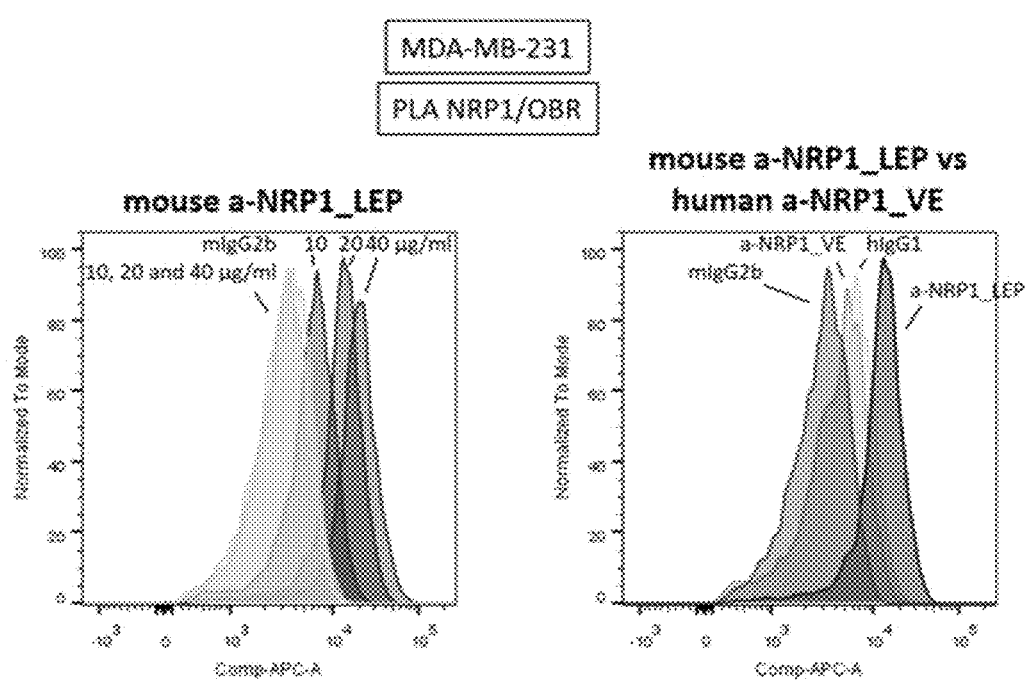
FIG. 7.1B-A
FIG. 7.1B-B

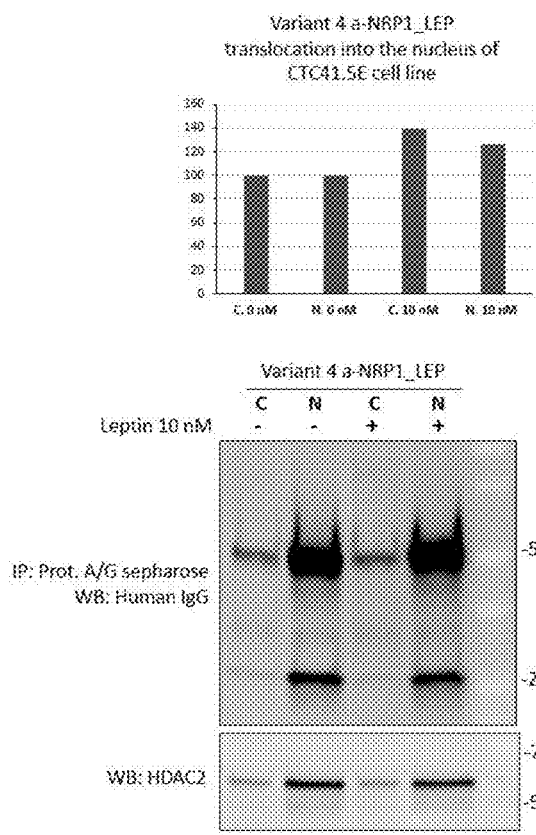 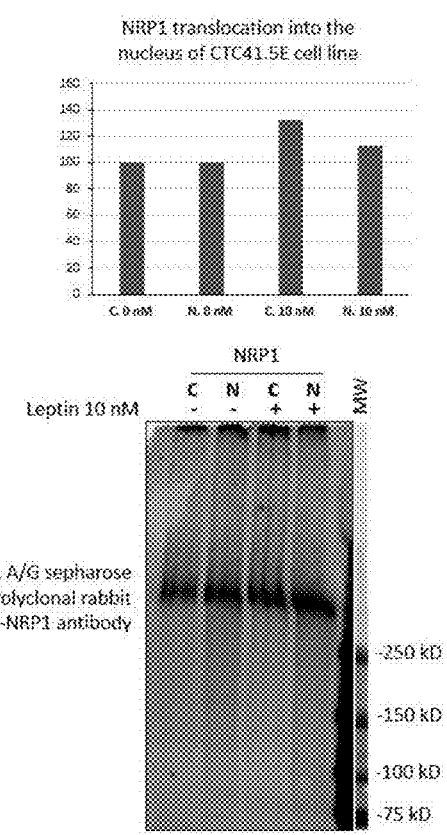
FIG. 7.2C-A  FIG. 7.2C-B

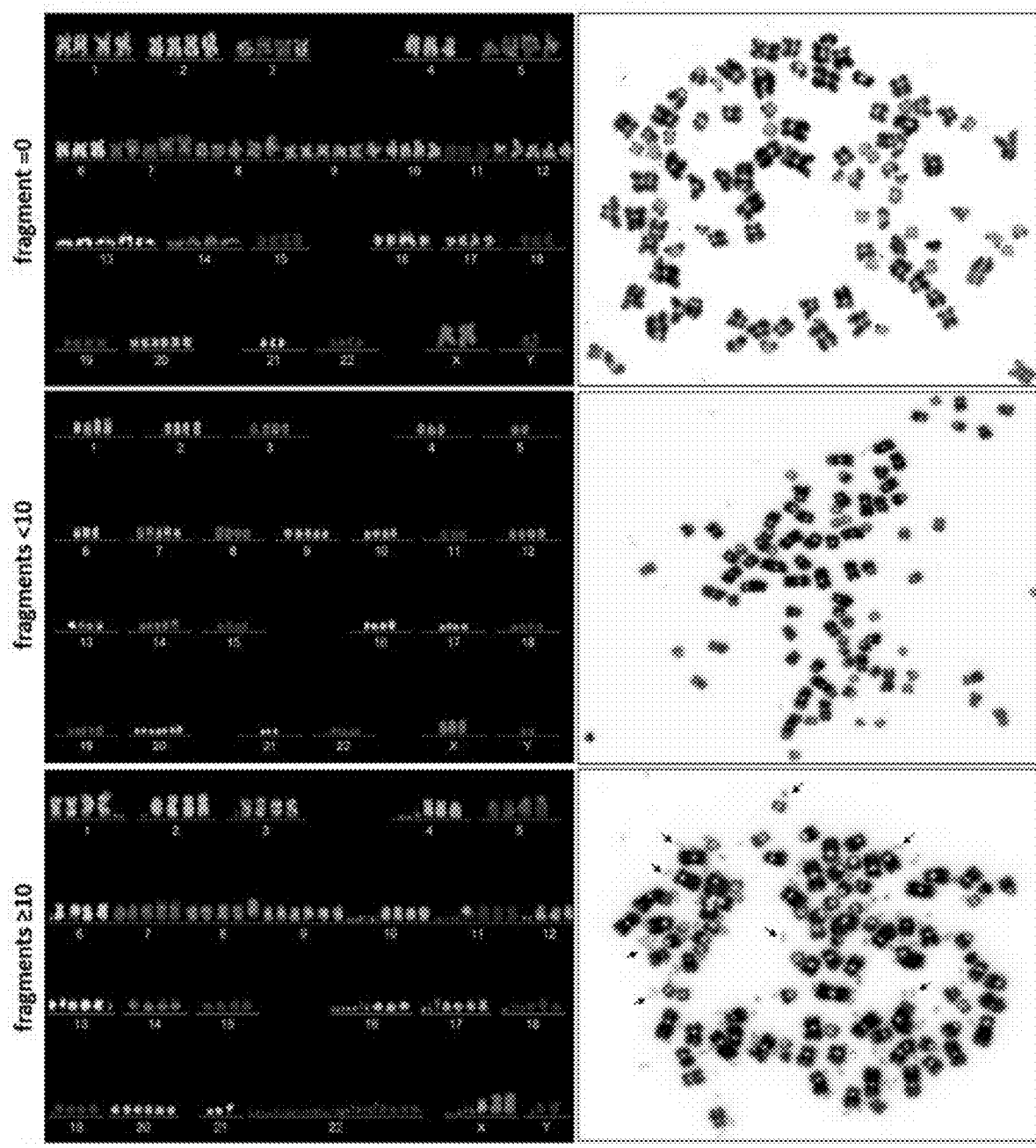
FIG. 8A-A   FIG. 8A-B

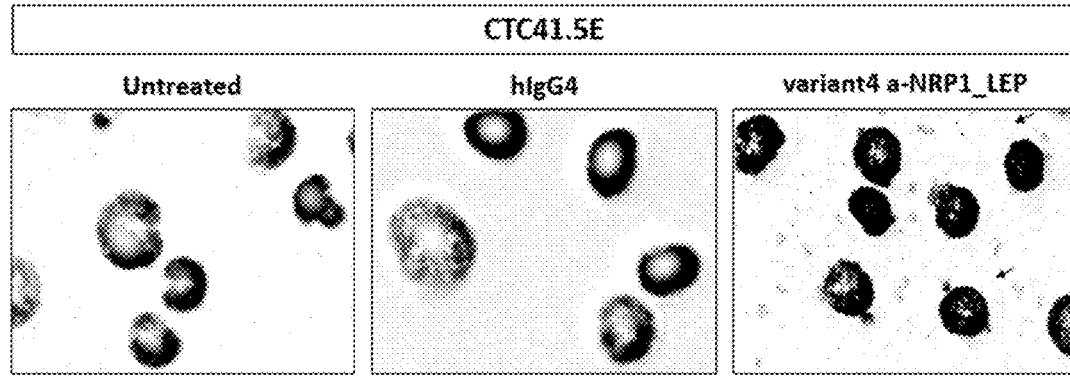
FIG. 8C-A
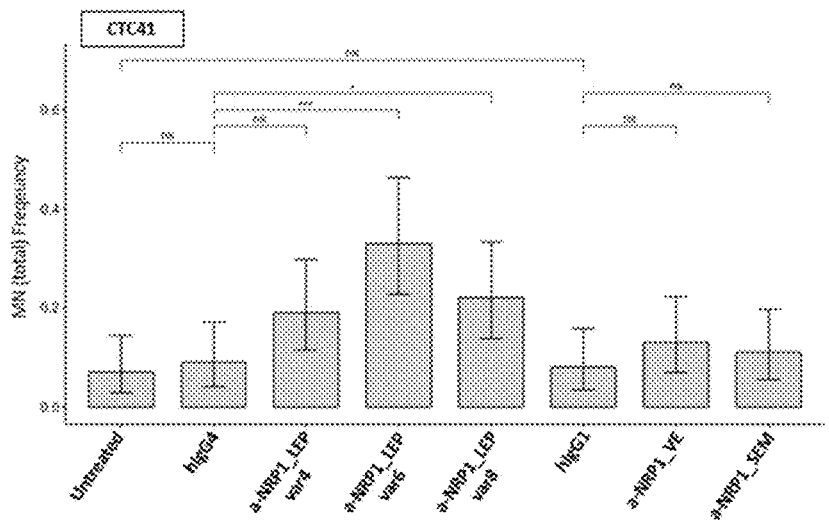
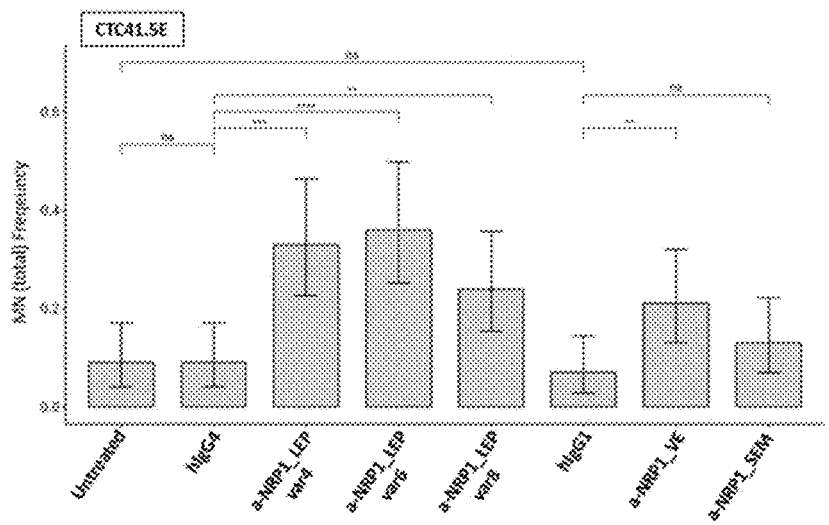
FIG. 8C-B

NEUROPILIN-1-PEPTIDE BASED ANTIBODY, HIGHLIGHTING NEW EPITOPE ASSOCIATED TO GLYCOSAMINOGLYCAN-MODIFIED NEUROPILIN-1 AND METHODS OF USE THEREOF

STATEMENT ACCORDING TO 37 CFR § 1.825(b)— AMENDMENT TO ADD OR REPLACE A "SEQUENCE LISTING" AND CRF COPY THEREOF

The XML file named seq_listing_7.12.2023_P17595US.xml created on 07/12/2023 with a size of 62,438 bytes is hereby incorporated herein in its entirety by this reference.

The disclosure relates to the field of NRP-1 peptides vaccines corresponding to epitopes associated to diseases and capable to trigger the immune response such as production of anti-NRP-1 antibodies with specificity to GAG-modified NRP-1 that are able to block DNA damages response (DDR). In particular, NRP-1 peptides vaccines and their derived anti-NRP-1 antibodies (NRP-1 peptides antibodies) specific for an epitope located in the binding domain of leptin on NRP-1 that are able to enter into the cell nucleus and to block DNA damages response (DDR) and having properties of interest in the treatment of diseases involving NRP-1/OBR complex. The NRP-1 peptide vaccines and the NRP-1 peptides antibodies are of interest in diagnosis and therapies, especially in diseases related to DNA Damage Response and Glycosaminoglycans.

FIELD OF THE INVENTION

Immunotherapy is one of the most potent tools for auto-immune diseases, infectious diseases and cancers treatment. Different approaches are used for immunotherapies development including monoclonal antibodies, cell therapies, cytokines and vaccines.

In general, immunotherapeutic monoclonal antibodies are largely used; especially for cancer treatment. Compared to traditional antibodies, immunotherapies based on peptide-antibodies or on peptide vaccines become a more useful approaches for clinical diagnosis and targeted therapies since they can be directed to any peptide of the intracellular or extracellular domains, or conserved regions, or specific conformations or to post-translational modification which are difficult to control when using proteins. Immunotherapies based on peptide vaccine strategies are also in progress with the aim to target cell-specific neoantigen or antigens expressed by cancer or infected cells for the activation of a specific immune cell such as lymphocytes (T and B cells), dendritic cells (DC), natural killer cells (NK) and macrophages. In the case of peptide-based vaccine, patient's immune system activation depends on the peptide's immunogenicity which is correlated with a number of factors, including composition, length, administration route and more importantly for their emerging from the functional domains of proteins such as ligand binding domains, post-transcriptional modification domains or cell-cell contact domains (Lu R M et al., *J Biomed Sci.*, 2020, 27:1; Zhang L et al., *Theranosiics*, 2019, 9:7807-7825; Trier N et al., *Int J. Mod Sci.*, 2019,20:6289).

As disclosed herein, NRP-1 peptide (Npep) identified by molecular docking method as NRP-1 peptide corresponding to Leptin-binding domain for NRP-1/OBR complex signaling (WO2017050793) has shown a huge potential for peptide-based vaccine applications regarding its properties as an antigen associated to NRP-1 functional domain and capacity to induces neutralizing antibody with a high specificity to GAG-modified NRP-1 that could be implicated in auto-immune diseases, viral infections and cancers.

The antigen's potential of NRP-1 peptide (Npep) of the invention was demonstrated in mouse model peptide-vaccine by inducing production of anti-NRP-1 antibodies neutralizing leptin-induced NRP-1/OBR signaling and having immunotherapeutic properties in mouse cancer model.

The cell surface glycoprotein, Neuropilin-1 (NRP-1), also known as CD304, is widely recognized as a potential target not only for cancer treatment by targeting cancer cells, angiogenesis or immune cells but also for metabolic, inflammatory and infectious diseases (Wilson A M et al., *Sci Immunol.*, 2018, 3:4626; WO 2015/124588).

Neuropilin-1 (NRP-1) is a protein organized as a large extracellular domain consisting of three major segments, namely two CUB domains (denoted a1/a2) and two coagulation factor V/VIII domains (denoted FV/VIII or b1/b2), followed by a MAM domain (denoted c) and a short cytoplasmic tail (CP) devoid of a catalytic activity, but containing a C-terminal SEA sequence that represents a consensus binding motif for proteins containing the PD2 (PSD-95, Dlg, ZO-1) domain which promotes the formation of complexes with signaling components (Gu C et al., *J. Biol Chem.*, 2002, 277:18069-76; Geretti E et al., *Angiogenesis.*, 2008, 11:31-9; Prahst C et al., *J Biol Chem* 2008, 283:25110-25114).

The multiple functions of NRP-1 in angiogenesis (Soker S et al., *Cell.*, 1998, 92:735-45) in immune response (Tordjman R et al., *Nat Immunol.*, 2002, 3:477-82; Lepelletier Y et al., *Eur J Immunol.*, 2006, 36:1782-93; Lepelletier Y et al., *Proc Natl Acad Sci. USA.*, 2007, 104:5545-50), in neuronal development (Kitsukawa T et al., *Development.*, 1995, 121:4309-18; He Z and Tessier-Lavigne M., *Cell.*, 1997, 90:739-51), in virus entry (Ghez D et al., *J Viral.*, 2006, 80:6844-54; Cantuti-Castelvetri L, et al., *Science.*, 2020, 370:856-860; Wang H B et al., *Nat Conmun.*, 2015, 6:6240) and in the regulation of hematopoiesis (Tordjman R et al., *Blood.*, 1999, 94:2301-9 and Belaid-Choucair Z et al., *Stem Cells.* 2008, 26:1556-64) as a protein lacking signal transduction is associated with its interaction properties with ligands and their cognate receptors with a specific binding domain thus inducing a specific signaling pathway for a specific function.

Several studies describe NRP-1 as a potential therapeutic target for cancer treatment to inhibit metastasis, drug resistance, and immune checkpoint and for viral infection treatment. (Chaudhary B et al., *Cancer Immunol Immunother.*, 2014, 63:81-99; Chuckran C A et al., *J Immunother Cancer.*, 2020, 8:e000967; Dumond A et al., *Front Cell Dev Biol.*, 2020, 8:662). Candidates in clinical development targeting NRP-1 functions are primarily antibodies with inhibitory activity of the binding of two primarily studied ligands, semaphorins and VEGF: ASP1948/PTZ329 from Astellas Pharma (Delgoffe G M et al., *Nature.*, 2013, 501:252-6; Yano H et al., *Immunology.*, 2019, 157:232-247; NCT03565445) and MNRP-1685A from Roche (Shumaker R C et al., *Pharmacol.*, 2014, 73:1109-17); NCT00747734; NCT00954642) respectively. These two antibodies differ in their exclusive binding capabilities to NRP-1 al/a2 or b 1/b2 domains respectively which correspond but not exclusively to Semaphorins (Sema3A, Sema4A) and VEGF, VEGFB and P1GF2 binding domains to NRP-1.

Other strategies targeting NRP-1 such as small molecules or peptide sequences are also under development but do not have properties of the invention (Liu S D et al., *Chin Med J (Engl).*, 2020, 134:508-517).

Although the many ligands and their corresponding receptors (SEMA3/PLEXIN, VEGF/VEGFR, P1GF/VEGFR, HGF/cMET, TGFβ1/TGFβPRs, PDGF/PDGFR, FGF/FGFR2, Galectin, EGF/EGFR share the same interaction domains of their common partner NRP-1 (Dumond A et al., *Front Cell Dev Biol.*, 2020, 8:662), the latter would have most likely a specificity that could differentiate them: as a peptide sequence specific to each ligand and receptor interaction with NRP-1.

Interestingly, the discovery of Leptin and its cognate receptor OBR (Leptin Receptor) has confirmed this hypothesis by showing that although Leptin and VEGF bind to the same domain (b 1 domain), the interaction sequence must be different since both are able to bind simultaneously to NRP-1 (WO2017050793; Polypeptides capable of inhibiting the binding between Leptin and Neuropilin-1).

Although it has been clearly demonstrated that Sema3A competes with VEGF for binding to NRP-1 since Sema3A binds not only to its major a1/a2 binding domains but also to b1; Wei-Ching Liang and his colleagues were able to generate antibodies that binds specifically to a1-a2 NRP-1 or b1-b2-NRP-1 domains (named here a-NRP1_SEM and a-NRP1_VE respectively as described below) (Liang W C et al., *J Mol Biol.* 2007 366:815-29) compared to antibodies of the invention that binds specifically to a peptide sequence in b 1 domain corresponding to Leptin binding (WO2017050793) and named here a-NRP1_LEP as described below.

Although they share the same b 1 binding domain, Leptin and VEGF have a noncompetitive binding to NRP-1 and allows us to extrapolate that Sema3a also has a distinct binding sequence to NRP-1 compared with Leptin.

In addition to the organization of NRP-1 proteins as a large extracellular domain consisting of three major segments, alternative splicing of the NRP-1 primary transcript leads to the production of several NRP-1 protein isoforms that differ not only in their forms (soluble and membrane) but also in their sizes ranging from 60 to 923 amino acids (Rossignol M et al., *Genomics.*, 2000, 70:211-22; Cackowski F C et al., *Genomics.* 2004, 84:82-94; Gagnon M L et al., *Proc Natl Acad Sci USA.*, 2000, 97:2573-8; Tao Q et al., *Angiogenesis.*, 2003, 6:39-45) but also in their post-translational modification properties, including glycosylation (Wu M H et al., *Sci Rep.*, 2017, 7:11006) such as N-Glycosylation (Huang X et al., *Nat Commun.*, 2019, 10:3708.), and O-Glycosylation (Zacchi L F et al., *Glycoconj J.*, 2016, 33:359-76), (Windwarder M et al., Glycoconj J. 2016, 33(3):387-97) and modifications by glycosaminoglycans (GAG) such as chondroitin sulfate and heparan sulfate (Frankel P et al., *EMBO Rep.*, 2008, 9:983-9; Shintani Y et al., *EMBO J.*, 2006, 25:3045-55). The glycosaminoglycans that could play an important role in diseases implicating NRP-1 as reported in the detailed description of the invention.

The already developed antibodies target the tumor progression by inhibiting either the angiogenesis by blocking VEGF binding to NRP-1 thus NRP-1/VEGFR2 signaling of endothelial cells (Patnaik A et al., *Cancer Chemother Pharmacol.*, 2014, 73:951-60); NCT00747734; NCT00954642) or by activating immune response by blocking regulatory T lymphocytes (Treg) by inhibiting semaphorins (SEM34/SEMA4A) binding to NRP-1 thus blocking NRP-1/Plexins signaling pathway (Delgoffe G M, *Nature.*, 2013, 501:252-6; Yano H et al., *Immunology.*, 2019, 157:232-247; NCT03565445).

Although NRP-1 is a therapeutic target of interest in the treatment of cancer or infectious diseases, no antibodies have reached yet a clinical approval and are now part of the therapeutic arsenal.

BRIEF DESCRIPTION OF THE INVENTION

The invention concerns NRP-1 peptide corresponding to an epitope included in the 3D structure of post-transcriptional modified NRP-1.

More specifically, this peptide corresponds to any consensus sequence associated to the post-transcriptional modified NRP-1 splice variants of the different isoforms. Further, this peptide derives from the glycosaminoglycans (GAG)-modified NRP-1 3D structure.

In a preferred embodiment, the NRP-1 peptide corresponds to any functional domain of NRP-1 associated to any signaling pathway and its corresponding ligand and receptor. More preferably, this functional domain of NRP-1 is associated with NRP-1/OBR complex signaling, in particular to leptin binding domain. In a particular embodiment the NRP-1 peptide corresponds to leptin binding domain associated to NRP-1/OBR complex signaling.

The peptides vaccine of the invention can be used to trigger immune response and to block DNA Damage Response (DDR).

In the context of the invention, the immune response implies at least anti-NRP-1 antibodies able to target Leptin binding domain on NRP-1, blocking thus signaling pathways of NRP-1/OBR complex expressed simultaneously on multiple type of cancer cells and cells of the tumor microenvironment (T lymphocytes, macrophages, cancer associated fibroblast, . . . ) (FIG. 1).

The invention also concerns anti-NRP-1 antibodies generated by vaccination strategy involving NRP-1 peptide as previously defined.

Anti-NRP-1 antibodies are characterized in that they are capable of inhibiting the NRP-1 signaling pathways. This signaling pathway can correspond to any functional domain of NRP-1 associated to any signaling pathway and its corresponding ligand and receptor. In a preferred embodiment, this functional domain corresponds to the NRP-1/OBR signaling pathway, and more precisely, it can correspond to an epitope located on functional domain of the NRP-1 protein associated to Leptin/OBR signaling, in particular in the leptin recognition domain located on b1 domain of the NRP-1 protein.

In a further embodiment, the anti-NRP-1 antibodies of the invention are able to specifically bind to a GAG-modified NRP-1 on any epitope related to any functional domain of NRP-1 associated to any signaling pathway and its corresponding ligand and receptor. The GAG modification on NRP-1 may correspond to the presence of glycosylation associated with sulfate modification.

The glycosylation can correspond to O-glycosylation or to N-glycosylation. The sulfate modification can correspond to the presence of chondroitin sulfate and/or heparan sulfate.

As used herein, the antibodies of the invention are defined as "a-NRP1_LEP" since they specifically inhibit the binding of Leptin to NRP-1, in comparison to antibodies preventing exclusively VEGF binding to NRP-1 "a-NRP1_VE" or exclusively semaphorins binding to NRP-1 "a-NRP1_SEM".

Interestingly, neither a-NRP1_SEM nor a-NRP1_VE were able to bind to the peptide sequences used for the generation of the antibodies inhibiting Leptin binding to NRP-1, a-NRP1_LEP (Table 2). Especially the a-NRP1_LEP antibodies were compared to TAB-264 inhibiting exclusively the binding of VEGF to NRP-1 (a-NRP1_VE) which corresponds to the antibody clinically tested by Roche, Vesencumab (MNRP-1685A) (Liang W C et al., *J Mol Biol.*, 2007, 366:815-29; Weekes C D et al., *Invest New Drugs.*, 2014, 32:653-60; Xin Y et al., *Clin Cancer Res.*, 2012, 18:6040-8), and to YW64.3 inhibiting exclusively the binding of semaphorins to NRP-1 (a-NRP1_SEM) (Liang W C et al., *J Mol Biol.*, 2007, 366:815-29), equivalent to the antibody developed by Potenza (WO2018119171A1) under clinical trial by Astellas ASP1948 (PTZ-329) (NCT03565445) (Delgoffe G M et al., *Nature.*, 2013, 501:252-6; Chuckran C A et al., *J Immunother Cancer.*, 2020, 8:e000967).

In contrast to a-NRP1_VE and a-NRP1_SEM, antibodies of the invention a-NRP1_LEP present high specificity for the GAG-modified NRP-1, associated with either chondroitin or heparan sulfate, expressed on multiple cancer cell surface, especially on circulating cancer stem-like cells (CTCs).

An exception is observed with the A459 lung cancer cell line, while a-NRP1_VE is able to recognize a GAG-modified NRP-1, a-NRP1_LEP is able to recognize especially a glycosylated form of NRP-1 (≤150 kDa) and less the GAG-modified NRP-1 (>150 kDa) as confirmed in CRISPR-Case9 NRP-1-A549 cell line (FIG. 4A-C).

Thus, we can speculate a specificity associated not only to the composition of the GAG (N-Glycosaminoglycans and O-Glycosaminoglycans) in particular chondroitin sulfate (CS) and heparan sulfate (HS) but also of their size, their modification by either acetylation, sulfation and/or epimerization (Morla S., *Int J Mol Sci.*, 2019, 20(8):1963; Chen J et al., *Front Cell Dev Biol.*, 2021, 30; 9:760532), their binding site to the core protein named here neuropilin-1. This specificity can also rely to the cell type and to the responsiveness of the ligands and their cognate receptors as already reported for VEGF/VGFR2 signaling associated to the GAG-binding site Serine 612 in vascular endothelial cells (ECs) and in smooth muscle cells (SMCs). Shintani and his colleagues have reported that although Glycosylation increased VEGF binding in both cell types (ECs and SMCs), the differential GAG composition of NRP-1 mediates opposite responsiveness to VEGF.

A differential responsiveness that we could observe between different partners of NRP-1 by comparing the effect of their corresponding neutralizing antibodies a-NRP1_LEP for leptin signaling inhibition; a-NRP1_VE for VEGF signaling inhibition and a-NRP1_SEM for Semaphorins signaling inhibition. As reported in FIG. 4A the antibody of the invention a-NRP1_LEP is able to detect a GAG-modified NRP-1 that could not be detected by the a-NRP1_VE in CTCs cells. However, the antibody of the anterior art a-NRP1_VE detects with a higher specificity the GAG-modified NRP-1 form in A549 cell line than the antibody of the invention a-NRP1_LEP (FIG. 4A).

Interestingly, in contrast to the antibody of the anterior art a-NRP1_VE, we could observe that the antibody of the invention a-NRP-1 LEP were not able to detect a doxycycline-inducible GAG-modified NRP1-FS corresponding to 0-Glycosylation site at 5612 reported to be associated to angiogenesis induced by VEGF as demonstrated by Hendricks C and her colleagues compared to the doxycycline-inducible GAG deficient NRP1-47 at 5612 in human breast MDA-MB231 and prostate PC3 cancer cell line (Hendricks C et al., *PLoS One*, 2016, 11(10):e0165153).

However, the GAG-modified NRP-1 detected by the antibody of the invention (a-NRP1_LEP) was associated either to chondroitin sulfate or to heparan sulfate (FIG. 5) that should correspond to 0-Glycosylation at serine 5612 but with different level of modification regarding the heavy size of the detected GAG form (>250 kDa). NRP-1 is also reported to be heavily glycosylated at the c/MAM domain (628-646) in close proximity to the known S612 glycosaminoglycan that may affect its patho-physiological properties (Windwarder M et al., *Glycoconj J.*, 2016, 33(3):387-97).

Thus, the specificity of the glycosylation sites of NRP-1 and the implication of the GAG composition on the GAG-modified NRP-1 functions should be considered when developing targeted therapies. For example, N-glycosylation loss at asparagine sites Asn150 or Asn261 in NRP-1 splice variants (depleted for exon 4 and 5) triggers new function implicating Met and HGF than the GAG-modified NRP-1 at serine S612 implicating VEGF (Huang X et al., *Nat Commun.*, 2019, 10(1). 3708).

A specificity which could be extended for other known Neuropilin-1 partners such as TGFB, VEGF B, VEGFC, VEGFRs, TGFB RI/II/III, P1GF, PDGFs, PDGFRs, EGF, EGFR, FGF, FGFR, HGF, HGFR, SEMA4 and Plexin Al and a recently identified partners PDL-1/2 and PD1 (Rossignol J et al., *iScience.*, 2022, 25(6):104353) that we aim to identify in order to propose targeted NRP1-peptide vaccine with a specificity of GAG-modified NRP-1 to each of its corresponding ligand.

In the case of viral infection NRP-1 was associated to HTLV-1 known for its implication in adult T-cell leukemia (ATL), SARS-Cov-2 and EBV virus entry. In the case of NRP-1 dependent HTLV-1 and EBV entry, the mechanism of action implicates VEGFR and EGFR/RAS/ERK signaling respectively with the association of the glycosaminoglycans and DNA damage response. Thus, the identification of the NRP-1 sequence associated to a specific GAG-modified NRP-1 related to each virus entry and the DNA damage response as reported for HTLV-1 (Boxus M et al., *Retrovirology*, 2012, 5; 9:2) may represent a very innovative strategy for anti-virus vaccines related to cancer induction or other infectious disease (Wang H B et.al, *Nat Commun.*, 2015, 11; 6:6240; Jones K S et al., Viruses, 2011, 3(6):794-810; Gudowska-Sawczuk M et al., *J Clin Med.*, 2021, 24;10 (13):2772).

In vitro characterization of a-NRP1_LEP in comparison to a-NRP1_VE and a-NRP1_SEM on human and mouse cancer cell lines and on human stem-like cells from circulating tumor cells CTCs (Table 4) (Cayrefourcq L et al., Cancer Res., 2015, 75:892-901; Cayrefourcq L et al., *Mol Cancer.*, 2021, 20:30; Soler A et al., *Sci Rep.*, 2018, 8:15931) has revealed unexpected properties of antibodies of the invention. Indeed, they are able to enter into the nucleus independently of a cell type specificity since we are able to observe the a-NRP1_LEP antibody entry into the nucleus of human and mouse cancer cell line (breast, lung, colon and prostate cancer cells) (FIGS. 6.1 and 6.2) as well as of human peripheral blood mononuclear cells (PBMCs) from healthy donors (data not shown). This intra-nucleus entry is NRP-1-dependent as demonstrated on the wild-type and a partially NRP-1-knockout A549 cell lines (FIGS. 7.1 A-a and A-b). More interestingly, the a-NRP1_LEP antibody entry into the nucleus is mediated by the leptin-dependent NRP-1/OBR complex as observed by the dose-dependent increase of NRP-1/OBR complex formation in cells treated with a-NRP1_LEP whereas a-NRP1_VE has no effect (FIGS. 7.1 B-a and B-b).

This observation is consistent with the leptin-induced entry of a-NRP1_LEP antibody and NRP-1 protein into the cell nucleus (FIG. 7.2) accordingly to the already reported data on leptin-induced NRP-1/OBR complex entry in the nucleus in dose dependent manner (WO12015/124588, Methods and pharmaceutical compositions for the treatment of diseases mediated by the NRP-1/OBR complex signaling pathway).

Regarding the implication (i) of leptin and its specific receptor OBR, (ii) of Glycosaminoglycans and (iii) of neuropilin-1 in the stemness of cancer cells as reported in independent publications, regarding the high recognition of the GAG-modified NRP-1 in CTCs by the antibodies of the inventions a-NRP1_LEP compared to other cells lines and the antibodies of the anterior art a-NRP1_VEGF and a-NRP1_SEM and regarding the increase of NRP-1 and Leptin receptor (OBR) gene expression in CTC415E associated to drug resistances and therapy failures compared to CTC41 collected before treatment; we decided to focus our investigations on the consequence of a-NRP1_LEP entry into the nucleus on the cell fate mainly in circulating cancer stem-like cells derived from the same patient before treatment (CTC-41) and in drug resistant circulating cancer stem-like cells after chemotherapy and antiangiogenic treatment (CTC-415E) (Takakura N., Cancer Sci., 2012, 103: 1177-81; Zheng Q et al., Endocr Relat Cancer., 2013, 20:797-808; Mishra A K et al., PLoS One., 2017, 12:e0178454; Tang Y H et al., Breast Cancer Res., 2022, 24:8; Vitale D et al., FEBS J., 2019, 286:2870-2882).

Thus, our investigation on the consequence of a-NRP1_LEP entry into the cell's nucleus (FIGS. 6.1 and 6.2) and its binding to the chromatin (FIG. 10) in vitro and in vivo (FIGS. 11A and B) has revealed a genotoxic effect by inducing DNA damages and telomere shortening in the circulating tumor cells (CTC) collected before and after treatment from patient who has presented resistance to chemotherapy and to Bevacizumab either in vitro (FIGS. 8A-C) and in vivo (FIG. 12) but not in human peripheral blood mononuclear cells (PBMCs) collected from healthy donors that could be explained by the absence of the excessive DNA Damage Response activity in the healthy PBMCs (FIG. 8D) compared to cancer cells. In addition, the effect of a-NRP1_LEP antibody in telomere shortening correlates with the already reported association of leptin as a regulator of hTERT gene expression and activity in cancer such as breast cancer and hepatocellular carcinoma (Stefanou N et al., BMC Cancer., 2010, 1186/1471-2407-10-442; Ren H et al., Biochem Biophys Res Commun., 2010, 394(1):59-63)

The molecular characterization of these CTCs by Dr. Catherine Alix-Panabieres' s team has revealed the crucial role of genes regulating energy metabolism and DNA repair (Alix-Panabieres C et al., Clin Chem., 2017, 63:700-713), which correlate with the role of leptin in energy metabolism regulation (de Candia P et al., J Exp Med., 2021, 218: e20191593) and the possible neutralizing effect of antibodies of the invention on the DNA repair, supported by the enrichment of proteins involved in DNA repair pathways such as double strand break (NHEJ: XRCC5/XRCC6, HR: WRN) and single strand break (BER: LIG3, NER: XPC) repair mechanisms from CTCs and A549 cell extracts as revealed by mass spectrometry analysis of the immunoprecipitated NRP-1 with a-NRP1_LEP antibody compared to a-NRP1_VE (Table 5).

The PARP1 protein, known to be implicated in multiple DNA repair mechanisms, is shown to be enriched by a-NRP1_LEP targeting leptin dependent NRP-1/OBR complex signaling in both cell types (CTCs and A549) and not by a-NRP1_VE targeting VEGF induced NRP-1/VEGFR signaling. This observation is in line with already published data implicating NRP-1 in the resistance to PARPi (Olaparib) without any indication of direct interaction between NRP-1 and PARPs (Vescarelli E et al., J Exp Clin Cancer Res., 2020, 2;39(1):3). This observation leads us to conclude that the mechanisms of action of leptin dependent NRP-1/OBR complex signaling in DNA repair is completely different from VEGF induced NRP-1/VEGFR complex signaling. While VEGF/NRP-1/VEGFR signaling pathway has been reported to modulate PARP1 mRNA and protein expression (HOrmann M et al., J Thromb Haemost., 2011, 9:1391-403, Mey L et al., Neurobiol Dis., 2013, 59:111-25), leptin/NRP-1/OBR interact directly with the DNA repair machinery as confirmed by the DNA damage and chromosomes pulverization after cells treatment with the neutralizing a-NRP1_LEP antibodies (FIG. 8A-C). A very interesting property of cancer stem-like cells has been revealed by the LC-MS/MS analysis using the antibody of the invention a-NRP1_LEP. In contrast to the non-stem cancer cells A549, CTCs possess the main actors of different DNA repair mechanisms (NHEJ, HR, BER, NER, MMR, . . . ) that could explain the resistance of cancer stem cells to several genotoxic therapies such as radiotherapy and chemotherapy (Table 5) that could be observed in different cancer types implicating DNA damage response (DDR) (Tayoun T et al., JCI Insight., 2022, 7(11)). The association between the high GAG-NRP-1 form and the global DNA repair mechanism as revealed by the antibody of the invention a-NRP1_LEP in the circulating cancer stem-like cells (CTCs) highlights the relation between glycosaminoglycans and DNA Damage Response (DDR), a mechanism reported to be associated in the resistance of cancer stem cells to therapies and cancer relapse (Vitale D et al., FEBS J., 2019, 286:2870-2882; Ahrens T D et al., Front Cell Dev Biol., 2020, 8:749).

The in-vivo analysis of the antibody of the invention a-NRP1_LEP effect by using 4T1 breast cancer cell line in syngeneic mouse model (BALB/c ByJ CRLF) has revealed an immune-modulatory action associated to lung metastasis decrease by increasing CD4 $^+$ T lymphocyte infiltration into the tumor and CD8+T lymphocyte activation as demonstrated by Granzyme B (GrB) and Perforin (Perf) expression and cell-cell interaction between CD8 $^+$GrB$^+$ and CD4 $^+$Foxp3$^-$ illustrated in FIG. 13A-D.

The immune-modulatory action of the antibody of the invention a-NRP1_LEP could be associated either to its genotoxic effect on cancer cells which in turn activates immune cells (indirect mode of action) or directly by acting on immune cells of the microenvironment expressing NRP-1/OBR complex on their surface. Interestingly, the interplay between DNA damage response (DDR) inhibition and anti-cancer immunity response activation has been already reported (Chabanon R M et al., Nat Rev Cancer., 2021, 21:701-717).

Different pathways have been described for the activation of the innate and adaptative anti-tumor immune response by the DNA damage resulting from DDR deficiency or DDR inhibition therapies. such as (i) the enhancement of neoantigen generation, (ii) the immune synapse modulation by upregulation of the expression of programmed death ligand 1 (PD-L1), (iii) cytosolic immunity activation by the cGAS-STING signaling and (iv) immunogenic cell death by the exposure and release of numerous damage-associated molecular patterns (surface-exposed calreticulin) that favor the recruitment and activation of antigen-presenting cells (Chabanon R M et al., Nat Rev Cancer., 2021, 21(11):701-717; Fucikova J et al., Cell Death Dis., 2020, 11(11):1013; Galluzzi L et al., J Immunother Cancer., 2020, 8(1): e000337).

The decrease of lung metastasis could be a consequence of a DNA-damage dependent immune response as revealed by the detection of micronuclei in cells treated with a-NRP1_LEP. We tested the a-NRP1_LEP in immunodeficient mice with the 4T1 cancer cell line, there was no effect on lung metastasis decrease, meaning that the immune system is very important for the effect of a-NRP1_LEP, the antibodies of the invention. These observations lead us to consider the leptin-induced NRP-1/OBR complex as a great target for the activation of the anti-tumor immune response of the same importance as PD-1, PD-L1 and anti-CTL4. While therapeutic anti-PD-1 such Keytruda (Pembrolizumab) and Opdivo (Nivolumab) have shown a direct effect on exhausted cytotoxic CD8 lymphocytes re-activation and the increase of their infiltration into the tumor, the a-NRP1_LEP antibodies show an action on T CD4$^+$ cells by increasing their number inside the tumor which in turn re-activate exhausted cytotoxic CD8$^+$ lymphocytes as detected by the cell-cell contact between CD4$^+$Foxp3$^-$ and CD8$^+$GrB$^+$ in the used model (FIG. 13 A-D).

This observation leads to consider these anti-NRP-1 LEP antibodies (i) as a first-in-class antibodies compared to other developed antibodies a-NRP1_VE and a-NRP1_SEM or under development, (ii) act differently on tumors cells and on the cells of the environment, (iii) act as immune system-modulators dependent on DNA Damage Response inhibition.

To conclude, NRP-1 peptides-based vaccine (Npep) and the antibodies of the invention a-NRP1_LEP targeting the GAG-modified NRP-1 and its partners (leptin and OBR) represent a therapeutic opportunity in cancer and infectious diseases, all based on DNA Damage Response (DDR) and immune system interplay (Poplawski T., *Curr Med Chem.*, 2019, 26:1423-1424).

DETAILED DESCRIPTION OF THE INVENTION

The invention concerns NRP-1 peptide corresponding to an epitope included in the 3D structure of post-transcriptional modified NRP-1.

In a particular embodiment, the NRP-1 peptide of the invention corresponds to a consensus sequence associated to the post-transcriptional modified splice variants of the different isoforms of NRP-1.

In a preferred embodiment, the NRP-1 peptide of the invention is part of glycosaminoglycans-modified NRP-1 3D structure.

In a preferred embodiment, the NRP-1 peptide corresponds to a functional domain of NRP-1 associated to specific binding domain of its known ligands and corresponding signaling pathways.

The NRP-1 peptide of the invention further corresponds to a functional domain of NRP-1 associated to NRP-1/OBR complex signaling, especially to leptin binding domain. This peptide is capable of inducing an immune response, especially to activate cells of the adaptative and of the innate immune system. This peptide is thus immunogenic and capable of inducing anti-NRP-1 antibodies production, as well as cytotoxic immune response.

Glycosaminoglycans (GAG) are a class of biomolecules that exist free in the extracellular matrix or covalently attached to protein, forming proteoglycans which can be expressed on the cell surface or in the intracellular milieu of mammalian cells. GAGs play an important role in various physiological and pathological processes including cancer, inflammation, infectious diseases and many more (Morla S et al., *Int J Mol Sci.*, 2019, 20:1963, Kamhi E et al., *Biol Rev Camb Philos Soc.*, 2013, 88:928-43, Jinno A et al., *Methods Mol Biol.*, 2015, 1229:567-85, Song Y et al., *Adv Exp Med Biol.*, 2021, 1325:103-116).

More precisely, anti-NRP-1 antibodies a-NRP1_LEP, generated from NRP-1 peptide-based vaccine (Npep), recognize a glycosylated NRP-1 (≤150 KDa) and with a higher specificity a glycosaminoglycan (GAG)-modified NRP-1 (>150 kDa) on an epitope located on b1 domain of the neuropilin-1 protein. The GAG modification form of NRP-1 corresponds to the presence of chondroitin sulfate and/or heparan sulfate.

As used herein, the post-transcriptional modified NRP-1 corresponds to Glycosaminoglycan modified NRP-1 (GAG-modified NRP-1) including Heparan Sulfate (HS) and Chondroitin Sulfate (CS).

As used herein, HS corresponding to linear polysaccharides is composed of GlcA-GlcNAc repeating units and modified by epimerization (C5-epimerase), N- and 0-sulfations (NS, NS3S, 2S, 3S and 6S), and by desulfation (endosulfatase).

As used herein, CS consist of a repeating disaccharide unit is composed of glucuronic acid (GlcA) and N-acetyl-galactosamine (GalNAc) and subjected to marked structural modification by 0-sulfation (4S, 6S and 4S6S) and epimerization.

The invention provided NRP-1 peptides with immunogenic properties, then these peptides can be used to generate antibodies.

The invention also concerns an anti-NRP-1 antibody generated by vaccination strategy involving NRP-1 peptide as previously defined.

The antibodies of the invention present functional properties that differentiate them from prior art anti-NRP-1 antibodies. In particular, these antibodies may inhibit the NRP-1/OBR signaling pathway, and may more particularly bind an epitope located on functional domain of the NRP-1 protein associated to Leptin/OBR signaling.

In a preferred embodiment, this domain corresponding to the leptin recognition domain is located on b1 domain of the NRP-1 protein.

Further, the antibodies of the invention are able to specifically bind to a GAG-modified NRP-1 on an epitope located on leptin recognition domain of the NRP-1 protein; said GAG modification on NRP-1 may correspond to the presence of glycosylation associated with sulfate modification. The glycosylation can correspond to O-glycosylation or to N-glycosylation, and the sulfate modification may correspond to the presence of chondroitin sulfate and/or heparan sulfate and their modifications.

In a preferred embodiment, the NRP-1 peptide-based vaccine generates antibodies that recognize a non-GAG glycosylated and GAG-modified NRP-1 bearing an 0-glycosylation associated with heparan sulfate and chondroitin sulfate or N-glycosylation (Ahrens T D et al., *Front Cell Dev Biol.*, 2020, 8:749).

Herein it is shown that the antibodies of the invention can recognize different forms of GAG-modified NRP-1 than those recognized by the antibodies of the prior art.

The NRP-1 peptide-based vaccine (NRP-1 peptide of the invention) can be used in the treatment of glycosaminoglycans-associated pathologies including cancer, inflammation and infectious diseases.

It is also shown that the epitope of the interacting domain on NRP-1 for the antibodies of the invention is distinct from that of the a-NRP1_VE antibody with NRP-1 which share the same NRP-1 b1 domain but not the same binding sequence (FIG. 3). They demonstrated by ELISA a specific binding of murine, chimeric, humanized variants of a-NRP1_LEP antibodies to synthetic peptides corresponding to leptin binding sequence on NRP-1, absent with the irrelevant human immunoglobulin and prior art antibodies (a-NRP1_VE and a-NRP1_SEM) (table 2). Thus, the antibodies according to the invention recognize a particular epitope, never described before, which is located in the b1 domain of NRP-1.

In addition to the epitope specificity, the antibody of the invention presents a specificity to a GAG-modified NRP-1 form as observed in the CTCs and A549 cell lines.

The anti-NRP-1 antibodies of the invention, a-NRP1_LEP, are capable to bind with high specificity to the glycosaminoglycan (GAG) modified form of the NRP-1 protein especially in the case of "stem cells like" cell lines (CTCs); in contrast, other anti-NRP-1 ligands as the well-known a-NRP1_VE and a-NRP1_SEM do not bind to GAG-modified NRP-1 in this type of cells.

Further, antibodies of the invention bind very weakly to non-GAG-modified NRP-1.

In a particular embodiment, the antibody of the invention can enter into the nucleus of cancer cells and induce DNA damage.

In another embodiment, the genotoxic effect of the a-NRP1_LEP seems to be specific to pathological cells since no significant DNA damage was observed neither in human hepatic and lymphoblastic cell lines, nor in human peripheral blood mononuclear cells (PBMCs) derived from healthy donors.

The invention also provides particular antibodies defined by their sequences.

In a preferred embodiment, the invention concerns an antibody derived from mouse a-NRP1_LEP n° 1 (also called 21B10 mouse antibody) and covering its humanized variants; this antibody comprises the sequences CDR-H1, CDR-H2, CDR-H3, CDR-L1, CDR-L2 and CDR-L3 as defined below:

CDR-H1 is represented by the sequence S $X_1$ $X_2$ MH (SEQ ID NO: 1)
wherein $X_1$=F or Y
$X_2$=G, S or Y
CDR-H2 is represented by the sequence $X_3$ I S $X_4$ $X_5$ $X_6$ $X_7$ $X_8$ $X_9$ $X_{10}$ Y A $X_{11}$ $X_{12}$ $X_{13}$ $X_{14}$ G (SEQ ID NO: 2)
wherein
$X_3$=Y, V or I
$X_4$=S, Y or P
$X_5$=G, S or D
$X_6$=S or G
$X_7$=S or G
$X_8$=T or S
$X_9$=I, K or T
$X_{10}$=H, Y or S
$X_{11}$=D or Q
$X_{12}$=S, K or T
$X_{13}$=V or F
$X_{14}$=K or Q
CDR-H3 is represented by the sequence RHYGSSRYWYFDV (SEQ ID NO: 3)
CDR-L1 is represented by the sequence $X_{15}$ A S Q $X_{16}$ $X_{17}$ $X_{18}$ S $X_{19}$ L $X_{20}$ (SEQ ID NO: 4)
wherein $X_{15}$=K or R
$X_{16}$=D or S
$X_{17}$=I or V
$X_{18}$=K or S
$X_{19}$=Y or W
$X_{20}$=S or A CDR-L2 is represented by the sequence $X_{21}$ A $X_{22}$ S $X_{23}$ $X_{24}$ $X_{25}$ (SEQ ID NO: 5)
where $X_{21}$=Y or D
$X_{22}$=T or S
$X_{23}$=L or R
$X_{24}$=A or E
$X_{25}$=G, S or T
CDR-L3 is represented by the sequence $X_{26}$ Q Y $X_{27}$ $X_{28}$ S $X_{29}$ Y T (SEQ ID NO: 6)
where $X_{26}$=L or Q
$X_{27}$=G or S
$X_{28}$=E or S
$X_{29}$=P or S In preferred embodiments, the antibody of the invention is chosen among the following antibodies:

An antibody or antibody fragment comprising the sequences CDR-H1, CDR-H2, CDR-H3, CDR-L1, CDR-L2 and CDR-L3 as defined below:
CDR-H1: SFGMEI (SEQ ID NO: 7)
CDR-H2: YISSGSSTIHYADTVKG (SEQ ID NO: 8) or YISSGSSTIYYADTVKG (SEQ ID NO. 35)
CDR-H3: RHYGSSRYWYFDV (SEQ ID NO: 9) or RHYGRSRYWYFDV (SEQ ID NO. 36)
CDR-L1: KASQDIKSYLS (SEQ ID NO: 10)
CDR-L2: YATSLAG (SEQ ID NO: 11) or YATSLAD (SEQ ID NO: 38)
CDR-L3: LQYGESPYT (SEQ ID NO: 12).
More preferably:
Antibody a-NRP1_LEP n° 1 of fragment thereof comprising the CDR:
CDR-H1: SFGMH (SEQ ID NO: 7)
CDR-H2: YISSGSSTIHYADTVKG (SEQ ID NO: 8)
CDR-H3: RHYGSSRYWYFDV (SEQ ID NO: 9)
CDR-L1: KASQDIKSYLS (SEQ ID NO: 10)
CDR-L2: YATSLAG (SEQ ID NO: 11)
CDR-L3: LQYGESPYT (SEQ ID NO: 12)
In another embodiment, the antibody of the invention comprises:
A heavy chain having a sequence chosen among SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21, and
A light chain having a sequence chosen among SEQ ID NO: 22, NO: SEQ ID NO: 23, SEQ ID NO: 24, SEQ ID NO: 25, SEQ ID NO: 26 and SEQ ID NO: 27.

In preferred embodiments, the antibody of the invention corresponds to:
variant 4 of a-NRP1_LEP n° 1 which combines heavy chain of SEQ ID NO. 13 or a sequence sharing at least 80% of sequence identity with the non-CDR regions of SEQ ID No: 13 and light chain of SEQ ID NO: 26 or a sequence sharing at least 80% of sequence identity with the non-CDR regions of SEQ ID No: 26,
variant 6 a-NRP1_LEP n° 1 which combines heavy chain of SEQ ID NO. 14 or a sequence sharing at least 80% of sequence identity with the non-CDR regions of SEQ ID No: 14 and light chain of SEQ ID NO. 23 or a sequence sharing at least 80% of sequence identity with the non-CDR regions of SEQ ID No: 23,
variant 8 a-NRP1_LEP n° 1 which combines heavy chain of SEQ ID NO. 14 or a sequence sharing at least 80% of sequence identity with the non-CDR regions of SEQ ID No: 14 and light chain of SEQ ID NO. 26 or a sequence sharing at least 80% of sequence identity with the non-CDR regions of SEQ ID No: 26.

The invention further concerns an antibody derived from mouse a-NRP1_LEP n° 2 (also called 27H10) and covering its humanized variants; the antibody comprises the sequences CDR-H4, CDR-H5, CDR-H6, CDR-L4, CDR-L5 and CDR-L6 as defined below:

CDR-H4 is represented by the sequence S $X_{30}$ $X_{31}$ M $X_{32}$ (SEQ ID NO: 28)
wherein $X_{30}$=F or Y
$X_{31}$=G, S, Y or A
$X_{32}$=H or S
CDR-H5 is represented by the sequence $X_{333}$ I S $X_{334}$ $X_{35}$ $X_{36}$ S T $X_{37}$ Y Y A D $X_{38}$ V K G (SEQ ID NO: 29)
wherein $X_{33}$=Y or V
$X_{34}$=S or Y
$X_{35}$=S or G
$X_{36}$=S or G
$X_{37}$=I or K
$X_{38}$=T or S
CDR-H6 is represented by the sequence RHYGRSRYWYFDV (SEQ ID NO: 30)
CDR-L4 is represented by the sequence $X_{39}$ A S Q $X_{40}$ $X_{41}$ $X_{42}$ S Y L $X_{43}$ (SEQ ID NO: 31)
wherein $X_{39}$=K or R
$X_{40}$=D or S
$X_{41}$=I or V
$X_{42}$=K or S
$X_{43}$=S or A
CDR-L5 is represented by the sequence $X_{44}$ A $X_{45}$ S $X_{46}$ $X_{47}$ $X_{48}$ (SEQ ID NO: 32)
where $X_{44}$=Y or G
$X_{45}$=T or S
$X_{46}$=L or R
$X_{47}$=A or E
$X_{48}$=D, S or T
CDR-L6 is represented by the sequence $X_{49}$ Q Y G E S $X_{50}$ Y T (SEQ ID NO: 33)
where $X_{49}$=L or Q
$X_{50}$=P or S In preferred embodiments, the antibody of the invention is chosen among the following antibodies:
Antibody a-NRP1_LEP n° 2 comprising the CDR:
CDR-H1: SFGMH (SEQ ID NO. 34, identical to SEQ ID NO: 7)
CDR-H2: YISSGSSTIYYADTVKG (SEQ ID NO: 35)
CDR-H3: RHYGRSRYWYFDV (SEQ ID NO: 36)
CDR-L1: KASQDIKSYLS (SEQ ID NO: 37, identical to SEQ ID NO: 10)
CDR-L2: YATSLAD (SEQ ID NO: 38)
CDR-L3: LQYGESPYT (SEQ ID NO: 39, identical to SEQ ID NO: 12)

In another embodiment, the antibody of the invention comprises:
A heavy chain having a sequence chosen among SEQ ID NO: 40, SEQ ID NO: 41, SEQ ID NO: 42, SEQ ID NO: 43, SEQ ID NO: 44, SEQ ID NO: 45, SEQ ID NO: 46 and SEQ ID NO: 47 or a sequence sharing at least 80% of sequence identity with the non-CDR regions of SEQ ID No: 40-47, and
A light chain having a sequence chosen among SEQ ID NO: 48, SEQ ID NO: 49, SEQ ID NO: 50, SEQ ID NO: 51, SEQ ID NO: 52 and SEQ ID NO: 53 or a sequence sharing at least 80% of sequence identity with the non-CDR regions of SEQ ID NO: 48-53.

"Antibody" as used herein, can be an intact antibody or an antibody fragment.

"Antibody fragments" refers to a portion of an intact antibody, preferably the antigen binding or variable region of the intact antibody. Examples of antibody fragments include Fv, Fab, F(ab')2, Fab', Fd, dAb, dsFv, scFv, sc(Fv)2, CDRs, diabodies and multi-specific antibodies formed from antibodies fragments.

The term "Fab" refers to an antibody monovalent fragment having a molecular weight of about 50,000 and antigen binding activity, and consisting of the VL, VH, CL and CH1 domains.

The term "VH" refers to the variable regions of an immunoglobulin heavy chain of an antibody, including the heavy chains of an Fv, scFv, dsFv, Fab, Fab' or F(ab)' fragment.

The term "VL" refers to the variable regions of an immunoglobulin light chain of an antibody, including the light chains of an Fv, scFv, dsFv, Fab, Fab' or F(ab)' fragment.

The Fv fragment is the N-terminal part of the Fab fragment and consists of the variable portions of one light chain and one heavy chain.

The term "F(ab)'" refers to an antibody bivalent fragment having a molecular weight of about 100,000 and antigen binding activity, which comprises two Fab fragments linked by a disulfide bridge at the hinge region.

The term "Fab'" refers to an antibody fragment having a molecular weight of about 50,000 and antigen binding activity, which is obtained by cutting a disulfide bond of the hinge region of the F(ab')2 fragment.

The term "Fd" refers to an antibody fragment consisting of the VH and CH1 domains.

The term "dAb" refers to a single variable domain antibody, i.e. an antibody fragment which consists of a VH or VL domain.

A single chain Fv ("scFv") polypeptide is a covalently linked VH:VL heterodimer which is usually expressed from a gene fusion including VH and VL encoding genes linked by a peptide-encoding linker.

The term "dsFv" refers to a VH:VL heterodimer stabilized by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a VH domain connected to a VL domain in the same polypeptide chain (VH-VL). By using a linker that is too short to allow pairing between the two domains on the same chain, the domains are forced to pair with the complementarity domains of another chain and create two antigen-binding sites.

The term "chimeric antibody" refers to an antibody in which the constant region, or a portion thereof, is altered, replaced or exchanged, such that the variable region is linked to a constant region of a different species, or belongs to another antibody class or subclass. The term "chimeric antibody" also refers to an antibody in which the variable region, or a portion thereof, is altered, replaced or exchanged, such that the constant region is linked to a variable region of a different species, or belongs to another antibody class or subclass.

Further, the format of the antibody of the invention can be chosen among different subclasses of antibodies depending on the targeted cellular distribution, binding affinity resulting biological activity. In the treatment of cancer, preferred subclasses would generally be IgG1, IgG2 or IgG4. In a preferred embodiment, it is under IgG4 format.

This specific recognition of the glycosaminoglycan modified neuropilin-1 (GAG-modified NRP-1) form is associated with the original properties of this antibody to bind specifically to the peptide sequence corresponding to leptin binding to NRP-1 compared to those previously described: MNRP-1685A anti-NRP-1 antibody inhibiting binding of VEGF to NRP-1 (a-NRP1_VE) and YW64.3 anti-NRP-1 antibody blocking binding of Sema3A to NRP-1 (a-NRP1_SEM).

The anti-NRP-1 antibodies according to the invention are capable of specifically inhibiting the interaction between the NRP-1 receptor and its ligand, leptin. They act on the NRP-1/OBR signaling pathway which is notably involved in cancers and infectious diseases.

The original properties of this new kind of anti-NRP-1 antibodies are described in the experimental part and these data strongly suggest that such antibodies are promising tool for treatment of cancer.

Disclosed is the use of NRP-1 peptide as previously defined in a vaccination strategy in the treatment of diseases implicating glycosaminoglycans and DNA damage response (DDR).

As previously defined, this NRP-1 peptide corresponds to an epitope included in the 3D structure of post-transcriptional modified NRP-1. It is able to activate cells of the adaptative and of the innate immune system, meaning of both inducing anti-NRP-1 antibodies production and to induces cytotoxic immune response.

Disclosed is the use of an anti-NRP-1 antibody generated by vaccination strategy involving a NRP1 peptide of the invention, as previously defined, in a vaccination strategy in the treatment of diseases implicating glycosaminoglycans and DNA damage response (DDR).

In another embodiment, the genotoxic effect of the NRP-1 peptide-based vaccine and its corresponding a-NRP1_LEP antibodies relate to DDR-associated pathologies.

As used herein, "DDR-associated pathologies" can be cancer, inflammatory diseases and infectious diseases.

In human cells, both endogenous sources during normal and abnormal (chronic inflammation) metabolic activities and environmental factors such as the exposition to carcinogens (X-rays, ultraviolet (UV) light, various genotoxic chemicals) and viral infections, can cause DNA damage, an alteration in the chemical structure of DNA, resulting in as many as 1 million individual molecular lesions per cell per day (Tubbs A et al., Cell. 2017, 168(4):644-656; Chatterjee N et al., Environ Mol Mutagen. 2017, 58(5):235-263; Ryan E L et al., Biomolecules, 2016, 6(1):2; Kay J et al., *DNA Repair (Amst).*, 2019, 83:102673).

Many of these lesions can cause different structural damage to the DNA molecule such as apurinic/apyrimidinic (AP) sites (abasic sites), adducts, single-strand breaks (SSBs), double-strand breaks (DSBs), DNA-protein cross-links, and insertion/deletion mismatches leading to cell stress and injury that has been implicated in many disorders (Martin L J., J Neuropathol Exp Neurol., 2008, 67(5):377-87).

The human genome encodes information for the maintenance of genetic stability and to protect its own integrity. DNA Damage Response (DDR) refers to a collection of processes that detect (lesion-specific sensor proteins), signal and correct DNA damage (DNA repair proteins) (Chatterjee N et al., Environ Mol Mutagen. 2017, 58(5):235-263; Martin L J., J Neuropathol Exp Neurol., 2008, 67(5):377-87; Wood R D et al., Mutat Res., 2005, 577(1-2):275-83).

Multiple DNA repair and damage tolerance pathways involve more than 450 DDR proteins participating in the removal and toleration of the lesions, thus allowing cell survival. Such enzymes are often categorized by the type of DNA damage they repair, for example BER (base excision repair) enzymes, nucleotide excision repair (NER) enzymes; mismatch repair (MMR) enzymes; DNA helicases; DNA polymerases, and so on (Giglia-Mari G et al., Cold Spring Harb Perspect Biol., 2011, 3(1):a000745; Wood R D et al., Mutat Res., 2005, 577(1-2):275-83).

Unfortunately, errors may occur. Failure, defect or inactivation of specific DNA repair enzymes can lead to DNA damage accumulation. Thus, the cell can enter one of three possible states: (i) an irreversible state of dormancy, known as senescence, (ii) cell suicide, also known as apoptosis or programmed cell death (iii) unregulated cell division, which can lead to tumor formation (Tubbs A et al., Cell. 2017, 168(4):644-656).

Standard cancer treatment such as chemotherapy that typically includes direct DNA damaging agents causing mutations or genome instability (Van den Boogaard W M C et al., Cancers (Basel)., 2022, 14(3):627) or radiotherapy where ROS reacts with nitrogenous bases and deoxyribose, causing significant oxidative reactions, both destabilizing the DNA double helix, leading to DNA damage (Juan C A et al., Int J Mol Sci., 2021, 22(9):4642).

The invention relates in particular to "DNA repair targeted therapies" corresponding to a-NRP1_LEP antibodies that affect the DNA damage response (DDR) causing deficiency in DNA damage repair in different cancer cell types.

In another embodiment, the antibody of the invention is able to reduce cancer cell metastasis and mobilize anti-tumor immune response by increasing the number of CD4$^+$Foxp3$^-$ T cells and the re-activation of CD8 $^+$ T cells in the tumor by inducing Cytolytic molecules production (Granzyme B and Perforin).

The anti-NRP-1 antibodies of the invention have been developed using a KLH and biotin-streptavidin conjugate vaccines strategies involving an immunogen sequence derived from the leptin-interaction domain of NRP-1 described in WO2017/050793; this immunogen sequences correspond to NRP-1 peptides (N1, N2 and N3) having the following sequence respectively: N1: streptavidin-biotin-EGNKPVLFQGNTNPTDVVVAVFPK (SEQ ID NO: 54), N2: EGNKPVLFQGNTNPTDVVVAVFPK-biotin-streptavidin (SEQ ID NO: 54) and N3: EGNKPVLFQGNTNPTDVVC-KLH (SEQ ID NO: 55). The antibodies of the invention thus specifically recognize NRP-1 peptide (Npep) on glycosylated NRP-1 and GAG-modified NRP-1.

Thus, in a particular aspect, the invention concerns an immunization method using a peptide of comprising sequence SEQ ID NO: 54 coupled to biotin-streptavidin at N-Terminal and C-Terminal, respectively, and SEQ ID NO: 55 coupled to KLH, for the generation of anti-NRP-1 antibody able to inhibit the NRP-1/OBR signaling pathway, characterized in that it specifically binds to an epitope located on leptin recognition domain of the glycosylated but non GAG-modified NRP-1 (≤150 kDa) and the GAG-modified NRP-1 (>150 kDa) protein.

As the NRP-1/OBR complex is expressed on tumor cells and cells of the microenvironment, an antibody able to inhibit the NRP-1/OBR signaling pathway is particularly adapted in the treatment of cancer associated or not to infectious diseases.

As used herein, "tumor cells" means cancer cells, cancer stem cells, circulating cancer cells from liquid and solid tumors.

As used herein, "tumor cells" means cancer cells, cancer stem cells, circulating cancer cells from metastasis and primary tumors.

As used herein, "cells of the microenvironment" mean immunes cells and stromal cells.

As used herein, "immune cells" mean tumor-associated macrophages (TAM), natural killer (NK) cells, neutrophils, mast cells, dendritic cells (DC), CD4 + and CD8 + T cells, and B cells.

As used herein, "stromal cells" mean CAF (cancer associated fibroblast) and CAF precursors (resident fibroblasts and mesenchymal stromal cells).

Also disclosed is the use of anti-NRP-1 antibodies as defined above for cancer treatment.

In particular, these antibodies can be used to treat colon, lung, breast, brain, skin and prostate cancer but can also be useful in the treatment of hematologic cancer as well as for other diseases wherein the inhibition of NRP-1/OBR signaling pathway is beneficial.

In a particular embodiment, the invention concerns the use of an anti-NRP-1 antibody as defined above characterized in its ability to enter into nucleus of the cells and induce DNA damage and/or telomeres shortening.

In a particular embodiment, the invention concerns the use of an anti-NRP-1 antibody as defined above characterized in its ability to enter into nucleus of the cells expressing NRP-1/OBR complex and to induce DNA damages and/or telomeres shortening.

Indeed, herein it is shown that the properties of the antibodies of the invention relies on their ability to enter into nucleus in vitro and in vivo where they induce DNA damages and telomeres shortening (FIGS. 6-12).

As used herein, "inducing DNA damage" means that antibodies are capable of inhibiting DNA repair. As used herein "DNA repair inhibition" mean inhibition of homologous (HR), canonical non-homologous end-joining (c-NHEJ) and alternative non-homologous end-joining (alt-NHEJ) recombination, nucleotide excision repair (NER), base excision repair (BER), mismatch repair (MMR), ribonucleotide excision repair (RER) and ADP-ribose-mediated chromatin modulation.

In a particular embodiment, the invention concerns the use of an antibody that it is able to mobilize in vivo immune response.

In a particular embodiment, the invention concerns the use of an antibody that it is able to increase immune cell infiltration in the tumor microenvironment.

Demonstrated herein is that antibodies of the invention are able to induce anti-tumor response by increasing immune cell infiltration in the tumor micro-environment (FIG. 13).

As used herein, "tumor micro-environment" means the environment of primary tumor and metastasis, including the surrounding blood vessels, immune cells, fibroblasts, signaling molecules and the extracellular matrix. The tumor and the surrounding microenvironment are closely related and interact constantly.

As used herein, "immune cells" means non-cytotoxic and cytotoxic cells. They include tumor-associated macrophages (TAM), natural killer (NK) cells, neutrophils, mast cells, dendritic cells (DC), CD4 + and CD8 + T lymphocyte cells, and B cells. In particular, immune cells encompass cells expressing NRP-1/OBR and able to modulate in vitro and in vivo anti-tumor immune response.

As used herein, "cytotoxic cells" means cells expressing granzyme B and perforin.

Further, the antibodies according to invention allow to inhibit metastasis and modulate immune cells by increasing CD4 + T cells.

As used herein, "CD4 + T lymphocyte cells" means CD4 T Granzyme B negative cells, CD4 T perforin negative cells, cytotoxic CD4 T Granzyme B positive cells and cytotoxic CD4 T perforin positive cells.

As used herein, "CD8+ T cells" means CD8 T Granzyme B negative cells, CD8 T perforin negative cells, cytotoxic CD8 T Granzyme B positive cells and cytotoxic CD8 T perforin positive cells.

In a particular embodiment of the invention, the anti-NRP-1 antibody is used in combination with radiation therapy.

In another particular embodiment of the invention, the anti-NRP-1 antibody is used in combination with at least one agent selected from chemotherapies, and/or an anti-checkpoint inhibitor such as anti-PD1, anti-PDL1, anti-CTLA4, an/or an anti-angiogenic inhibitor such as anti-VEGF, and/or an inhibitor of casein kinase 2 (anti-CK2).

In a particular embodiment of the invention, the anti-NRP-1 antibody is used as a free monoclonal antibody or as antibody drug conjugate (ADC) or as an antibody associated to CAR-cells (anti-NRP-1-CAR cells) which could be CAR-T cells or NK cells or other immune cells.

The antibodies of the invention are administered to patients through an appropriate route which can be chosen among oral, intramuscular, subcutaneous, intravenous, intraperitoneal or local intra-tumoral injections. Compositions are formulated to be compatible with the intended route of administration.

DESCRIPTION OF THE FIGURES

FIG. 1: Expression of NRP-1/OBR complex in cancer and immune cells in various human cancers. Histological sections of different human cancer showing (A) NRP-1/0BR complex nuclear labeling in most tumor cells (thick arrow), cytoplasmic labeling in few tumor cells (thin arrow) and labeling in some stromal cells (*: fibroblasts) in breast cancer tissue (B) NRP-1/0BR complex positive tumor cells, lymphocytes (thin arrow) and macrophages (thick arrow) in lung cancer tissue (C) NRP-1/0BR complex in numerous positive stromal lymphocytes and tumor cells (T: tumor cells) in lung metastasis (D) NRP-1/0BR complex nuclear labeling in most tumor cells (thick arrow), cytoplasmic labeling in few tumor cells (thin arrow) and labeling in some stromal cells (*:macrophages) in colon cancer tissue (E) NRP-1/0BR complex in positive tumor cells and in positive fibroblasts (black arrow) in metastasis from colon cancer.

FIG. 4: The a-NRP1_LEP antibodies of the invention recognize specifically the NRP-1 protein. (A) Representative result of NRP-1 detection (form ≤150 kDa and form exhibiting high molecular weight >150 kDa) by Western-blot following its immunoprecipitation from circulating tumor cells (CTC41.5E) and A549 lung cancer cell line derived protein lysates with the prior art antibody a-NRP1_VE, the human a-NRP1_LEP and the chimeric a-NRP1_LEP antibody of the invention and their respective isotype controls hIgG4 and hIgG1. (B) Representative result of Western-blot analysis showing NRP-1 (form at ≤150 kDa and form exhibiting high molecular weight >150 kDa) detection following its immunoprecipitation from human MDA-MB-231 breast cancer cell line derived protein lysates with the prior art antibodies a-NRP1_VE and a-NRP1_SEM or the mouse and chimeric a-NRP1_LEP antibodies of the invention. Before cell lysis, MDA-MB-231 cells were treated with 10 nM recombinant human leptin for 3h demonstrating the specificity of the a-NRP1_LEP antibodies of the invention to leptin-dependent NRP-1/OBR complex. (C) Representative result of Western-blot analysis showing NRP-1 (form at ≤150 kDa and form exhibiting high molecular weight >150 kDa) detection following NRP-1 immunoprecipitation from human COLO 205 colon cancer cell line derived protein lysates with the prior art antibody a-NRP1_SEM or the chimeric a-NRP1_LEP antibody of the invention. Before cell lysis, COLO 205 cells were treated with 10 nM recombinant human leptin for 3h demonstrating the specificity of the a-NRP1_LEP antibodies of the invention to leptin-dependent NRP-1/OBR complex. (D) Representative result of Western-blot analysis showing NRP-1 (forms exhibiting high molecular weight >150 kDa) detection following OBR immunoprecipitation from human CTC41.4 cells derived protein lysates.

Figure 2:
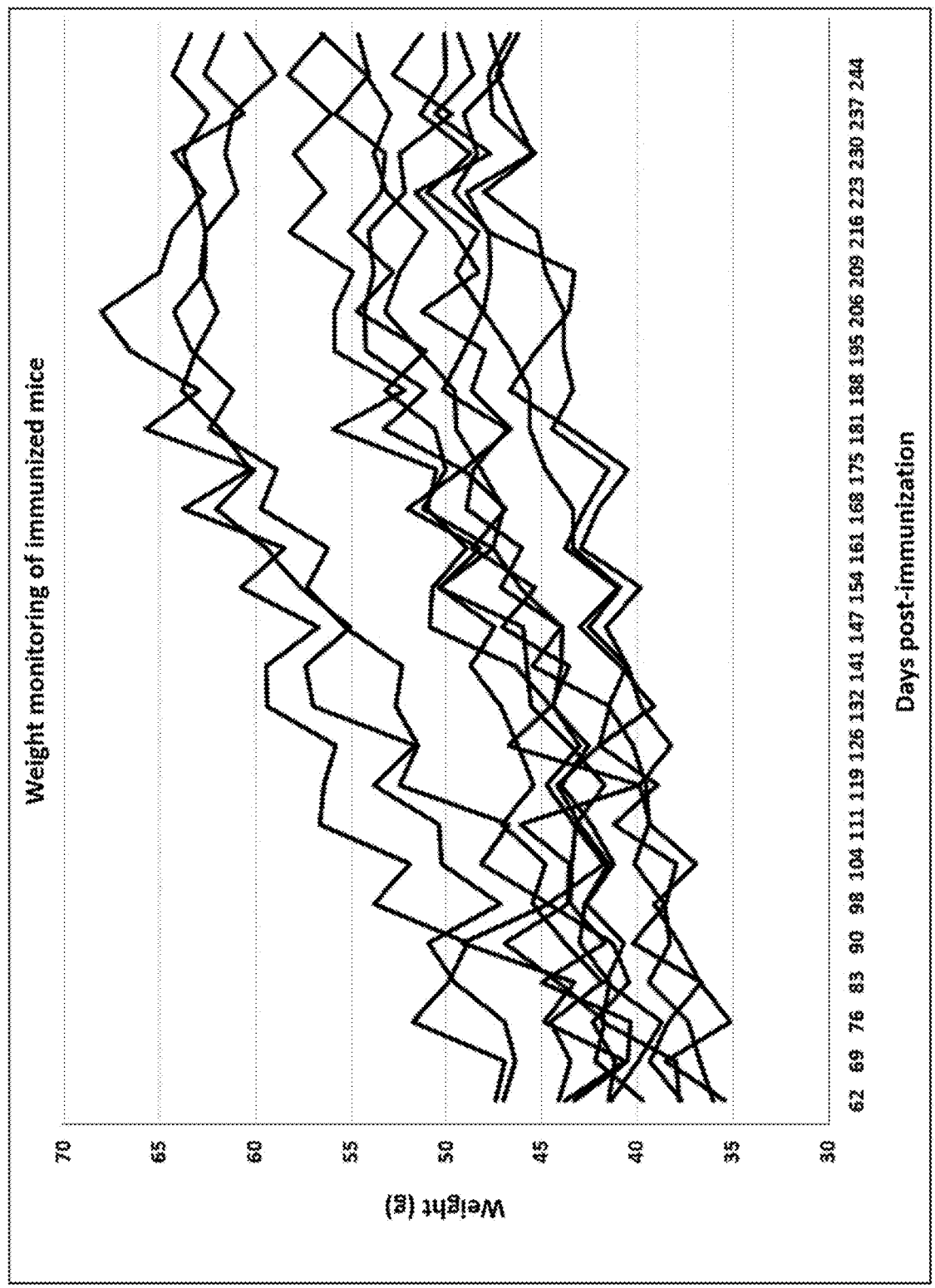
FIG. 2: Representative histogram of weight monitoring of immunized mice with three different immunogenic peptides generated from NRP-1 peptides Npep (N1, N2, N3).

a-NRP1_LEP: antibody of the invention targeting the binding domain of leptin to NRP-1; a-NRP1_SEM: prior art antibody targeting the binding domain of semaphorin to NRP-1; a-NRP1_VE: prior art antibody targeting the binding domain of VEGF to NRP-1; chimeric: form of the mouse antibody of the invention a-NRP1_LEP where human immunoglobulin constant domains has been grafted on the variable domains; CTC: circulating tumor cells; GAG: glycosaminoglycan; hIgG: human immunoglobulin isotype G; IP: immunoprecipitation; KO: knockout; mIgG: mouse immunoglobulin isotype G; mouse: antibody produced in mice; NRP-1: neuropilin-1; OBR: leptin receptor; rh: recombinant human protein; variant: form of the humanized antibody of the invention a-NRP1_LEP; WB: Western-blot.

FIG. 5: The antibodies of the invention, a-NRP1_LEP, bind more specifically the GAG-modified NRP-1 containing chondroitin and heparin sulfate motifs in their epitope compared to the prior art antibodies. (A) Representative flow cytometry histograms of GAG-modified NRP-1 expression by MDA-MB-231 cells treated or not with chrondroitinase using the antibody of the invention a-NRP1_LEP (Chimeric a-NRP1_LEP and variant4 a-NRP1_LEP) compared to the antibodies of prior art (a-NRP1_VE and a-NRP1_SEM). The black curve represents untreated cells and the grey curve represents the chondroitinase-treated cells. (B) Representative result of Western-blot analysis showing NRP-1 (form at ≤150 kDa and form exhibiting high molecular weight >150 kDa) detection following NRP-1 immunoprecipitation from MDA-MB-231 cell derived protein lysates with antibodies. The immunoprecipitated NRP-1 was treated or not with chondroitinase or heparinase in order to remove the potential chondroitin sulfate and heparin sulfate glycosaminoglycans, respectively. (C) Representative result of Western-blot analysis showing NRP-1 (form at ≤150 kDa and form exhibiting high molecular weight >150 kDa) following NRP-1 immunoprecipitation from CTC41 cell derived protein lysates with a humanized variant of the a-NRP1_LEP antibody of the invention. The immunoprecipitated NRP-1 was treated or not with PNGase in order to remove the N-linked oligosaccharides.

a-NRP1_LEP: antibody of the invention targeting the binding domain of leptin to NRP-1; a-NRP1_SEM: prior art antibody targeting the binding domain of semaphorin to NRP-1; a-NRP1_VE: prior art antibody targeting the binding domain of VEGF to NRP-1; chimeric: form of the mouse antibody of the invention a-NRP1_LEP where human immunoglobulin constant domains has been grafted on the variable domains; chondro: chondroitinase; CTC: circulating tumor cells; GAG: glycosaminoglycan; hepa: heparinase; hIgG: human immunoglobulin isotype G; IP: immunoprecipitation; NRP-1: neuropilin-1; variant: form of the humanized antibody of the invention a-NRP1_LEP; WB: Western-blot.

FIG. 6: The anti-NRP-1 antibodies of the invention, a-NRP1_LEP, detection into the cell's nucleus of different cancer types. 6.1 (A-a) Representative fluorescence staining of CTC41.5E cells pre-treated for 72 hours with a mouse or a humanized form of the antibody of the invention, a-NRP1_LEP detected with secondary FITC-coupled antibodies (FITC-anti-mouse IgG and FITC-anti-human IgG) as indicated in light grey. The nucleus was then stained with DAPI (nucleus, dark grey) in order to detect antibodies subcellular localization. 6.1 (A-b) and 6.2 (B-E) Representative result of Western-blot analysis showing mouse or human IgG in cytoplasm and/or nucleus of Circulating tumor cells CTC41.5E (6.1 A-b, 6.2 E) and CTC41 (6.2 D) as well as of human prostate cancer cell line PC3 (6.2 B) and mouse breast cancer cell line 4T1 (6.2 C) after immunoprecipitation using protein A and G Sepharose. Cells were beforehand pre-treated for 5 hours with either the prior art antibodies, a-NRP1_VE and a-NRP1_SEM, or with mouse (1B3, 21B10 and 27H10), chimeric and humanized variants of the antibody developed by the applicant, a-NRP1_LEP. Specific nuclear localization of HDAC2 protein is used as a marker of subcellular fractionation efficiency.

a-NRP1_LEP: antibody of the invention targeting the binding domain of leptin to NRP-1; a-NRP1_SEM: prior art antibody targeting the binding domain of semaphorin to NRP-1; a-NRP1_VE: prior art antibody targeting the binding domain of VEGF to NRP-1; chimeric: form of the mouse antibody of the invention a-NRP1_LEP where mouse immunoglobulin constant domains where replaced with those of human; C: cytoplasm; CTC: circulating tumor cells; DAPI: 4',6-diamidino-2-phenylindole; GAG: glycosaminoglycan; HDAC2: histone deacetylase 2; hIgG: human immunoglobulin isotype G; IP: immunoprecipitation; mIgG: mouse immunoglobulin isotype G; mouse: antibody produced in mice; N: nucleus; NRP-1: neuropilin-1; variant: form of the humanized antibody of the invention a-NRP1_LEP.

FIG. 7.1: NRP-1-dependent entry of the antibody of the invention, a-NRP1_LEP, into the nucleus via the NRP-1/OBR complex in tumor cells. (A-a) Representative result of Western-blot analysis of NRP-1 expression in whole cell extract of wild-type and NRP-1-KO A549 cell line using primary rabbit polyclonal antibody anti-NRP-1. (A-b) Representative result of Western-blot analysis of the humanized a-NRP1_LEP antibody in cytoplasm and/or nucleus in wild-type and NRP-1-KO A549 cell line after immunoprecipitation using protein A and G Sepharose. Cells were beforehand pre-treated for 5 hours with a humanized variant of the antibody developed by the applicant, a-NRP1_LEP, or its control isotype hIgg4. Specific nuclear localization of HDAC2 protein is used as a marker of subcellular fractionation efficiency. (B-a) Representative flow cytometry histograms of NRP-1/OBR complex detection by flow PLA-APC analysis performed with commercial rabbit monoclonal anti human NRP-1 and mouse monoclonal anti-OBR antibodies. The dark grey curves represent pre-treated MDA-MB-231 cells with a mouse a-NRP1_LEP antibody of the invention used at 10, 20 and 40 ng/ml for 2 days whereas the light grey curves indicate pre-incubated cells with the corresponding mIgG2b control isotype. (B-b) Representative flow cytometry histograms of APC intensity obtained following PLA experiment performed with commercial NRP-1 and OBR antibodies. The dark grey curves represent pre-treated MDA-MB-231 cells with a mouse a-NRP1_LEP antibody of the invention and the control isotype used at 20 ng/ml for 2 days (positive PLA signal) whereas the light grey curves indicate pre-incubated cells with the prior art a-NRP1_VE antibody and its irrelevant control isotype used at the same concentration (negative PLA signal).

a-NRP1_LEP: antibody of the invention targeting the binding domain of leptin to NRP-1; a-NRP1_VE: prior art antibody targeting the binding domain of VEGF to NRP-1; C: cytoplasm; HDAC2: histone deacetylase 2; hIgG: human immunoglobulin isotype G; KO: knockout; mIgG: mouse immunoglobulin isotype G; mouse: antibody produced in mice; N: nucleus; NRP-1: neuropilin 1; OBR: leptin receptor; PLA: proximity ligation assay; variant: form of the humanized antibody of the invention a-NRP1_LEP; WT: wild-type.

FIG. 7.2: Leptin-dependent induction of NRP-1 and a-NRP1_LEP antibody translocation into the nucleus of CTC41.5E cell line. Representative result of Western-blot analysis showing a-NRP1_LEP or NRP-1 detection in cytoplasm and/or nucleus of CTC41.5E cell line after immunoprecipitation using protein A and G Sepharose. Cells were beforehand serum starved overnight, then treated with 10 µg/ml of var 4 a-NRP1_LEP for 3 h at 37° C. in the presence or absence of Leptin at 10 nM. Specific nuclear localization of HDAC2 protein is used as a marker of subcellular fractionation efficiency.

a-NRP1_LEP: antibody of the invention targeting the binding domain of leptin to NRP-1; C: cytoplasm; HDAC2: histone deacetylase 2; Human IgG: human immunoglobulin isotype G; MW: molecular weight; N: nucleus; NRP-1: neuropilin 1; Prot. A/G Sepharose: mix (1:1) of protein A and protein G Sepharose 4 Fast Flow beads; variant: form of the humanized antibody of the invention a-NRP1_LEP.

Figure 8B:
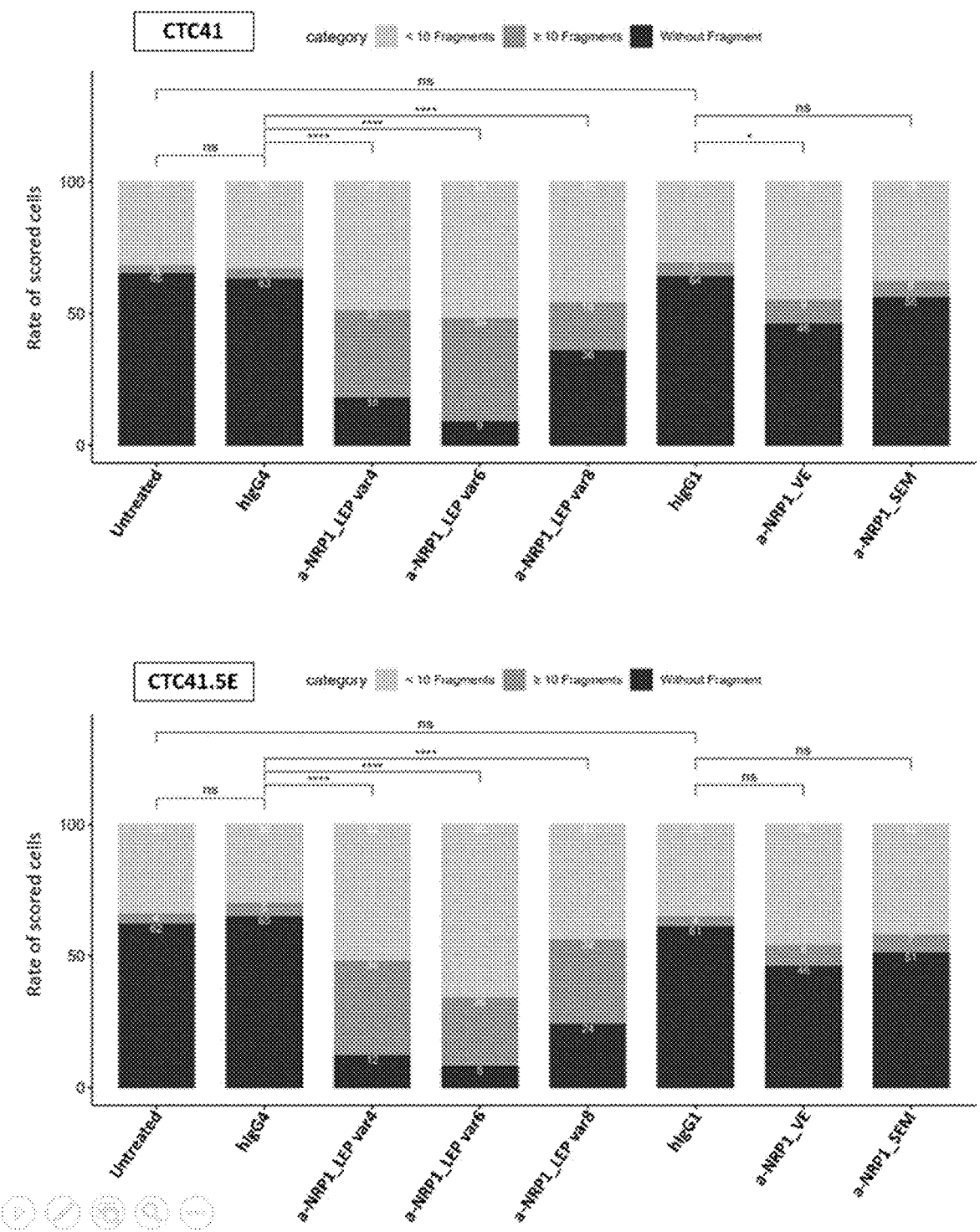
Figure 8D:
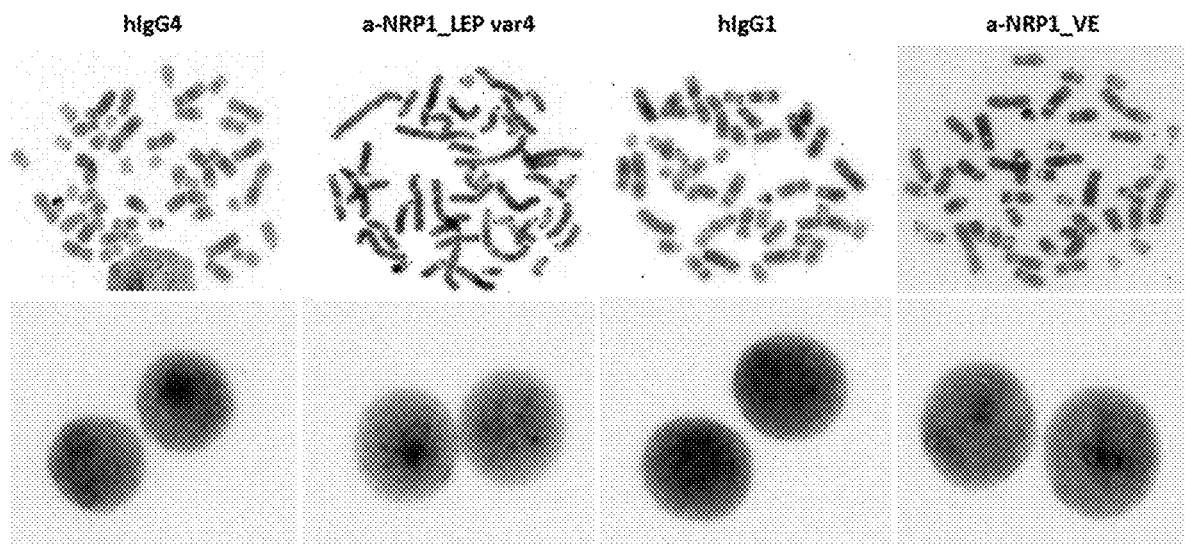

FIG. 8: The antibody of the invention, a-NRP-1-LEP, induces DNA damages and pulverization of chromosomes in circulating tumor cells. (A-a) Representative Cytogenetic detection of DNA damages in CTC41 and CTC41.5E cells pre-treated for 72 hours with control isotypes or a humanized variants of the antibody of the invention a-NRP1_LEP antibody as well as prior art antibodies a-NRP1_VE and a-NRP1_SEM, using telomere and centromere staining followed by M-FISH technique. Karyotypes of CTC41.5E cells obtained by M-FISH reveal normal (mostly in untreated cells) and pulverized (mostly in cells treated with the antibody of the invention) chromosomes. (A-b) Representative fluorescence pictures of CTC41 and CTC41.5E cells at metaphases. Cells were pre-treated as described above (FIG. 8A-a) and then analyzed for telomeres (black dots) and centromere (light grey signal) detection followed by DAPI staining (dark grey signal). Arrows indicate acentric fragments. (B) Quantification of the rate of scored cells (FIG. 8A) with a number of chromosomic fragments (i) higher than 10 (in dark grey) (ii) lower than 10 (in light grey) or (iii) with no fragments (in black). (C-a) Representative phase contrast images of CTC41.5E cells pre-treated as described above (FIGS. 8A-a and A-b), and then stained with DAPI and anti-IgG-FITC. Arrows indicate micronuclei. (C-b) Quantification of scored micronuclei in CTC41 and CTC41.5E cells after cytokinesis-block micronucleus assay associated with telomere and centromere staining. (D) DNA detection damage using cytokinesis-block micronucleus assay followed by telomere and centromere staining in lymphocytes treated with a-NRP1_LEP var 4, a-NRP1_VE and their respective controls hIgG4 and hIgG1. Cells were treated during 72h and Cytochalasin B was added 24h before harvesting cells. Chromosomal aberrations analysis in treated lymphocytes with a-NRP1_LEP var 4, a-NRP1_VE and their respective controls hIgG4 and hIgG1 using telomere and centromere staining. Cells were treated during 72h and colcemid was added 2h before cells harvesting.

a-NRP1_LEP: antibody of the invention targeting the binding domain of leptin to NRP-1; CTC: circulating tumor cells; hIgG: human immunoglobulin isotype G; MN: micronuclei; NRP-1: neuropilin-1; variant: form of the humanized antibody of the invention a-NRP1_LEP.

Figure 9:
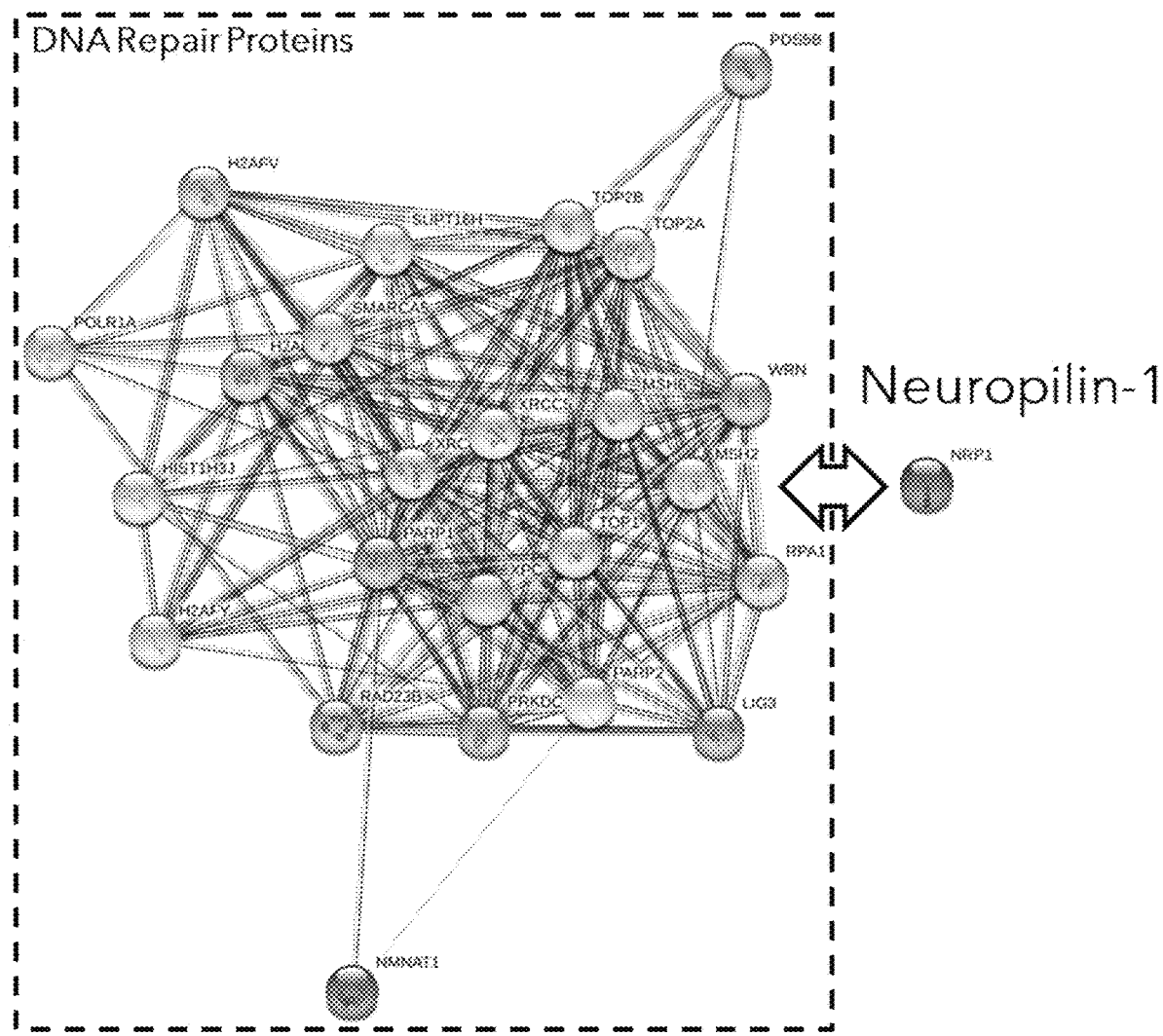

FIG. 9: STRING: functional protein association networks. NRP-1 interactome with a variety of DNA repair proteins immunoprecipitated from whole cell extract of CTC41.5E and A549 WT cell lines with the a-NRP1_LEP antibody of the invention and detected by LC-MS/MS. All gene names mentioned in FIG. 9 are well defined in table 5.

Figure 10:
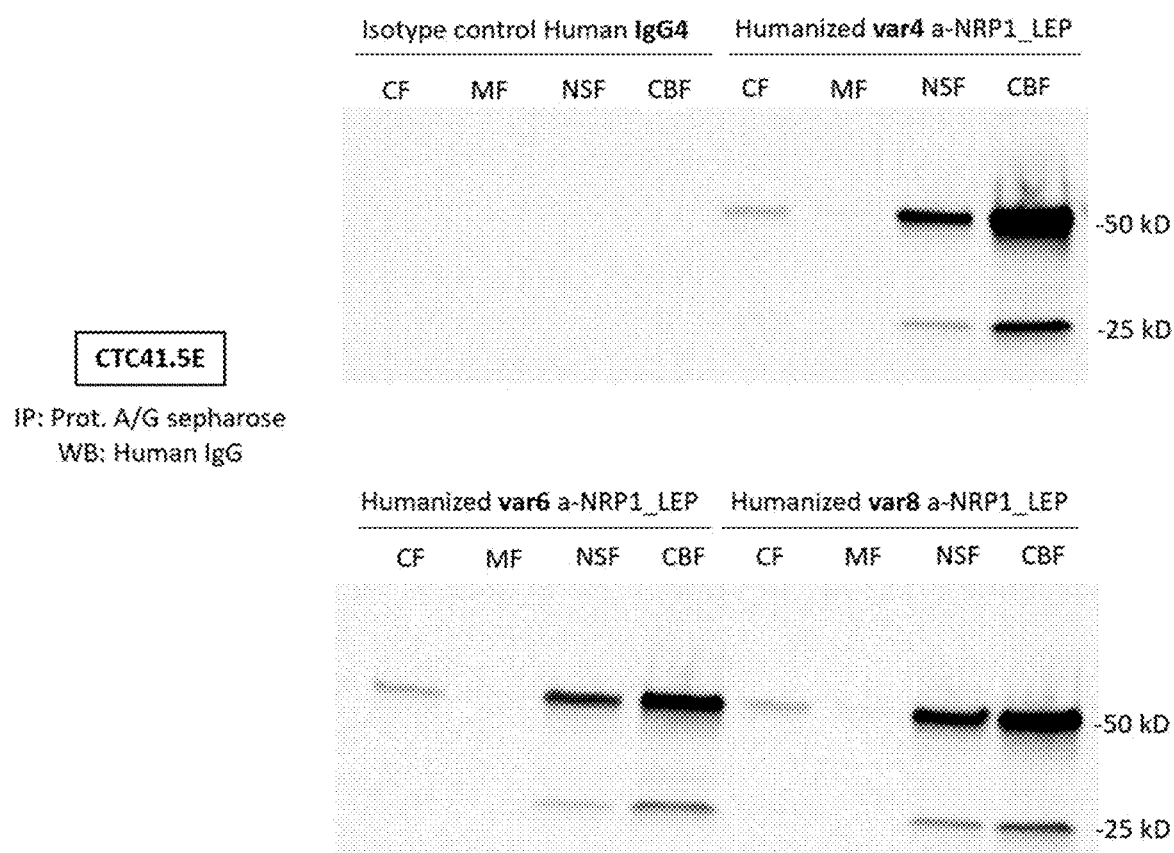

FIG. 10: The anti-NRP-1 antibodies of the invention, a-NRP1_LEP, binds to the chromatin of CTC cells. Representative result of Western-blot analysis showing Humanized variants of a-NRP1_LEP antibody (var4, var6 and var8) bound to the chromatin of circulating tumor cells CTC41.5E after immunoprecipitation using only protein A and G Sepharose. Cells were beforehand pre-treated for 24 hours with either the humanized variants of a-NRP1_LEP antibody or their isotype control Human IgG4.

a-NRP1_LEP: antibody of the invention targeting the binding domain of leptin to NRP-1; CTC: circulating tumor cells; CBF: chromatin bound fraction; CF: cytoplasmic fraction; hIgG: human immunoglobulin isotype G; IP: immunoprecipitation; MF: membrane fraction; NRP-1: neuropilin-1; NSF: nuclear soluble fraction; variant: form of the humanized antibody of the invention a-NRP1_LEP; WB: Western-blot.

Figure 11A:
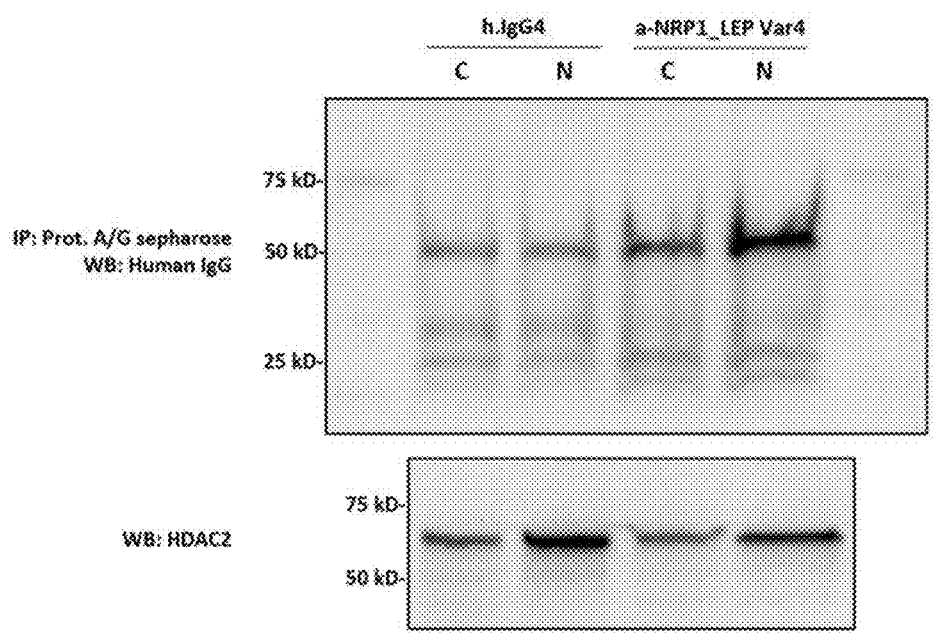

FIG. 11: The anti-NRP-1 antibodies of the invention, a-NRP1_LEP, detection into the nucleus of subcutaneously xenografted CTC cells in SCID mice. A. Representative result of Western-blot analysis showing humanized a-NRP1_LEP into the nucleus of CTC cells collected from mice tumors, after immunoprecipitation using protein A and G Sepharose. Mice were beforehand treated with either humanized a-NRP1_LEP Variant 4 antibody or its isotype control human IgG4 (hIgG4) by intravenously tail injections once a week for a total of five injections. B. Representative fluorescence staining of tumor section of subcutaneously xenografted CTC41.5E cells in SCID mice treated either with humanized a-NRP1_LEP antibody or its isotype control human IgG4 (hIgG4), detected with secondary FITC-coupled antibodies (FITC-anti-human IgG) as indicated in light grey. The nucleus was then stained with DAPI (nucleus, dark grey) in order to detect antibodies subcellular localization.

a-NRP1_LEP: antibody of the invention targeting the binding domain of leptin to NRP-1; C: cytoplasm; CTC: circulating tumor cells; DAPI: 4',6-diamidino-2-phenylindole, FITC: Fluorescein isothiocyanate; HDAC2: histone deacetylase 2; hIgG: human immunoglobulin isotype G; IP: immunoprecipitation; N: nucleus; NRP-1: neuropilin-1;

Prot. A/G Sepharose: mix (1:1) of protein A and protein G Sepharose 4 Fast Flow beads; SCID: Severe combined immunodeficiency; variant: form of the humanized antibody of the invention a-NRP1_LEP.

Figure 12:
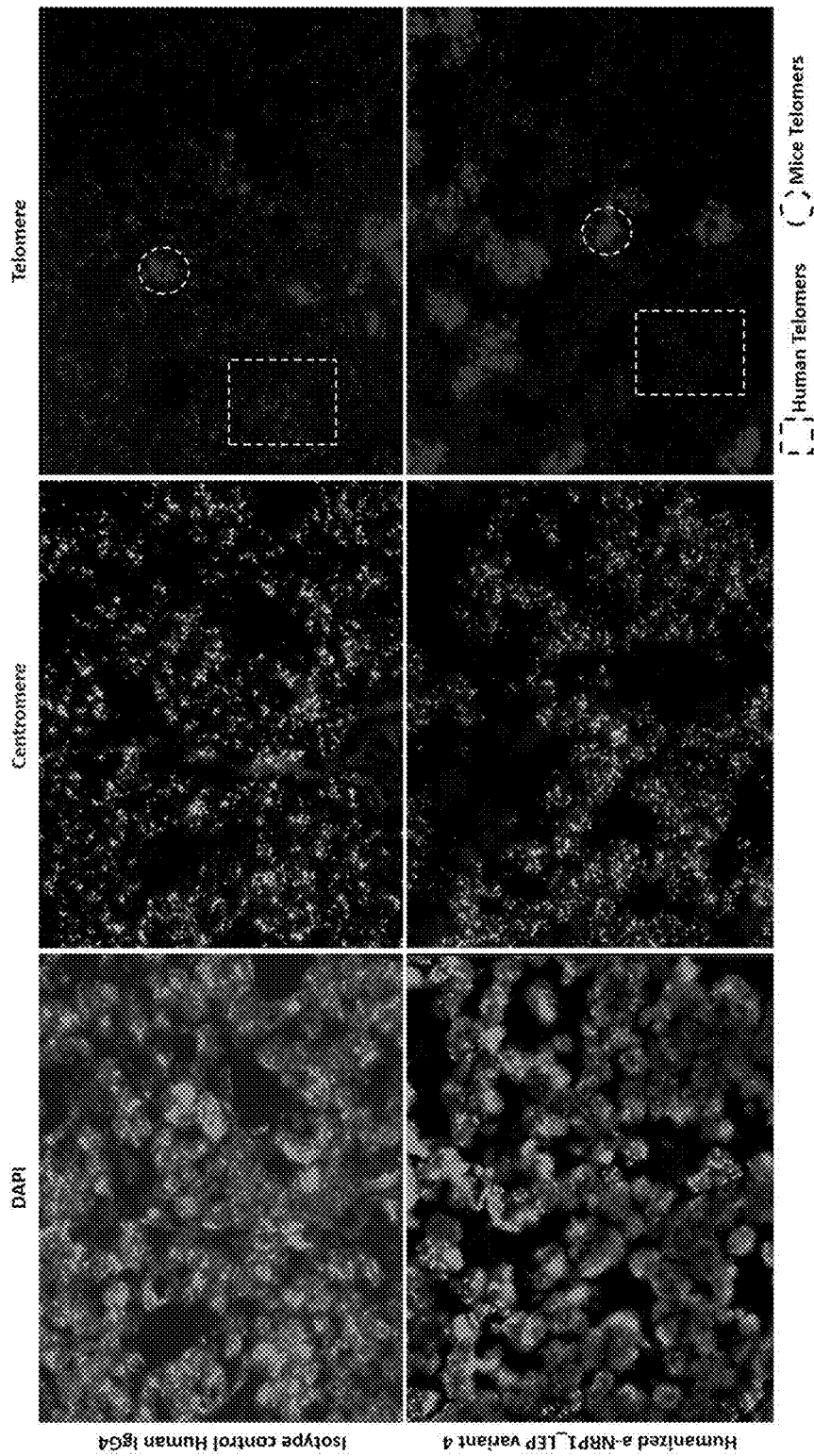

FIG. 12: The antibody of the invention, a-NRP-1-LEP, induces telomere shortening in subcutaneously xenografted CTC cells in SCID mice. Representative result of telomere and centromere staining on 5 μm tumor frozen sections collected from subcutaneously xenografted CTC cells in SCID mice. Mice were beforehand treated with either humanized a-NRP1_LEP Variant 4 antibody or its isotype control human IgG4 (hIgG4) by intravenously tail injections once a week for a total of five injections.

a-NRP1_LEP: antibody of the invention targeting the binding domain of leptin to NRP-1; CTC: circulating tumor cells; SCID: Severe combined immunodeficiency; variant: form of the humanized antibody of the invention a-NRP1_LEP.

FIG. 13: In vivo effect of a mouse a-NRP1_LEP antibody of the invention on lung metastasis derived from primary tumor of 4T1 mouse breast cancer cell line grafted orthotopically in syngeneic BALB/c mice. (A) Representative lung histology (HES staining). (B) Histograms representing quantification of CD4$^+$Foxp3$^-$ cells/mm 2 in lungs metastasis. Values are means±SEM of PBS group (6 mice), mIgG2b group (9 mouse) and mouse a-NRP1_LEP group (11 mice). (C) Correlation between CD4 $^+$Foxp3$^-$ cells density and metastasis size in lungs. (D) Representative areas of CD8 $^+$GRB$^+$ and CD4 $^+$Foxp3$^-$ (CD4 $^+$) staining in lung metastasis of mouse treated with PBS or isotype control IgG2b compared to the antibody of the invention a-NRP1_LEP. Zoomed area of the Murine a-NRP1_LEP treated mouse represents a cluster of activated CD8 $^+$GRB$^+$ and CD4 $^+$Foxp3$^-$ as indicated by their cell-cell interaction (black arrows). a-NRP1_LEP: antibody of the invention targeting the binding domain of leptin to NRP-1; CD: cluster of differentiation; Foxp3: forkhead box P3; HES: hematoxylin and eosin staining; mIgG: mouse immunoglobulin isotype G; mouse: antibody produced in mice; PBS: phosphate-buffered saline; R2: coefficient of determination. *: $p<0.05$, **: $p<0.01$ (one-way ANOVA).

Experimental Part

I—Materials and Methods

The a-NRP1_LEP antibodies of the invention are produced by the CRO Biotem (https://www.biotem.fr/) and the TAB-264 (a-NRP1_VE) and the YW64.3 (a-NRP1_SEM) were purchased from Creative Biolabs (https://www.creative-biolabs.com/).

Generation of mouse a-NRP1_LEP antibodies

OF1 female mice (Charles River) were immunized subcutaneously and intraperitoneally with three different immunogenic peptides generated from Npep (EGNKPVLFQGNTNPTDVVVAVFPK) (SEQ ID NO: 54)) of NRP-1 protein, N1: Streptavidin-EGNKPVLFQGNTNPTDVVVAVFPK (SEQ ID NO: 54), N2: EGNKPVLFQGNTNPTDVVVAVFPK(SEQ ID NO: 54)-Streptavidin and N3: EGNKPVLFQGNTNPTDVVC-KLH (SEQ ID NO: 55). Before streptavidin conjugation, the N1 and N2 were first biotinylated at N-terminal and C-terminal respectively. The N3 peptide sequence of NRP-1 was first modified in C-ter by replacing the last six amino acids by a cytosine for conjugation with a Keyhole Limpet Hemocyanin (KLH). For each immunogenic peptide mice were injected with either high dose (50 μg) or low dose (20 μg) contained in Freund's Complete Adjuvant. Mice were boosted intraperitoneally two times with immunogenic peptide contained in Freund's Incomplete Adjuvant at day 22 and 42. Regarding leptin function in energy balance and its dysfunction implication in obesity, mice were weighted once a week in order to follow the phenotype effect of the immunization as an indicator of neutralizing antibody production. At day 52, anti-NRP-1 antibodies (a-NRP1_LEP) production in immunized mice were analyzed by ELISA as described below. The anti-NRP-1 (a-NRP1_LEP) neutralizing antibodies of leptin signaling were selected on the basis of two main criteria: (i) obese phenotype and (ii) the ability to recognize human and mouse NRP-1 that was validated by ELISA positive signal for recombinant NRP-1 corresponding to the extracellular domain and their binding to human and mouse cells surface expressing native membrane NRP-1 protein detected by flow cytometry analysis. Some of the mice presenting the cited criteria were boosted intravenously with the antigen (N3 peptide) injection at high dose (10 μg) or low dose (5 μg) without any adjuvant after or not intraperitoneal fourth immunization. The selected mice were sacrificed and hybridoma were generated under classical procedure with PEG in a ratio 1:5 myeloma:Lymphocyte. Hybridoma were then plated on 96 well plates before cell culture supernatant screening for reactivity and isotyping by ELISA.

ELISA used for anti-NRP-1 (a-NRP1_LEP) antibodies screening either on mice's serum or on hybridoma cell culture supernatant was based on antigen binding detection performed for recombinant human NRP-1 (3870-N1-025, Bio-Techne), recombinant murine NRP-1 (5994-N1-050, Bio-Techne) and NRP-1 peptides (contains the targeted peptide sequence of NRP-1), Npep and unconjugated N3 (KLH-free) and only clones positively reacting in the three tests were selected (Table 1) and compared to prior art antibodies which by contrast only react to murine and human NRP-1 and not NRP-1 peptides (Npep and unconjugated N3). Culture medium, non-immune serum derived from non-immunized OF1 mice and NRP-1 negative cancer cells were used as a negative control.

Mouse antibodies 21B10 and 27H10 were selected for further studies and engineering steps referenced as a-NRP1_LEP n° 1 and a-NRP1_LEP n° 2 respectively.

a-NRP1_LEP antibodies chimerization and humanization

Selected a-NRP1_LEP monoclonal antibodies were produced as recombinant chimeric antibodies by standard procedure. cDNAs were prepared from high quality RNA extraction from hybridoma by using hifi-reverse transcriptase (SuperScript™ IV, Invitrogen). Specific cDNA coding the antibody variable regions were amplified by using High-fidelity PCR with Q5® High-Fidelity DNA Polymerase (NEB) and degenerated primers (primers kits specifically designed and improved by Biotem). The resulting PCR products were directly sequenced. Sequences encoding the variable domain of heavy chain (VH) and the variable domain of light chain (VL) were then optimized in codons for expression in mammalian cells and synthesized. The corresponding synthetic genes were cloned into Biotem's proprietary vector system that contains the human constant region of either IgG1, IgG1-silent or IgG4 heavy chain or human constant region of kappa light chain. Once validated by sequencing, vectors were amplified for the preparation of low-endotoxin plasmid DNA, which was again verified by sequencing.

Chimeric antibodies were produced by transient expression in CHO DG44 cells over 15 days. The supernatants were harvested and antibody titer was measured by bilayer interferometry using Protein A biosensors on a BLITZ system (Pall ForteBio) and estimated based on a human IgG1 standard.

The supernatants were then purified by protein A affinity chromatography (Purolite Praesto Jetted A50). After dialysis in PBS pH7.4, the total protein concentration was determined by spectrophotometric reading at 280 nm (Eppendorf Biospectrometer).

Mouse antibodies were humanized by grafting the three CDRs (using Kabat and IMGT nomenclatures) from the light chain variable region (VL) into a selected human germline VL close to the mouse antibody VL. Similarly, the three CDRs from the heavy chain variable region (VH) were grafted into a selected human germline VH close to the mouse antibody VH. Furthermore, some amino acid residues in the framework regions (FRs) of the selected human germline variable regions were reverted (back-mutation) to their corresponding mouse amino acid residues. Based upon information harvested on the structure of immunoglobulin variable regions, and with the guidance of a molecular model of the mAb (VH and VL), these few residues in the FRs were identified as having potential key roles in maintaining the CDRs conformation, or as playing a role in the interface between the variable regions of the heavy chain and the light chain. VL and VH are two domains that interact without forming a covalent bond. The residues involved in this interaction must also be maintained, or the paratope might be modified and the antibody affinity altered. They were thus retained in the humanized version V1 ("low risk") or mutated with their human germline amino-acid counterparts in the humanized version V2. Using molecular model, some CDR residues were also substituted for their human germline counterparts in the humanized versions V2. Here, the combination of a structural model with pure sequence analysis allowed discriminating potentially between real paratope-facing and non-paratopic residues in the CDR regions. In addition, the structural models permit to drive the choices regarding back-mutations in light of the selected germline backbones used, allowing a faster humanization process. The humanized versions V1 provided for both VH and VL were conservative versions that aim to avoid (or strongly minimized) alteration of the paratope. These versions were expected to give a similar binding/potency activity as the chimeric antibody used as the reference molecule. The humanized versions V2 for both VH and VL are designed to reach a percentage of sequence identity with the closest human germline of at least 85% (Germinality index as described in Pelat et al [J Mol Biol 2008]. For the design of CDR-grafted versions of the mouse VH (mouse a-NRP1_LEP n° 1 and mouse a-NRP1_LEP n° 2), three human germlines, can be selected according to a high sequence identity across the whole V-gene or because they are widely used germline sequences for human antibody production (according to IMGT/GeneFrequency database) and have other interesting features and provide the possibility of grafting the CDRs in a different molecular environment. For the design of CDR-grafted versions of the a-NRP1_LEP n° 1 and a-NRP1_LEP n° 2 mouse $VL_\kappa$, two human germlines were selected since the homology was high enough. The first step of the humanization process should be to select the best heavy and light chain pairing between the humanized VH and humanized VL versions: (i) For the VH, humanization was performed using 3 different human germlines with 2 versions for each (V1 and V2), driving to a total of 6 different humanized VH. (ii) For the VL, humanization was performed using 2 different human germlines with 2 versions for each (V1 and V2), driving to a total of 2 different humanized VL. At the end, we produced transiently in HEK cell and purified a total of 6 (HC)×4 (LC)=24 monoclonal antibodies and tested them for maintaining the binding capacity to NRP-1 but also for other properties such production efficiency, aggregation tendency or functional activities.

Protein Lysate Preparation from Cancer Cells

After 2 washings with ice cold PBS, seeded or in suspension cells were harvested on ice with 20 mM Tris pH7, 0.1 M NaCl, 10 mM $Na_4P_2O_7$, 1% Triton X-100, 1% protease and phosphatase inhibitor cocktail (1861281, Thermo Scientific), then incubated on ice for 30 min with 20 sec of vortex every 15 min, and then centrifugated for 10 min at 4400 rpm, at 4° C. The protein lysates were collected for protein concentration quantification (BCA kit, Therma scientific) prior immunoprecipitation followed by Western-blot analysis.

For some experiments, the human breast cancer cell line MDA-MB-231, the human colon cell line COLO 205 and the circulating tumor cells CTC41.5E derived from patient were treated after overnight serum starvation with 10 nM recombinant human leptin (398-LP, R&D Systems) for 3h at 37° C., before protein lysate preparation.

Immunoprecipitation of NRP-1 in protein lysates

100 µg of protein lysate from the MDA-MB-231, COLO 205, CTC41.4 (circulating tumor cells isolated from patient suffering metastatic colon cancer—Origin of the cells: Laboratory of Rare Human Circulating Cells (LCCRH), Saint Eloi Hospital, University Medical Centre, Montpellier France)) and wild-type and NRP-1-K0 A549 (human lung cancer cell line) cells were incubated overnight at 4° C., with a mix (1:1) of protein A and protein G Sepharose 4 Fast Flow beads (17-6002-35, GE Healthcare) and 2 µg of different antibodies of the invention a-NRP1_LEP (mouse, chimeric and humanized variants), as well as prior art antibodies, a-NRP1_VE and a-NRP1_SEM, or their respective isotype controls. To investigate the NRP-1/OBR interaction in CTC41.4 cells, 100 µg of protein lysate was immunoprecipitated as described above with anti-OBR antibody (MAB867, R&D Systems). On the day after, the immunoprecipitated samples were washed three times with PBS, resuspended in 10% Beta-mercaptoethanol 4X Laemmli Sample Buffer (1610747, Bio-Rad), heated for 5 min at 95° C. and then stored at −20° C. or subjected to Western-blot analysis.

For glycosaminoglycans nature identification in the GAG-modified NRP-1, immunoprecipitated samples were treated either by chondroitinase (C2905, Sigma) (25 mU/ml), heparinase I and III (H3917, Sigma) (1.25 mU/ml) or PNGase F (P0708s, New England BioLabs) according to manufacturers' instructions prior western blot analysis.

Western-blot analysis

The immunoprecipitated proteins or whole protein lysates were separated during an electrophoretic migration through acrylamide gel 4-20% (4568095, Biorad) and then transferred on PVDF membranes with the Trans-Blot Turbo Transfer System (1704272, Bio-Rad). After incubation for 45 min with a blocking solution (3% BSA), the membranes were incubated overnight at 4° C. with a primary rabbit polyclonal antibody anti-NRP-1 (in 1% BSA) (a gift from Alex L. Kolodkin, The Johns Hopkins University School of Medicine, Baltimore, USA). The next day, the membranes were washed three times 15 min and then incubated with an HRP-conjugated secondary antibody anti-rabbit immunoglobulin 1/1000 (18-8816-33, Rockland). The chemiluminescent signal was acquired with the ChemiDoc Imaging System (Bio-Rad) following ECL substrate addition (1705060, Biorad).

Single Staining for Flow Cytometry

Adherent cells were detached using non-enzymatic cell dissociation solution (C5914, Sigma). Cells (adherent or in suspension) were washed with 2% FBS in PBS and then incubated with anti-NRP-1 unconjugated antibodies of the invention a-NRP1_LEP (mouse, chimeric and humanized variants) or with the unconjugated antibodies of prior art (a-NRP1_VE and a-NRP1_SEM). For the unconjugated antibodies detection, specific secondary antibodies were then added. After a final wash, fluorescence, size and granularity of cells were measured by the LSR Fortessa cytometer (BD Biosciences) and data were analyzed using FlowJo software. A commercial anti-NRP-1 conjugated to PE-Vio 770 (130-111-895, Miltenyi) was used as a positive control.

Proximity Ligation Assay (PLA)

For the validation of the a-NRP1_LEP recognition of the cellular native NRP-1 protein, we proceeded to antibodies proximity ligation assay. The MDA-MB-231 cells were detached using a non-enzymatic cell dissociation solution (C5914, Sigma). 1.5 million cells per condition were washed, fixed, permeabilized and blocked using the transcription factor buffer set (562574, BD Biosciences) and then incubated with a mixture of the commercial anti-NRP-1 antibody that binds specifically to the C-terminal domain of NRP-1 (NBP2-67539, Novus) and the antibody of the invention (mouse a-NRP1_LEP), for 1 h at 37° C. The different PLA steps (incubation with probes, ligation, amplification and detection) were performed using the DUOLINK® flow-PLA Detection Kit (DUO94004, Sigma) according to manufacturers' instructions. The PLA positive signal (FarRed) was detected by the LSR Fortessa cytometer (BD Biosciences). As a negative control for the PLA, cells were incubated only with the commercial anti-NRP-1 antibody.

To analyze the a-NRP1_LEP antibody effect on the NRP-1/OBR complex formation, the MDA-MB-231 cells were cultured for two days in human serum (H4522, Sigma) and then treated for two additional days with the mouse a-NRP1_LEP antibody of the invention or its mIgG2b isotype control at 10, 20 or 40 µg/ml, or with the antibody of the prior art a-NRP1_VE and its hIgG1 isotype control at 20 µg/ml. After washes, fixation, permeabilization and blocking, cells were incubated with commercial anti-NRP-1 (NBP2-67539, Novus) and anti-OBR (AF389, R&D Systems) antibodies at 10 µg/ml for 1 h at 37° C. As a negative control for the PLA, cells were incubated only with the commercial anti-NRP-1 antibody. The PLA positive signal (FarRed) was detected by the LSR Fortessa cytometer (BD Biosciences).

Chondroitin sulfate modified-NRP-1 detection by Flow cytometry

Chondroitinase (C2905, Sigma) was reconstituted in a 0.01% BSA aqueous solution. The MDA-MB-231 cells were treated with chondroitinase (1U/ml) for 2 hours at 37° C. The cells were detached using cell dissociation solution non-enzymatic (C5914, Sigma). 300 000 cells per condition were washed with 2% FBS in PBS and then incubated with different antibodies of interest or their respective isotype controls at 40 µg/ml for 30 min at 4° C. After wash, an Alexa 488-conjugated anti-human immunoglobulin antibody (20022-1, Biotium) was added at 10 µg/ml for 30 min at 4° C. After a final wash, fluorescence, size and granularity of cells were measured by the LSR Fortessa cytometer (BD Biosciences).

Subcellular Fractionation: Cytoplasmic, membrane, nuclear soluble, chromatin-bound and cytoskeletal protein separation The wild-type (ab259777, Abcam) and NRP-1-KO A549 cell line (ab269507, Abcam), the mouse breast cancer cell line 4T1 (purchased from ATCC), the human prostate cancer cell line PC3 (generous gift from Dr. Christophe Deroanne, Laboratory of Connective Tissues Biology, University of Liege, Belgium), and the circulating tumor cells CTC41/41.5E (purchased from Dr. Catherine Panabieres, Laboratory of Rare Human Circulating Cells, Saint-Eloi Hospital, University Medical Centre, Montpellier France) were cultured in human serum and treated with 10 µg/ml of the following antibodies: mouse (a-NRP1_LEP 1B3, 21B10 and 27H10) and 3 different humanized variants of the antibody of the invention a-NRP1_LEP (Var4, Var6 and Var8), and prior art antibodies, a-NRP1_VE and a-NRP1_SEM, as well as their respective irrelevant isotype control, mIgG2b (mouse a-NRP1_LEP), hIgG4 (humanized a-NRP1_LEP) and hIgG1 (prior art antibodies) for 5 h at 37° C. Adherent cells were harvested by scraping. Adherent and suspension cells were both collected by centrifugation at 500 g for 5 minutes and were washed 3 times by suspending the cell pellet with ice-cold PBS. Cytoplasmic and nuclear protein fraction were prepared using NE-PER Nuclear and Cytoplasmic Extraction Reagents (78833) or using Subcellular Protein Fractionation Kit for Cultured Cells (78840, Thermo scientific) according to manufacturers' instructions.

To verify extracts purity (contamination between nuclear and cytoplasmic fractions), 30 µg of each protein fraction were separated by Western-blot and the membranes were incubated overnight at 4° C. with an anti-HDAC2 antibody (05-814, Millipore) specific to nuclear HDAC2 protein.

To determine the antibodies cellular localization, a mix (1:1) of protein A and protein G Sepharose 4 Fast Flow beads was added to both cytoplasmic and nuclear protein fractions. Samples were incubated on orbital rotator mixer for 2 h at room temperature. The immunoprecipitated samples were washed and then subjected to Western-blot analysis using either anti-human IgG-HRP 1/2000 (A18805, ThermoFisher) or anti-mouse IgG-HRP 1/8000 (1030-05, SouthernBiotech) antibodies.

Leptin and NRP-1-dependent translocation of a-NRP1_LEP into the nucleus of CTC41.5E cell line Circulating tumor cells CTC41.5E were serum starved overnight, then treated with 10 µg/ml of a-NRP1_LEP antibody (variant 4) for 3 h at 37° C. in the presence or absence of Leptin at 10 nM. The cytoplasmic and nuclear fractions were prepared as cited above.

NRP-1 and a-NRP1_LEP antibody complex was immunoprecipitated by adding a mix (1:1) of protein A and protein G Sepharose 4 Fast Flow beads to both cytoplasmic and nuclear protein fractions. Samples were incubated on orbital rotator mixer for 2 h at RT. The immunoprecipitated samples were washed and then subjected to Western-blot analysis using either anti-human IgG-HRP (A18805, ThermoFisher) to detect the a-NRP1_LEP antibody or primary rabbit polyclonal antibody anti-NRP-1 followed by an anti-rabbit HRP conjugated antibody.

Nuclear a-NRP1_LEP detection by immunofluorescence microscopy

CTC41.5E cells were incubated with a mouse a-NRP1_LEP and a humanized variant of the a-NRP1_LEP, antibodies of the invention, and their respective control isotypes at 10 µg/ml for 3 days. Cells were centrifugated at 1000 g for 5 min on slides by cytospin and then fixed with ice cold acetone for 5 min. After washing and blocking, cells were incubated with the anti-human IgG-FITC (20022-1, Biotium) or anti-mouse IgG-FITC (A-11029, ThermoFisher) (light grey signal) 1/1000 antibodies for 1 h at 37° C. The slides were counterstained with DAPI (dark grey signal) and mounted in PPD. Immunofluorescence (FIG. 6.1 A-a) were acquired using automated acquisition module Autocapt software (MetaSystems, version 3.9.1) using a ZEISS Plan-Apochromat 63x/1.40 oil and CoolCube 1 Digital High-Resolution CCD Camera.

a-NRP1_LEP antibody DNA damage effect detection by telomere and centromere staining followed by M-FISH technique.

This approach has been used to a reliable and precise characterization of the genotoxic effect of the anti-NRP-1 antibodies of the invention (a-NRP1_LEP) compared to the prior art antibodies (a-NRP1_VE and a-NRP1_SEM) on the CTC cells.

For chromosome preparation and mitotic index quantification, circulating tumor cells (CTC41 and CTC41.5E) were cultured in human serum and treated with the corresponding anti-NRP-1 antibodies as cited above and their respective isotype controls (Mouse IgG2b, human IgG4 and IgG1). 72 h post-treatment, colcemid (100 ng/ml) was added for 2 hours before harvesting and cells in metaphase were prepared following the standard methanol/acetic acid (3/1, v/v) procedure. Treated cells were stored at −20° C. until use.

Briefly, telomeres and centromeres were hybridized with a Cy-3-labelled PNA probe specific for TTAGGG for telomeres and a FITC-labeled probe specific for centromere sequences (Cell Environment, Evry, France), as previously described (M'kacher et al 2014; M'kcaher et al 2015). Briefly, slides were washed with 1×PBS and fixed with 4% formaldehyde at room temperature. After rinsing three times (3×5 min) with PBS, they were treated with pepsin (0.5 mg/ml) at 37° C. for 5 min. After rinsing three times (3×5 min) with PBS, the slides were sequentially dehydrated with 50%, 70%, and 100% ethanol and air-dried. The telomere and centromere probes were added to the slides and subsequently denatured on a hot plate at 80° C. for 3 min and then incubated in the dark for 1 h at room temperature. The slides were subsequently rinsed with 70% formamide/10 mM Tris pH 7.2 two times during 15 min (for 2×15 min) and then in 50 mM Tris pH 7.2/150 mM NaCl/0.05% Tween-20 (3×5 min). After a final rinse in PBS, the slides were counterstained with DAPI and mounted in PPD. After telomere quantification and the automatic capture of metaphases with telomere and centromere staining, same slides were washed with 2X SCC for 30 min at 70° C. and rinsed with 0.1×SSC for 1 min at room temperature then denatured using NaOH and subsequently washed (1 min) with 0.1X SCC and 2×SSC and sequentially dehydrated in 70%, 95%, and 100% ethanol and air-dried. The M-FISH probes (M-FISH 24XCyte, Metasystems, Altlussheim, Germany) were denaturated for 5 min at 75° C., and added to the slides and incubated at 37° C. for two days. The slides were subsequently rinsed with 0.4×SSC for 2 min at 72° C. and then with 2×SSC/0.005% Tween-20. The slides were counterstained with DAPI and mounted in PPD (Kaddour 2017; M'kacher et al 2020).

Chromosomal aberrations were assessed. In all, 100 metaphases were scored per condition. Images of metaphase cells were acquired using automated acquisition module Autocapt software (MetaSystems, version 3.9.1) using a ZEISS Plan-Apochromat 63x/1.40 oil and CoolCube 1 Digital High-Resolution CCD Camera. Settings for exposure and gain remained constant between captures. The analysis was carried out using Isis software (MetaSystems, version 3.9.1) as described previously.

Micronucleus assay

Circulating tumor cells, CTC41 and CTC41.5E were cultured in RPMI 1640 Medium GlutaMAX™ (61/870,036, Gibco) supplemented with human EGF, premium (130-097-749, Miltenyi), human FGF-2, premium (130-093-564, Miltenyi), INSULIN-TRANS-SEL-A (51300044, Gibco) 10% inactivated human serum (H4522, Sigma). Cells were treated with 10 µg/ml of the humanized variants of the antibodies of the invention a-NRP1_LEP (variant 4, 6 and 8) as well with the prior art antibodies a-NRP1_VE and a-NRP1_SEM for 3 days at 37° C. Human IgG4 and IgG1 were used as negative controls. Cytochalasin B (from *Drechslera dematioidea*, Sigma) solution prepared in dimethyl sulphoxide at a concentration of 6 µg/mL was added 24 h before treatment arrest according to standard procedures.

Automatic scoring of micronuclei (MN) was performed using MNScore software (version 3.8.101 MetaSystems, Althaussen, Germany) with a Metafer 4 image analyzer (MetaSystems, Althaussen, Germany) comprised of a Zeiss Axioplan 2 imager to detect MN. An operator validated and excluded the false MN in bi-nucleate cells.

Liquid Chromatography—Mass Spectrometry/Mass Spectrometry (LC-MS/MS) analysis

100 µg of protein lysates from circulating tumor cells CTC41.5E and human lung cancer cells A549 were incubated overnight at 4° C. with a mix (1:1) of protein A and protein G Sepharose 4 Fast Flow beads and 2 µg of the humanized antibody of the invention a-NRP1_LEP (variant 4) or the prior art antibody a-NRP1_VE and their respective isotype controls (human IgG4 and IgG1). Immunoprecipitated proteins by the cited antibodies or their corresponding isotype controls were detected by LC-MS/MS.

Material: MS grade Acetonitrile (ACN), MS grade $H_2O$ and MS grade formic acid (FA) were from ThermoFisher Scientific (Waltham, MA, USA). Sequencing-grade trypsin and Lys-C, Mass Spec Grade was from Promega (Madison, WI, USA). Dithiothreitol (DTT) and iodoacetamide (IAA) were from Sigma-Aldrich.

Samples preparation prior to LC-MS/MS analysis: Beads were subjected overnight at 37° C. to a double enzymatic digestion in 20 µl of 25 mM $NH_4HCO_3$ buffer containing 2 µg of trypsin and Lys-C mixture (1:1) per sample. The resulting peptides were loaded and desalted on evotips provided by Evosep (Odense, Denmark) according to manufacturer's procedure.

LC-MS/MS acquisition: Samples were analyzed on a timsTOF Pro 2 mass spectrometer (Bruker Daltonics, Bremen, Germany) coupled to an Evosep one system (Evosep, Odense, Denmark) operating with the 30SPD method developed by the manufacturer. Briefly, the method is based on a 44-min gradient and a total cycle time of 48 min with a C18 analytical column (0.15×150 mm, 1.9 µm beads, ref EV-1106) equilibrated at room temperature and operated at a flow rate of 500 nl/min. $H_2O$/0.1% FA was used as solvent A and ACN/0.1% FA as solvent B.

The timsTOF Pro 2 was operated in PASEF mode (Meier F; Beck S; Grassl N; Lubeck M; Park M A; Raether O; Mann M Parallel Accumulation-Serial Fragmentation (PASEF): Multiplying Sequencing Speed and Sensitivity by Synchronized Scans in a Trapped Ion Mobility Device. J. Proteome Res. 2015, 14 (12), 5378-5387) over a 1.3 sec cycle time. Mass spectra for MS and MS/MS scans were recorded between 100 and 1700 m/z. Ion mobility was set to 0.75-1.25 V. s/cm$^2$ over a ramp time of 180 ms. Data-dependent acquisition was performed using 10 PASEF MS/MS scans per cycle with a near 100% duty cycle. Low m/z and singly charged ions were excluded from PASEF precursor selection by applying a filter in the m/z and ion mobility space. The dynamic exclusion was activated and set to 0.8 min, a target value of 16000 was specified with an intensity threshold of 1000. Collisional energy was ramped stepwise as a function of ion mobility.

Data analysis: MS raw files were processed using PEAKS Online X (build 1.5, Bioinformatics Solutions Inc.). The data was searched against the Human Uniprot release 2021_03 database consisting of reviewed-only sequences (total entry 20387). Parent mass tolerance was set to 20 ppm, with fragment mass tolerance of 0.05 Da. Specific tryptic cleavage was selected and a maximum of 2 missed cleavages was authorized. For identification, the following post-translational modifications were included: acetyl (Protein N-term), oxidation (M), deamidation (NQ) as variables and half of a disulfide bridge or carbamidomethylation (C) as fixed. Identifications were filtered based on a 1% FDR (False Discovery Rate) threshold at both peptide and protein group levels.

In vivo validation of the humanized anti-NRP-1 antibodies of the invention a-NRP1_LEP ability to enter into the nucleus of subcutaneously xenografted CTC cells in SCID mice and to induce DNA damage.

Eight SCID mice (Jackson Mouse SN 1803 F indiv mice, CBySmn.Cg-Prkdcscid/J, Ho, F, 7 w.o.) were injected subcutaneously with CTC41.5E cells per 100 µl (1:1) medium/Matrigel (Corning #356255) into their right flank. The mice were constantly monitored on tumor growth. When the total tumor burden reached 300 mm$^3$ the mice were treated with an amount of 200 µg of either humanized a-NRP1_LEP Var4 or its isotype control (human IgG4) once a week by intravenous tail injection. At the end of the experiment, tumor samples (primary tumor) and organs (such as lungs and liver) were collected for histological and biochemical analysis. Collected tumors were either, (i) dissociated with the Tumor Dissociation Kit (Miltenyi #130-096-730), resulted tumor cells were lysed using the NE-PER™ Nuclear and Cytoplasmic Extraction Reagents (Thermo #78833) and then the humanized a-NRP1_LEP Variant 4 localization were detected by Western-blot following its immunoprecipitation using only protein A and protein G Sepharose 4 Fast Flow beads mix (1:1), or (ii) placed in plastic molds, covered with a thick layer of Cryomatrix™ frozen embedding medium (Thermo Scientific) and conserved at −80° C. until use. For immunofluorescence analysis, 5 µm sections of samples were cut at −20° C. using CryoStar NX70 Crysotat (Thermo Scientific) and then sections of frozen tissues were mounted on slides and stored at −20° C. until use.

Telomeres and centromeres were stained with a Cy-3-labelled PNA probe specific for TTAGGG for telomeres and a FITC-labeled probe specific for centromere sequences (Cell Environment, Evry, France). Briefly, slides with of 5 µm of tumor sections were fixed with acid acetic/methanol (1v/3v) during 20 min. The slides were dried overnight at room temperature.

After washing with PBS, tumor sections were fixed with 4% formaldehyde at room temperature, rinsed three times with PBS then permeabilized with pepsin (0.5 mg/ml) at 37° C. for 5 min. After additional rinsing three times with PBS, the tumor sections were sequentially dehydrated with 50%, 70%, and 100% ethanol and air-dried. The telomere and centromere probes were added to the tumor sections and subsequently denatured on a hot plate at for 3 min and then incubated in the dark for 1 h at room temperature. The slides were subsequently rinsed with 70% formamide/10 mM Tris pH 7.2 three times during 15 min and finally in 50 mM Tris pH7.2/150 mM NaCl pH 7.5/0.05% Tween-20 (3×5 min). After a final rinse in PBS, the tumor sections were counter-stained with DAPI and mounted in PPD at the appropriate pH.

In vivo analysis of mouse a-NRP1_LEP antibody effect on metastasis and immune system using a high metastatic breast cancer cell line 4T1 in an orthotopic syngeneic mouse model.

All experimental procedures were approved in 2020 by the French ethic committee for animal experimentation n° 026, in accordance with French and European laws. 5-6-weeks old female BALB/c mice were purchased from Charles River Laboratories (L'Arbresle, France). Mice were housed under SPF conditions with a maximum of five mice/cage and left 1 week for adaptation to the new environment. Then mice were orthotopically grafted with the mouse breast cancer cells 4T1 (50 000 cells/20 µl of PBS) in the third mammary gland (down, at the left side of the mouse). Tumors volume and body weight were measured 3 times/week. Mice were randomized to experimental groups at a stage of lung metastasis appearance when tumors reached an average volume of 150 mm$^3$ and were then treated 3 times (once a week) with PBS, mIgG2b isotype control (InVivoPlus mouse IgG2b isotype control, unknown specificity-Catalog #BP0086) and a mouse a-NRP1_LEP antibody at 2.5 mg/kg (equivalent to 50 µg by a mouse of 20 g average weight) by intravenous (IV) injections. Mice were euthanized 10 days after the last injection and organs were collected and fixed for histology analysis. Histology of lung metastasis and immune system infiltrates Histological analyses were performed by the ISO certified AMMICa PETRA platform at Gustave Roussy institute (ISO 9001:2015). Lungs were fixed in a 4% paraformaldehyde solution (F8775, Sigma) and were then dehydrated and embedded in paraffin. 4 µm thick sections were obtained by cutting samples with a microtome and all samples were then stained with hematoxylin/eosin/safran (HES). Immunohistochemistry staining were performed on lungs sections using the automated instrument Bond RX (Leica). All the samples and slides were anonymized in order that technicians did not know the treatment of mice.

For the detection of the double staining CD4/FOXP3 (Cell Signaling #25229, clone D7D2Z, 1:50/#12653 clone D608R, 1/200) paraffin sections were unmasked by heating in ER2 (EDTA buffer pH9) for 20 min at 100° C. and then the two primary antibodies were successively incubated for 1 h at room temperature. They were detected respectively with the Bond Polymer Refine Red Detection kit (DS9390, Leica Biosystems) and the Bond Polymer Refine Detection kit (DS9800, Leica Biosystems)+HIGHDEF® black IHC chromogen (HRP) kit (ADI-950-171-0030, Enzo Life-sciences). In case of positive signal, a red staining (Fast red) indicates membrane CD4 and a black staining appears for nuclear FOXP3.

For detection of triple markers CD4/CD8/GrB or CD4/CD8/Perf, antigen retrieval was performed by incubating slides in ER2 buffer (pH 9.0) for 20 min at 100° C. Then, the antibodies CD4 (Cell Signaling #25229, clone D7D2Z, 1:50), CD8 (Cell Signaling #98941, clone D4W2Z, 1:400), Granzyme B (Cell Signaling #44153, clone 5EV2L, 1:100) or Perforin (Cell Signaling #31647S, clone E3W4I, 1:100) were successively incubated for 30 min at room temperature, and detected respectively by Polymer anti-rabbit HRP OPAL (Akoya, #NEL830001KT). The signal was revealed with OPAL 480 (Akoya, #FP1500001KT) for CD4, OPAL 570

(Akoya, #FP1488001KT) for CD8 and OPAL 690 (Akoya, #FP1497001KT) for Granzyme B or Perforin. Finally, the sections were counterstained by DAPI (Akoya) and slides were mounted for immunofluorescence scanning with the Vectra POLARIS, Akoya scanner and image analysis.

Scanning of Slides

HES slides were scanned at 20× magnification with Hamamatsu Nanozoomer 2.0-HT C9600-13. CD4 and FoxP3 double stained slides were scanned at 20× magnification with Olympus VS 120.

Staining Detection and Quantification

All slides were processed with QuPath software [Bankhead, P. et al. *QuPath: Open source software for digital pathology image analysis*. Scientific Reports (2017) https://doi.org/10.1038/s41598-017-17204-5]. Quantification process involves 4 steps: region of interest delineation, cell detection, cell classification and, optionally, measurements on cells (e.g. distance to tumor compartment calculation). Automatic selection of regions of interest (whole tissue or tumor regions) was done thanks to classifiers (classifiers were trained by machine learning at recognizing these compartments) and, eventually, manually refined to exclude artefacts or misclassifications.

For CD4/FoxP3 staining, cell detection was performed with Cell detection function and phenotyping was performed with the use of two successive classifiers specialized in the recognition of, respectively, red membrane staining and black nuclear staining. Distances to the tumor edges were computed thanks to the Distance to annotation 2D function. The size of metastasis in lungs was determined manually by a senior pathologist using the Hamamatsu digital pathology NDP.view2 U12388-01 viewing software.

For CD4/CD8/Grb and CD4/CD8/Perf staining, cell detection was performed with Cell detection function and phenotyping was performed with the use of three successive classifiers specialized in the recognition of, Opa1480 staining (CD4), Opa1570 staining (CD8) and Opa1690 staining (GrB or Perf).

Results are expressed, for each phenotype, as densities of stained cells (the number of stained cells of each phenotype per mm 2 of tumor tissue).

Statistical Analyses

Statistical analyses were performed using GraphPad Prism 6 software.

Differences between groups were tested for significance by one-way ANOVA. p-value ≤0.05 was considered statistically significant.

II— Results

EXAMPLE 1: NRP-1 peptide vaccine inducing immune response demonstrated by the production of neutralizing antibodies capable to recognize NRP-1 protein.

In general, the development of antibodies, using peptide sequence that mimic the epitope of the antigen is not used because the generated antibodies do not necessarily recognize the native antigen. It is also difficult to generate antibody to a specific site like a modification or a specific domain when developing monoclonal antibodies (MAbs) with a protein.

Interestingly, while the prior art anti-NRP-1 antibodies (a-NRP1_VE and a-NRP1_SEM) are developed by phage display technology, the antibodies of the invention a-NRP1_LEP are generated by NRP-1 peptides-based vaccine coupled to a carrier protein for mouse immunization, demonstrating thus the therapeutical potential of the NRP-1 peptide (Npep) cancer and infectious diseases vaccines.

EXAMPLE 2: The a-NRP1_LEP antibodies neutralizing NRP-1/OBR complex signaling.

NRP-1 acts as a co-receptor for leptin since a complex of NRP-1 and leptin receptor (OBR) were detected by immunohistochemistry on tissue microarray of different cancer tissues (FIG. 1). The formation of this complex is leptin dependent (Methods and Pharmaceutical Compositions for the Treatment of Diseases Mediated by the NRP-1/OBR Complex Signaling Pathway, WO 2015/124588). Consequently, mice immunized with the peptide sequences of NRP-1 corresponding to leptin binding in order to develop specific neutralizing antibodies that prevent the binding of leptin to NRP-1 thus NRP-1/OBR signaling have shown obese phenotype as a proof of concept (FIG. 2). The selected anti-NRP-1 (a-NRP1_LEP) neutralizing antibodies of leptin signaling based on the two main criteria: (i) obese phenotype and (ii) the ability to recognize human and mouse NRP-1 as validated by ELISA positive signal on recombinant protein as reported FIG. 2 and table 1. All added to their ability to bind native NRP-1 protein of human and mouse cell surface.

TABLE 1

Extract of the screening ELISA for the selection of hybridoma of interest reacting against human and murine recombinant NRP-1 and a synthetic peptide Npep.

| Hybridoma | Absorbance on human NRP-1 (1 µg) | | Absorbance on murine NRP-1 (1 µg) | | Absorbance on NRP-1 peptide (Npep) (1 µg) | | Selected |
|---|---|---|---|---|---|---|---|
| | pure | 1/10 | pure | 1/10 | pure | 1/10 | |
| mouse a-NRP1_LEP 21B10 | 0.452 | 0.11 | 0.275 | 0.155 | 0.1 | 0.139 | X |
| mouse a-NRP1_LEP 21H6 | 0.336 | 0.113 | 0.185 | 0.075 | 0.105 | 0.077 | |
| mouse a-NRP1_LEP 23H8 | 0.26 | 0.14 | 0.152 | 0.082 | 0.111 | 0.09 | |
| mouse a-NRP1_LEP 27H10 | 0.259 | 0.136 | 0.357 | 0.193 | 0.311 | 0.139 | X |

Two mouse a-NRP1_LEP antibodies 21B10 and 27H10 were selected for further studies and engineering steps. They are referenced as a-NRP1_LEP n° 1 and a-NRP1_LEP n° 2 respectively.

EXAMPLE 3: The a-NRP1_LEP antibodies recognize a specific epitope located on the b1 domain of NRP-1 with high specificity to GAG-modified NRP-1 compared to antibodies of prior art.

Figure 3A:
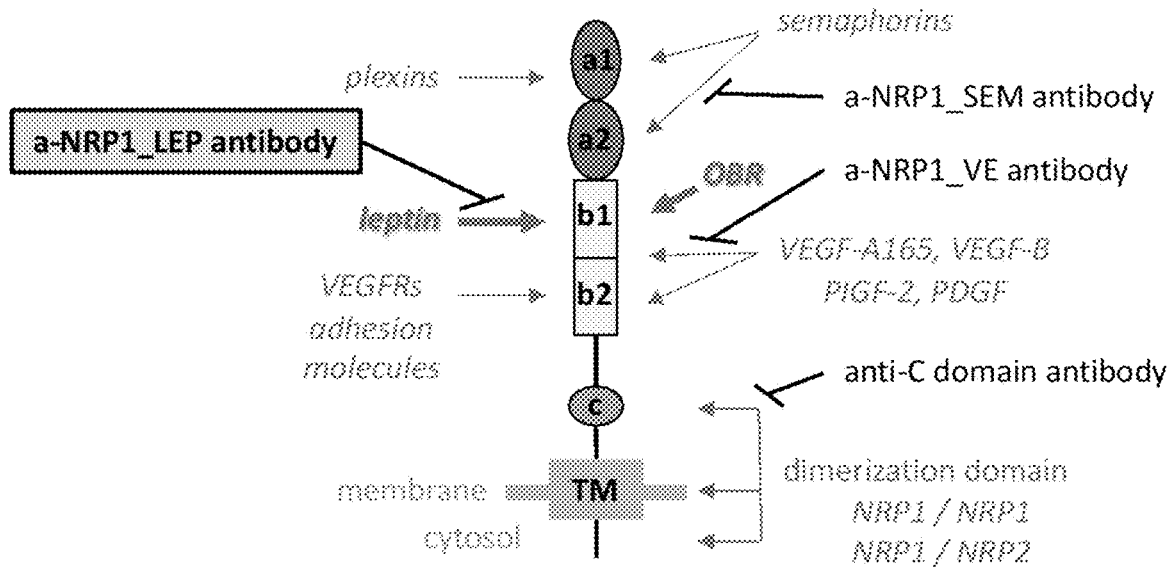
FIG. 3: Schematic representation of NRP-1 structure, its natural ligands and the different classes of mAbs. (A) General drawing of the different domains of NRP-1, its natural ligands are indicated in italic with grey arrows showing their respective binding domains. In black are indicated the different classes of inhibitory antibodies and the frame indicates the class of antibodies of this invention inhibiting the binding of leptin to NRP-1 b1 domain. (B) shows on the crystal structure of MNRP-1685A fab bound with only CDR-H3 and CDR-L1 to its 10 amino acids epitope on b1 domain indicated in grey open circle (PDB: 2QQN). Is also illustrated the peptide Npep dark circle used in the present invention to generate the new class of mAbs (a-NRP1_LEP).
Figure 3B:
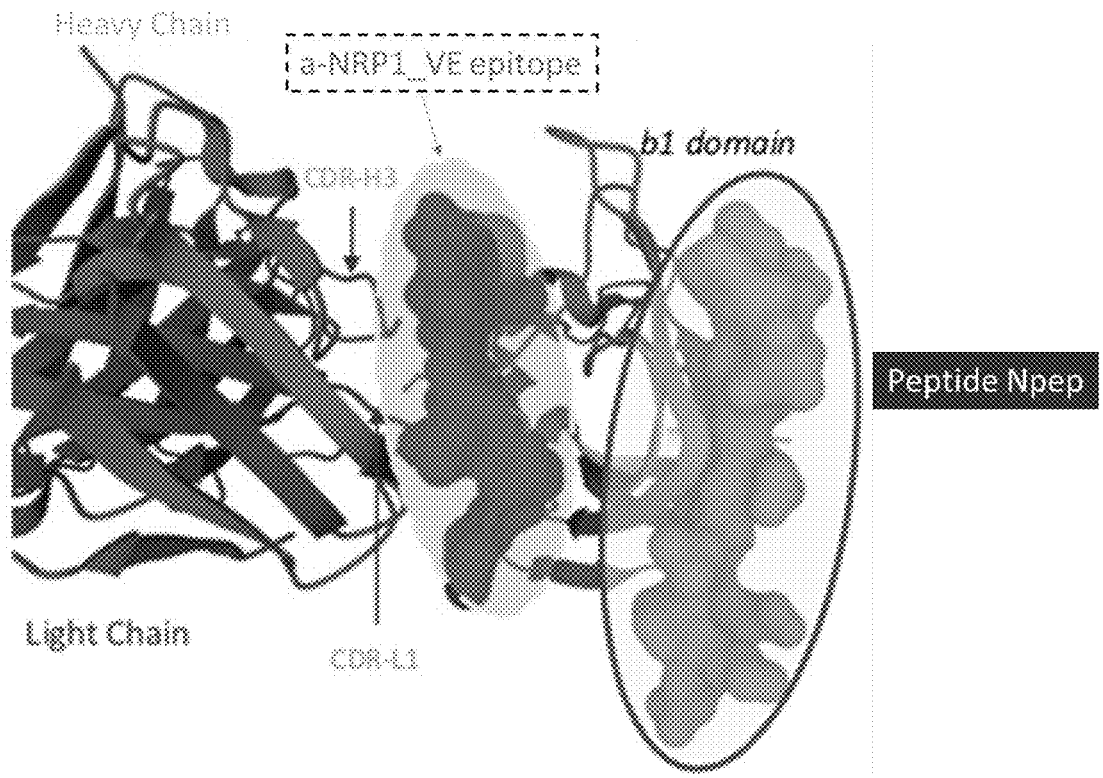

The chimeric and humanized a-NRP1_LEP antibodies of the invention epitope specificity corresponding to the leptin binding site to NRP-1 at the b1 domain (FIG. 3A) is demonstrated by the absence of the recognition of this peptide sequence by the prior art antibodies a-NRP1_VE and a-NRP1_SEM targeting specifically the binding site of VEGF and SEMA to NRP-1 respectively (table 2). While all cited antibodies above were able to bind to human and mouse recombinant NRP-1 and to the cell expressing native NRP-1 protein on their surface. The a-NRP1_LEP and a-NRP1_VE epitopes are illustrated in FIG. 3B.

TABLE 2

The ELISA confirmation of the chimeric and humanized variants of a-NRP1_LEP antibodies specificity compared to irrelevant human immunoglobulin and prior art antibodies (a-NRP1_VE and a-NRP1_SEM) for the binding (10 μg/ml) to immobilized human and murine recombinant NRP-1 (1 μg) and a synthetic peptide Npep (2 μg).

|  |  | Absorbance on human NRP-1 (1 μg) | Absorbance on murine NRP-1 (1 μg) | Absorbance on NRP-1 peptide (Npep) (2 μg) |
|---|---|---|---|---|
| chimeric a-NRP1_LEP | Invention | 1.227 | 0.925 | 0.788 |
| variant 4 a-NRP1_LEP |  | 0.953 | 0.986 | 0.855 |
| variant 6 a-NRP1_LEP |  | 0.799 | 0.720 | 0.684 |
| variant 8 a-NRP1_LEP |  | 0.590 | 0.412 | 0.475 |
| variant 18 a-NRP1_LEP |  | 0.452 | 0.371 | 0.344 |
| variant 20 a-NRP1_LEP |  | 0.353 | 0.299 | 0.241 |
| variant 24 a-NRP1_LEP |  | 0.638 | 0.597 | 0.923 |
| hIgG1 | Neg control | 0.073 | 0.084 | 0.05 |
| hIgG4 | | 0.073 | 0.064 | 0.055 |
| a-NRP1_VE | Prior art | 0.766 | 1.745 | 0.052 |
| a-NRP1_SEM |  | 0.407 | 0.431 | 0.063 |

The validation of the antibody of the invention a-NRP1_LEP specificity to NRP-1 protein is demonstrated in A549 WT and NRP-1-KO cells using the prior art antibody a-NRP1_VE as a positive control for NRP-1 protein detection. No NRP-1 protein detection neither with the a-NRP1_LEP antibody of the invention nor with the prior art antibody a-NRP1_VE in A549 NRP-1-KO cell line as shown in FIG. 4A. Interestingly we identified a specificity of both antibodies a-NRP1_LEP and a-NRP1_VE to GAG-modified NRP-1 (>150 kDa). While the antibody of the invention a-NRP1_LEP is mostly able to bind with high specificity to GAG-modified NRP-1 (>150 kDa) as demonstrated with CTC41.5E cells (FIG. 4A) as well with multiple cell types (human breast cancer cell line MDA-MB231, human colon cancer cell line COLO 205 and murine breast cancer cell line 4T1), the prior art antibody recognizes slightly the GAG-modified NRP-1 (>150 kDa) as reported in FIG. 4A.

The exclusive and unique ability of a-NRP1_LEP antibody to bind, with a higher specificity the GAG-modified NRP-1 protein can be dependent of the cell types and their state. Thus, the highly GAG-modified form of NRP-1 could serve (i) in the resistance to stress as observed in serum starved MDA-MB-231 breast cancer cell line (MDA-MB-231) which express exclusively the GAG-modified form (>150 kDa) (FIG. 4B) compared to the non-stressed cells which express both, the non-GAG-modified NRP-1 (≤150 kDa) and the highly GAG-modified NRP-1 (>150 kDa) (FIG. 5B) and also (ii) in therapies escape mechanisms as observed in the circulating tumor cells, considered as 'Stem Cell Like" cells, isolated from patient suffering from metastatic colon cancer CTC41.5E with resistance to therapies. These cells seem to express a specific highly GAG-modified form of NRP-1 which can be highly detected by our a-NRP1_LEP antibody as shown in FIG. 4A, contrary to other anti-NRP-1 ligands such as the well-known a-NRP1_VE antibody. Further, antibodies of the invention bind weakly to non-GAG-modified NRP-1 in both, immortalized (A549) and patient derived (CTCs) cancerous cells (FIG. 4).

The association of the GAG-modified NRP-1 to the a-NRP1_LEP target, the leptin-dependent NRP-1/OBR complex is demonstrated in human breast cancer (MDA-MB-231), human colon cancer cell (COLO 205) and murine breast cancer (4T1) cell lines (FIGS. 4B and C). NRP-1 immunoprecipitation in leptin-treated cells, after overnight serum starvation, have shown that the a-NRP1_LEP antibodies are able to bind a high molecular weight form of GAG-modified NRP-1 (>150 kDa) in a leptin-dependent manner, unlike the prior art antibodies a-NRP1_VE and a-NRP1_SEM which target the binding site of VEGF and semaphorin on NRP-1 respectively, confirming the antibodies of the invention specificity to the leptin-binding site on NRP-1 protein (FIG. 4C). Under leptin stimulation, the two historical antibodies of the prior art a-NRP1_VE and a-NRP1_SEM bind mainly to the glycosylated form of NRP-1 (≤150 kDa) and, in a lesser extent, to the high molecular weight form of NRP-1 (>250 kDa) (FIG. 4C). Moreover, the signal is higher when cells were incubated with leptin for 3h, a treatment that induces the increase of NRP-1/OBR protein complex formation at the cell membrane (FIG. 4C).

Taken together, these data indicate that the a-NRP1_LEP antibody of the invention, but not the prior art a-NRP1_VE and a-NRP1_SEM antibodies, binds mainly to a post-translational modified high molecular weight form of NRP-1 (>250 kDa) (GAG-modified NRP-1) associated to NRP-1/OBR complex as confirmed by co-immunoprecipitation on CTCs collected from patient (FIG. 4D).

Because the a-NRP1_LEP antibody binds to a high molecular weight form of NRP-1, we decided to investigate the nature of this post-translational modification. It is already known that NRP-1 is a heavily glycosylated proteoglycan with covalently attached glycosaminoglycan (GAG) chain(s) (Glycosaminoglycan modification of neuropilin-1 modulates VEGFR2 signaling. Yasunori Shintani, Seiji Takashima, Yoshihiro Asano, Hisakazu Kato, Yulin Liao, Satoru Yamazaki, Osamu Tsukamoto, Osamu Seguchi, Hiroyuki Yamamoto, Tomi Fukushima, Kazuyuki Sugahara, Masafumi Kitakaze, Masatsugu Hori. EMBO J 2006 Jul. 12;25(13):3045-55 and Chondroitin sulphate-modified neuropilin 1 is expressed in human tumour cells and modulates 3D invasion in the U87MG human glioblastoma cell line through a p130Cas-mediated pathway. Paul Frankel, Caroline Pellet-Many, Pauliina Lehtolainen, Giovanna M D'Abaco, Michelle L Tickner, Lili Cheng, Ian C Zachary. EMBO Rep 2008 Oct.;9(10):983-9). Among the four different classes of GAGs, we focused on chondroitin sulfate and heparan sulfate. Flow cytometry analyses of MDA-MB-231 cells treated with chondroitinase for 2 hours, reveal a decrease of the percentage of cells stained by a-NRP1_LEP (mouse, chimeric and humanized variants) compared to the prior art antibodies a-NRP1_VE and a-NRP1_SEM represented by a shift of fluorescence intensity histogram (FIG. 5A—grey histogram), meaning, a decrease in the a-NRP1_LEP binding to the cell surface GAG-modified NRP-1 (Table 3).

TABLE 3

Percentage of a-NRP1_LEP antibodies of the invention binding to native NRP-1 on MDA-MB-231 cells under chondroitinase treatment compared to prior art antibodies (a-NRP1_SEM and a-NRP1_LEP) and their corresponding isotype controls.

| | | | | | | | a-NRP1_LEP | | | | |
|---|---|---|---|---|---|---|---|---|---|---|---|
| | antibodies | Isotype controls | | | Prior art antibodies | | | | variant | variant | variant |
| Treatment | concentration | hIgG1 | mIgG2b | hIgG4 | a-NRP1_VE | a-NRP1_SEM | mouse | chimeric | no 4 | no 6 | no 8 |
| −chondroitinase | 40 ug/ml | 0.1 | 0.45 | 0.47 | 100 | 100 | 89.3 | 93.5 | 93.2 | 85.3 | 75.6 |
| +chondroitinase | | 0.063 | 0.66 | 0.45 | 99.9 | 99.9 | 84.5 | 87.5 | 86.4 | 69.1 | 61.5 |
| delta (% of control) | | | | | −0.1 | −0.1 | −4.8 | −4 | −6.8 | −16.2 | −14.1 |
| −heparinase | 10 ug/ml | 0.17 | 0.086 | 0.2 | 98 | 96.6 | 10.1 | 16.5 | 12.4 | 13.1 | 13.3 |
| +heparinase | | 0.14 | 0.28 | 0.24 | 97.9 | 97.7 | 6.41 | 13.6 | 10.1 | 11.5 | 9.88 |
| delta (% of control) | | | | | −0.1 | 1.1 | −3.69 | −2.9 | −2.3 | −1.6 | −3.42 |

These data are validated by the decrease of the GAG-modified form of NRP-1 detection by western blotting after the treatment of the a-NRP1_LEP immunoprecipitated-NRP-1 with chondroitinase compared to the a-NRP1_VE and a-NRP1_SEM immunoprecipitated-NRP-1 (FIG. 5B).

As expected, a-NRP1_VE and a-NRP1_SEM bind mainly to the glycosylated form of NRP-1 (≤150 kDa) and in a lesser extent, to the high molecular weight form of NRP-1 (>250 kDa), especially a-NRP1_VE (FIG. 5B) which correlates with the flow cytometry analysis showing no significant decrease of their binding to the cell surface of MDA-MB-231 cell line. In contrast to flow cytometry analyses, the treatment of immunoprecipitated cell lysates with chondroitinase or heparinase show that a-NRP1_VE recognizes a low molecular weight of chondroitin sulfate form (FIG. 5B). In opposite, as already demonstrated above, both the chimeric and variant a-NRP1_LEP antibodies bind more the high molecular weight GAGs-modified NRP-1 than glycosylated form of NRP-1 (≤150 kDa) (FIG. 5B). Interestingly, it appears that a-NRP1_LEP recognizes both chondroitin and heparan sulfate GAGs of NRP-1 (FIG. 5B).

These data showed that antibodies of the invention recognize a new epitope, distinct from that recognized by the prior art antibodies.

An additional confirmation of the GAG-modified NRP-1 recognition by a-NRP1_LEP antibodies was assessed by PNGase treatment of immunoprecipitated samples obtained with humanized antibody of the invention from cell lysates of CTCs collected from the patient. Interestingly, we can observe a loss of the highest form of GAG-modified NRP-1 (>250 kDa) and an enrichment of the glycosylated form of NRP-1 (≤150 kDa) (FIG. 5C).

EXAMPLE 4: The a-NRP1_LEP antibodies are capable to enter into the nucleus of multiple types of cancer cells.

The characterization of the a-NRP1_LEP properties such as cell surface attachment, entry into the cells and cellular compartments localization in CTCs by FITC-conjugated secondary anti-human and anti-mouse IgG antibodies, has revealed unexpected nuclear localization of the a-NRP1_LEP antibodies of the invention. This unique property has not been reported for any anti-NRP-1 antibody either in basic research or drug development fields (FIG. 6.1 A-a).

The validation of the a-NRP1_LEP antibodies nuclear entry is demonstrated by its detection in nuclear fraction of multiple a-NRP1_LEP treated-cell types, after immunoprecipitation with protein A and protein G Sepharose 4 Fast Flow beads and western blot analysis (FIGS. 6.1 and 6.2). This unexpected ability of antibodies of the invention to enter into the nucleus was not observed in any treated cell type (PC3 human prostate cell line, 4T1 mouse breast cancer cell and CTCs human circulating tumor cells collected from patient) with the prior art antibodies (a-NRP1_VE and a-NRP1_SEM) (FIG. 6.2). The efficacy of the cellular fractionation technique adopted previously was confirmed using the specific nuclear marker HDAC2 protein.

EXAMPLE 5: NRP-1-dependent entry of the antibody of the invention, a-NRP1_LEP, into the nucleus via the NRP-1/OBR complex in tumor cells.

The NRP-1 dependent-entry of a-NRP1_LEP antibody into the nucleus was confirmed by a very high detection of the a-NRP1_LEP antibody in wild type A549 lung cancer cell line compared to NRP-1 Knockout cell line (FIGS. 7.1 A-a and A-b).

The NRP-1/OBR complex dependent-entry of the a-NRP1_LEP antibody is demonstrated by the dose-dependent NRP-1/OBR complex formation under a-NRP1_LEP treatment of MDA-MB-231 cell line (FIGS. 7.1 B-a and B-b). The significant increase of NRP-1/OBR complex formation, detected by proximity ligation assay, is specific of the a-NRP1_LEP since neither the isotype control mouse IgG2b nor the a-NRP1_VE have this effect (FIGS. 7.1 B-a and B-b).

EXAMPLE 6: Leptin-dependent induction of simultaneous NRP-1 and a-NRP1_LEP antibody translocation into the nucleus of CTC41.5E cell line.

Leptin dependent NRP-1/OBR complex formation and translocation into the nucleus was reported in previous patent (WO 2015/124588), and based on the recent discovery of the NRP-1-dependent nuclear entry of the antibody of the invention a-NRP1_LEP (EXAMPLE 4), we investigated the simultaneous nuclear localization of a-NRP1_LEP antibody and the GAG-modified NRP-1 protein. The immunoprecipitation with protein A and protein G Sepharose 4 Fast Flow beads followed by western blot analysis of the nuclear fraction from overnight serum starved CTCs stimulated with Leptin for 3 hours, revealed a simultaneous detection of a-NRP1_LEP antibody and GAG-modified NRP-1 protein in a leptin-dependent manner (FIG. 7.2).

EXAMPLE 7: Antibodies of the invention, a-NRP-1-LEP, induce DNA damages in circulating tumor cells.

The consequences of the antibodies of the invention a-NRP1_LEP entry into the nucleus was investigated in circulating tumor cells CTCs treated with variant a-NRP1_LEP (Var4, 6 and 8) as well with their isotype control hIgG4 or prior art antibody a-NRP1_VE. These cells were selected for (i) the high expression of GAG-modified NRP-1 protein in CTCs collected from patients before treatment (CTC41) and after the second line of treatment and relapse, (ii) the high probability of the association of this NRP-1 form to therapies resistance (such as chemotherapy and anti-angiogenic drug) and (iii) the binding of the a-NRP1_LEP antibody to the native form of NRP-1 protein on the CTCs cell surface (table 4).

TABLE 4

Percent of bound circulating tumor cells (CTC) with the anti-NRP-1 antibodies of the invention, a-NRP1_LEP.

|  | antibodies concentration (ug/ml) | cells | |
|---|---|---|---|
|  |  | mix | CTC41 | CTC41.5E |
| mIgG2b | 10 | 3.65 |  |  |
|  | 25 | 6.66 |  |  |
|  | 50 | 14.4 |  |  |
| mouse a-NRP1 LEP | 10 |  | 85.5 | 63 |
|  | 25 |  | 87.3 | 71.6 |
|  | 50 |  | 90.1 | 82.5 |
| hIgG4 | 10 | 2.04 |  |  |
|  | 25 | 3.3 |  |  |
|  | 50 | 4.04 |  |  |
| variant n°4 a-NRP1_LEP | 10 |  | 93.1 | 91.5 |
|  | 25 |  | 94.2 | 92.1 |
|  | 50 |  | 94.3 | 91.8 |

The cytogenetic analyses have revealed genotoxic properties of the antibodies of the present invention, inducing thus DNA damage represented by chromosomes pulverization (FIG. 8A), multiple acentric fragments (FIG. 8B) and micronuclei (FIG. 8C). This genotoxic effect was barely present in the case of both prior art antibodies a-NRP1_VE and a-NRP1_SEM which correlates with their inability to enter to into the cells' nucleus.

The quantification of the genotoxic effect of the antibodies of the invention a-NRP1_LEP; (i) presented by the number of acentric fragments was statistically significant ($p<0.001$, Fisher test) when compared to the isotype control hIgG4 in the case of both CTC41 and CTC41.5E cell lines. In contrast, the number of acentric fragments induced by the prior art antibody a-NRP1_VE and a-NRP1_SEM antibodies was less significant ($p<0.05$, Fisher test) or non-significant ($p>0.05$, Fisher test) respectively compared to their isotype control hIgG1 in the case of CTC41 cell line and both non-significant in the case of CTC41.5E cell line (FIG. 8B); (ii) presented by the number of micronuclei was statistically significant when compared to the isotype control hIgG4 in the case of both CTC41 ($p<0.05$, Fisher test) and CTC41.5E ($p<0.001$, Fisher test) cell lines. In contrast, the number of number of micronuclei induced by the prior art antibody a-NRP1_VE and a-NRP1_SEM antibodies was less significant ($p<0.05$) or non-significant ($p>0.05$) respectively compared to their isotype control hIgG1 in the case of CTC41.5E cell line and both non-significant in the case of CTC41 cell line (FIG. 8C). In order to better understand this genotoxic effect of the antibody of the invention a-NRP1_LEP, we tested its ability to interact with proteins associated to DNA repair machinery (detailed in example 8) or its ability of chromatin remodeling. The subcellular fractionation of a-NRP1_LEP treated cells revealed the binding of the antibody of the invention a-NRP1_LEP to the chromatin after its entry into the nucleus of CTC cells (FIG. 10).

EXAMPLE 8: NRP-1 interaction with proteins associated to DNA repair machinery revealed by the antibody of the invention a-NRP1_LEP.

The association of GAG-modified NRP-1 protein to the DNA damage due to its simultaneous nuclear entry with the genotoxic antibody of the invention a-NRP1_LEP is revealed by its co-immunoprecipitation with the DNA repair proteins using the a-NRP1_LEP antibody as revealed by mass spectrometry analysis. Table 5 shows the enrichment of proteins involved in different DNA repair pathways detected in immunoprecipitated samples from CTC41.5E and A459 lung cancer cell lysates using the a-NRP1_LEP variant 4 antibody (V4 in light grey) and the prior art antibody (a-NRP1_VE, selected for its barely genotoxic effect) (TAB in dark grey). The proteins associated to DNA repair reported in table 5 are selected on the basis of the acceptable (significant) values for the number and the peak area of their enriched unique peptides (represented in bold for the a-NRP1_LEP and the a-NRP1_VE antibody).

A functional protein association network representing unreported NRP-1 interactome with a variety of DNA repair proteins immunoprecipitated with the a-NRP1_LEP antibody of the invention compared to the anti-NRP-1 antibody of the anterior art a-NRP1_VE and detected by LC-MS/MS was shown in FIG. 9. These enriched proteins seem to have experimentally determined interactions or predicted interactions such as gene neighborhood, gene fusions, gene co-occurrence/co-expression or protein homology.

TABLE 5

List of immunoprecipitated proteins associated with the a-NRP1_LEP antibody of the invention and detected by LC-MS/MS.

|  |  |  | Circulating Tumor Cell line CTC41.5E | | | Human lung cancer cell line A549 WT | | |
|---|---|---|---|---|---|---|---|---|
|  |  |  | Acceptable values ≥ 2 | Acceptable values ≥ 10 | | Acceptable values ≥ 2 | Acceptable values ≥ 10 | |
| Group | Gene | DNA repair mechanisms | Unique peptide | Ratio Area V4/IgG4 | Ratio Area TAB/IgG1 | Unique peptide | Ratio Area V4/IgG4 | Ratio Area TAB/IgG1 |
| A | PARP1 | DSB (HR, NHEJ) and SSB (BER) repair | 36 | 708.8 | 0.9 | 4 | 545.7 | 1.0 |
|  | LI63 | SSB repair (BER) | 18 | 7769.4 | 1.0 | 3 | 78.8 | 1.0 |
|  | SUPT16H | SSB repair (NER) | 9 | 5491.6 | 1.0 | 11 | 6028.4 | 0.6 |
|  | TOP2A | SSB repair (NER) | 5 | 538.5 | 1.0 | 8 | 1436.8 | 1.0 |
|  | PDSSB | SSB repair (RER) | 9 | 12.5 | 533.9 | 2 | 358.0 | 1.0 |
|  | MACROH2A1 | ADP-Ribose-medicated chromatin modulation | 6 | 8783.2 | 1.0 | 2 | 1129.8 | 1.0 |
|  | H3C1 | Histone code, and nucleosome remodeling | 2 | 304.1 | 1.0 | 2 | 82.5 | 1.8 |

TABLE 5-continued

List of immunoprecipitated proteins associated with the a-NRP1_LEP antibody of the invention and detected by LC-MS/MS.

| | | | Circulating Tumor Cell line CTC41.5E | | | Human lung cancer cell line A549 WT | | |
| | | | Acceptable values ≥ 2 | Acceptable values ≥ 10 | | Acceptable values ≥ 2 | Acceptable values ≥ 10 | |
| Group | Gene | DNA repair mechanisms | Unique peptide | Ratio Area V4/IgG4 | Ratio Area TAB/IgG1 | Unique peptide | Ratio Area V4/IgG4 | Ratio Area TAB/IgG1 |
| --- | --- | --- | --- | --- | --- | --- | --- | --- |
| | TOP2B | SSB repair (NER) | 2 | 50.1 | 1.0 | 2 | 369.4 | 1.0 |
| | POLR1A | SSB repair (transcription coupled NER) | 5 | 785.2 | 0.0 | 11 | 3209.6 | 1.0 |
| B | PRKDC | DSB repair (NHEJ) | 106 | 10.5 | 1.47 | 76 | 6.06 | 4.31 |
| | XRCC6 | DSB repair (NHEJ) | 55 | 58.8 | 0.7 | 41 | 1.9 | 0.9 |
| | XRCC5 | DSB repair (NHEJ) | 44 | 38.7 | 0.7 | 30 | 2.3 | 1.1 |
| | TOP1 | SSB repair (RER) | 12 | 6875.1 | 1.0 | 0 | 0.0 | 0.0 |
| | RPA1 | SSB repair (NER) | 12 | 13.6 | 1.1 | 11 | 2.0 | 1.0 |
| | MSH2 | SSB repair (MMR) | 6 | 335.4 | 82.5 | 2 | 1.0 | 1.0 |
| | MSH6 | SSB repair (MMR) | 5 | 812.7 | 270.9 | 0 | 0.0 | 0.0 |
| | WRN | DSB (HR) | 4 | 758.8 | 1.0 | 1 | 540.0 | 1.0 |
| | XPC | SSB repair (NER) | 4 | 479.9 | 1.0 | 0 | 0.0 | 0.0 |
| | H2AZ2 | Chromatin remodeling | 3 | 624.4 | 1.0 | 1 | 22.0 | 1080.2 |
| | H2AZ1 | Chromatin remodeling | 3 | 624.4 | 1.0 | 1 | 22.0 | 1080.2 |
| | SMARCA5 | Chromatin remodeling | 3 | 589.2 | 1.0 | 0 | 0.0 | 0.0 |
| | NMNAT1 | Chromatin remodeling | 3 | 546.6 | 1.0 | 0 | 0.0 | 0.0 |
| | RAD23B | SSB repair (NER) | 2 | 307.1 | 1.0 | 0 | 0.0 | 0.0 |
| C | PARP2 | SSB repair (BER) | 2 | 1.0 | 1.0 | 2 | 259.4 | 1.0 |

DSB: double-strand break, SSB: single-strand break, NHEJ: Non-homologous end joining, HR: Homologous recombination, BER: Base excision repair, NER: Nucleotide excision repair, RER: Ribonucleotide Excision Repair, MMR: Mismatch repair, V4: variant n°4 a-NRP1_LEP, TAB: a-NRP1_VE, PRKDC: DNA-dependent protein kinase catalytic subunit (DNA-PK), XRCC6: X-ray repair cross-complementing protein 6, XRCC5: X-ray repair cross-complementing protein 5, PARP1: Poly [ADP-ribose] polymerase 1, LIG3: DNA ligase 3, TOP1: DNA topoisomerase 1, RPA1: Replication protein A 70 kDa DNA-binding subunit, SUPT16H: FACT complex subunit SPT16, PDS5B: Sister chromatid cohesion protein PDS5 homolog B, MACROH2A1: Core histone macro-H2A.1, MSH2: DNA mismatch repair protein Msh2, TOP2A: DNA topoisomerase 2-alpha, POLR1A: DNA-directed RNA polymerase I subunit RPA1, MSH6: DNA mismatch repair protein Msh6, WRN: Werner syndrome ATP-dependent helicase, XPC: DNA repair protein complementing XP-C cells, H2AZ2: Histone H2A.V, H2AZ1: Histone H2A.Z, SMARCA5: SWI/SNF-related matrix-associated actin-dependent regulator of chromatin subfamily A member 5, NMNAT1: Nicotinamide/nicotinic acid mononucleotide adenylyltransferase 1, H3C1: Histone H3.1, TOP2B: DNA topoisomerase 2-beta, RAD23B: UV excision repair protein RAD23 homolog B, PARP2: Poly [ADP-ribose] polymerase 2.

EXAMPLE 9: In vivo validation of the anti-NRP-1 antibodies of the invention a-NRP1_LEP ability to enter into the nucleus of subcutaneously xenografted CTC cells in SCID mice and to induce DNA damage.

In order to investigate the ability of the a-NRP1_LEP antibody of the invention to diffuse across the tumor vasculature and particularly to reach the nucleus of the cancer cells and induce DNA damage as demonstrated in vitro, female SCID mice were subcutaneously xenografted with CTC41.5E cells into their right flank. When tumors reached an average volume of 300 mm 3, mice were treated once a week with an amount of 200 µg of humanized a-NRP1_LEP variant 4 antibody or its isotype control (human IgG4) by intravenous tail injection. At the end of the experiment, tumor samples (primary tumor) and organs (such as lungs and liver) were collected for histological and biochemical analysis.

Figure 11B:
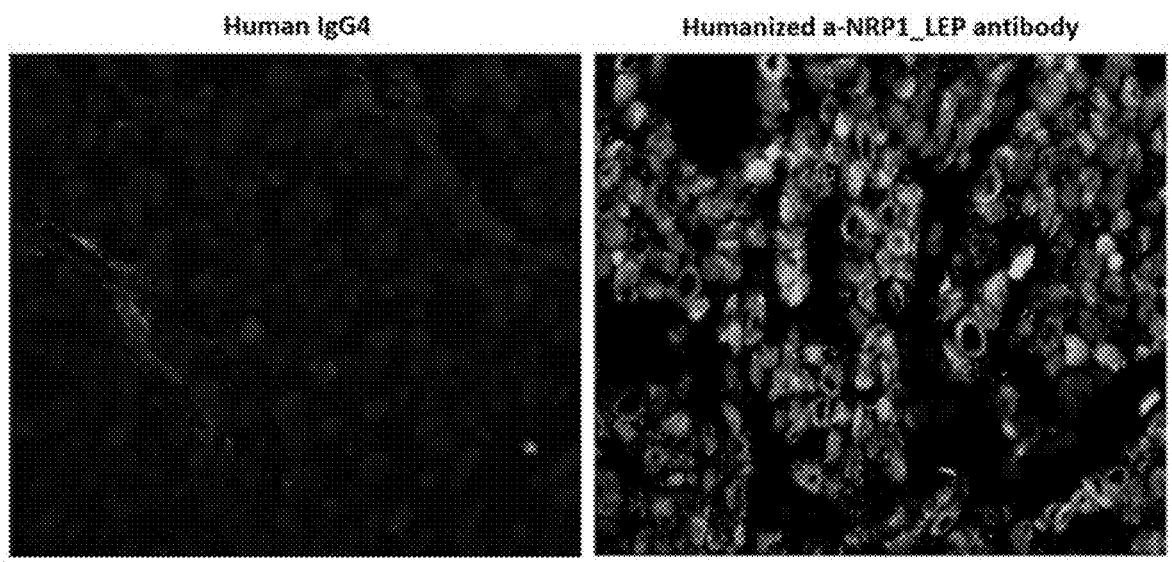

The presence of a-NRP1_LEP antibody in the nucleus of cancer cells was detected either by Western-blotting after its immunoprecipitation using protein A and G Sepharose (FIG. 11A) or by immunofluorescence on frozen tissues sections (FIG. 11B).

Stained sections were then analyzed for telomeres and centromere detection followed by DAPI staining. Interestingly in contrast to the IgG4 isotype control treated mice, we could observe reduction of the intensity of Human telomere signal in a-NRP1_LEP antibody treated SCID mice. This reduction was associated to the presence of telomere shortening, DNA degradations with the presence of micronuclei, and modification of the morphology of subcutaneously xenografted CTC cells in a-NRP1_LEP antibody treated SCID mice (FIG. 12).

EXAMPLE 10: In vivo effect of a a-NRP1_LEP antibody on metastasis and anti-tumor immune response.

Figure 13A:
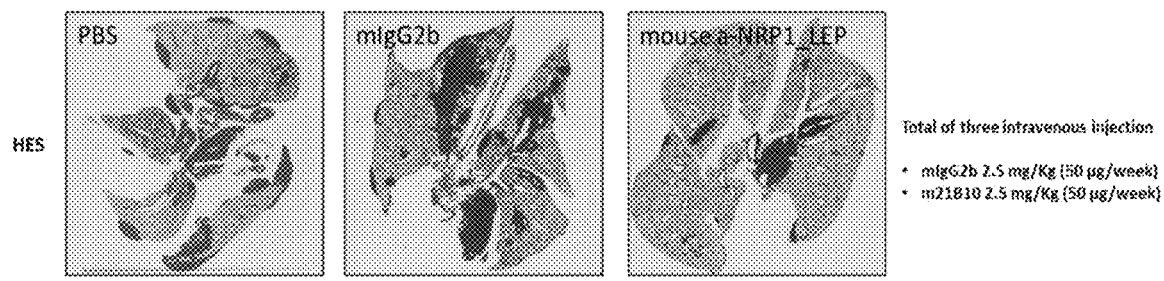
Figure 13B:
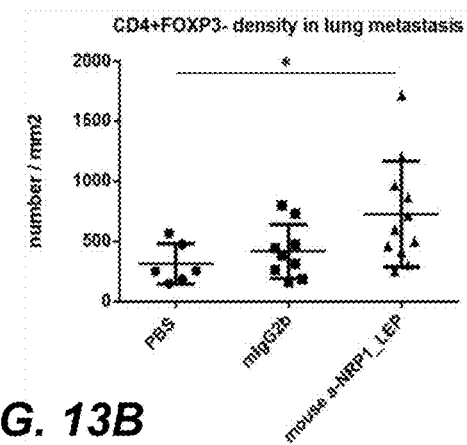
Figure 13C:
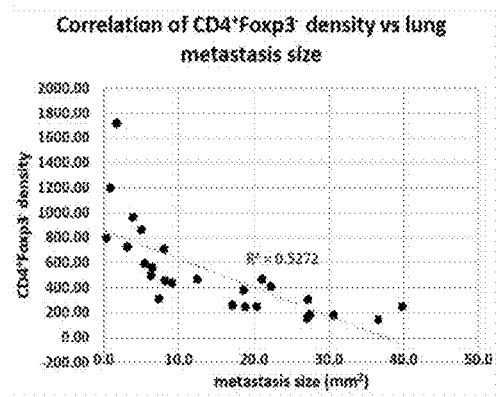
Figure 13D:
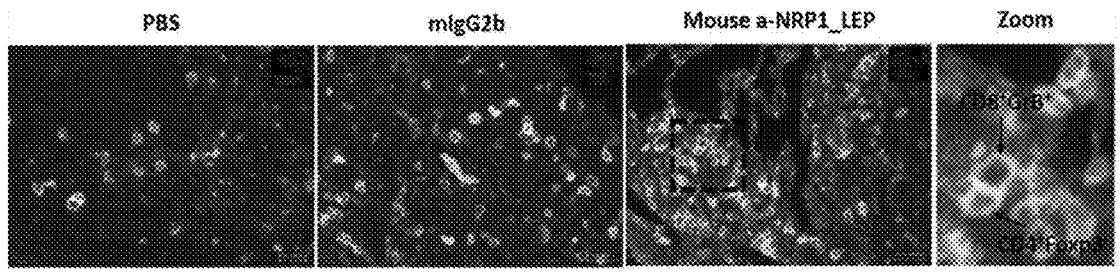

To investigated in vivo the impact and the potential therapeutic efficiency of the a-NRP1_LEP antibody of the invention on metastasis and the anti-tumor immune response, female BALB/c mice were orthotopically grafted with the highly metastatic mouse breast cancer cells 4T1 known for their lung tropism. The injected dose of the a-NRP1_LEP antibody or its isotype control, 2.5 mg/kg (equivalent to 50 µg by a mouse of 20 g average weight) was selected to be lower than the doses used in already published data with the prior art antibodies a-NRP1_VE (5 mg/kg) and a-NRP1_SEM (500 µg/injection). When tumors reached an average volume of 150 mm 3, mice were treated 3 times (once a week) with PBS, mIgG2b isotype control and mouse a-NRP1_LEP antibody by IV injection. At the end of experiment, tumor samples (primary tumor) and organs (such as lungs and liver) were collected, fixed and then HES stained. The CD4 (a glycoprotein that is a co-receptor for the T-cell receptor (TCR)), and FOXP3 markers were performed by immunohistochemistry. On HES slides of lungs (FIG. 13A), we clearly see that mice treated with the mouse a-NRP1_LEP antibody exhibited less pulmonary metastasis than both PBS- and mIgG2b-injected mice. This decrease of metastasis is inversely correlated to CD4 $^{+}$FOXP3$^{-}$ density in the infiltrated lung metastasis (FIGS. 13B and C), indicating a strong mobilization of CD4 $^{+}$FOXP3$^{-}$ T cells in the lungs of mice treated with the mouse a-NRP1_LEP antibody as compared to both control groups. Interestingly, there is a statistically significant negative correlation between CD4 $^{+}$FOXP3$^{-}$ density and metastasis size in lungs (R 2=0,63) since mice characterized by the highest CD4 $^{+}$FOXP3$^{-}$ levels exhibited the lowest size of metastasis (FIG. 10). The a-NRP1_LEP-induced CD4 $^{+}$FOXP3$^{-}$ infiltration represents a very promising result because it was described that a subpopulation of CD4 T cells could have cytotoxic activity (Revisiting the role of CD4 T cells in cancer immunotherapy-new insights into old paradigms. Rong En Tay, Emma K Richardson, Han Chong Toh. Cancer Gene Ther 2021 Feb.;28(1-2):5-17). In primary mammary gland tumors, the a-NRP1_LEP antibody trend to increase the CD4 infiltration. The control isotype used in this study was established from the Merwin plasma cell tumor-II carried in BALB/c mice in the 1970s and its specificity is unknown. Thus, we cannot exclude a modulation of immune system in mice in response to this control antibody. Regarding the CD8 positive T cells, we also observed a trend of increase in the lungs of a-NRP1_LEP-treated mice compared to control mice, but the main interesting observation is the cell-cell contact between CD4[+] and CD8[+]/GrB[+] that could reflect the role of CD4[+] T helper cells in the activation of cytotoxic CD8[+] producing granzyme B (FIG. 13D). Together, these data suggest that a mouse a-NRP1_LEP antibody of the invention is able to mobilize immune system in lungs, especially CD4 T cells for the activation of cytotoxic CD8, in order to kill metastatic cells.

What is claimed is:

1. An antibody or antibody fragment comprising the sequences CDR-H1, CDR-H2, CDR-H3, CDR-L1, CDR-L2 and CDR-L3 as defined below:
   CDR-H1: SFGMH (SEQ ID NO:7),
   CDR-H2: YISSGSSTIHYADTVKG (SEQ ID NO: 8) or YISSGSSTIYYADTVKG (SEQ ID NO:35),
   CDR-H3: RHYGSSRYWYFDV (SEQ ID NO: 9) or RHYGRSRYWYFDV (SEQ ID N0:36),
   CDR-L1: KASQDIKSYLS (SEQ ID NO: 10),
   CDR-L2: YATSLAG (SEQ ID NO: 11) or YATSLAD (SEQ ID N0:38), and
   CDR-L3: LQYGESPYT (SEQ ID NO: 12).

2. The antibody or antibody fragment of claim 1 comprising the following CDRs:
   CDR-H1: SFGMH (SEQ ID NO: 7),
   CDR-H2: YISSGSSTIHYADTVKG (SEQ ID NO: 8),
   CDR-H3: RHYGSSRYWYFDV (SEQ ID NO: 9),
   CDR-L1: KASQDIKSYLS (SEQ ID NO: 10),
   CDR-L2: YATSLAG (SEQ ID NO: 11), and
   CDR-L3: LQYGESPYT (SEQ ID NO: 12).

3. The antibody or antibody fragment of claim 1 comprising the following CDRs:
   CDR-H1: SFGMH (SEQ ID NO: 7),
   CDR-H2: YISSGSSTIYYADTVKG (SEQ ID NO:35),
   CDR-H3: RHYGRSRYWYFDV (SEQ ID NO: 36),
   CDR-L1: KASQDIKSYLS (SEQ ID NO:10),
   CDR-L2: YATSLAD (SEQ ID NO:38), and
   CDR-L3: LQYGESPYT (SEQ ID NO:12).

4. The antibody or antibody fragment of claim 1 comprising
   a heavy chain of SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47 or a sequence sharing at least 80% of sequence identity with the non-CDR regions of SEQ ID NO: 40-47, and
   a light chain of SEQ ID No: 48, SEQ ID NO: 49, SEQ ID NO: 50, SEQ ID NO: 51, SEQ ID NO: 52, SEQ ID NO: 53 or a sequence sharing at least 80% of sequence identity with the non-CDR regions of SEQ ID NO: 48-53.

5. The antibody or antibody fragment of claim 1 comprising
   a heavy chain of SEQ ID NO: 13 or a sequence sharing at least 80% of sequence identity with the non-CDR regions of SEQ ID NO: 13 and a light chain of SEQ ID NO: 26 or a sequence sharing at least 80% of sequence identity with the non-CDR regions of SEQ ID NO: 26,
   a heavy chain of SEQ ID NO: 14 or a sequence sharing at least 80% of sequence identity with the non-CDR regions of SEQ ID NO: 14 and a light chain of SEQ ID NO: 23 or a sequence sharing at least 80% of sequence identity with the non-CDR regions of SEQ ID NO: 23, and
   a heavy chain of SEQ ID No: 14 or a sequence sharing at least 80% of sequence identity with the non-CDR regions of SEQ ID NO: 14 and a light chain of SEQ ID NO: 26 or a sequence sharing at least 80% of sequence identity with the non-CDR regions of SEQ ID NO: 26.

6. The antibody or antibody fragment of claim 1, wherein the antibody is able to enter into nucleus of cells expressing NRP-1/OBR complex and to induce DNA damages and/or telomeres shortening.

7. The antibody or antibody fragment of claim 1, wherein the antibody is an antibody drug conjugated (ADC).

8. The antibody or antibody fragment of claim 1, which is part of a chimeric antigen receptor.

9. A method for treating a disease implicating glycosaminoglycans and DNA damage response (DDR) in a subject in need thereof, the method comprising:
   administering the antibody or antibody fragment of claim 1 to the subject so as to treat the disease.

10. The method according to claim 9, wherein the disease comprises cancer, inflammatory, and/or an infectious disease.

11. The method according to claim 10, wherein the disease is cancer.

12. The method according to claim 9, wherein the antibody is administered in combination with an agent selected from the group consisting of anti-checkpoint inhibitor, an anti-angiogenic inhibitor, an inhibitor of casein kinase 2 and a combination of any thereof.

13. The method according to claim 9, wherein the antibody is administered in combination with an anti-PD1, an anti-PDL1, an anti-CTLA4 agent and/or an anti-VEGF, and/or an anti-CK2.

14. The method according to claim 9, wherein the antibody is administered in combination with therapy inducing DNA damages response including chemotherapy and radiotherapy.

15. A method for increasing immune cell infiltration in the tumor microenvironment of a subject, the method comprising:
   administering the antibody or antibody fragment of claim 1 to the subject.

* * * * *

SEQUENCE LISTING

```
Sequence total quantity: 55
SEQ ID NO: 1             moltype =   length =
SEQUENCE: 1
000

SEQ ID NO: 2             moltype = AA  length = 17
FEATURE                  Location/Qualifiers
VAR_SEQ                  1
                         note = MISC_FEATURE - Y, V or I
VAR_SEQ                  4
                         note = MISC_FEATURE - S, Y or P
VAR_SEQ                  5
                         note = MISC_FEATURE - G, S or D
VAR_SEQ                  6
                         note = MISC_FEATURE - S or G
VAR_SEQ                  7
                         note = MISC_FEATURE - S or G
VAR_SEQ                  8
                         note = MISC_FEATURE - T or S
VAR_SEQ                  9
                         note = MISC_FEATURE - I, K or T
VAR_SEQ                  10
                         note = MISC_FEATURE - H, Y or S
VAR_SEQ                  13
                         note = MISC_FEATURE - D or Q
VAR_SEQ                  14
                         note = MISC_FEATURE - S, K or T
VAR_SEQ                  15
                         note = MISC_FEATURE - V or F
VAR_SEQ                  16
                         note = MISC_FEATURE - K or Q
source                   1..17
                         mol_type = protein
                         organism = synthetic construct
SEQUENCE: 2
XISXXXXXXX YAXXXXG                                                        17

SEQ ID NO: 3             moltype = AA  length = 13
FEATURE                  Location/Qualifiers
source                   1..13
                         mol_type = protein
                         organism = Mus musculus
SEQUENCE: 3
RHYGSSRYWY FDV                                                            13

SEQ ID NO: 4             moltype = AA  length = 11
FEATURE                  Location/Qualifiers
VAR_SEQ                  1
                         note = MISC_FEATURE - K or R
VAR_SEQ                  5
                         note = MISC_FEATURE - D or S
VAR_SEQ                  6
                         note = MISC_FEATURE - I or V
VAR_SEQ                  7
                         note = MISC_FEATURE - K or S
VAR_SEQ                  9
                         note = MISC_FEATURE - Y or W
VAR_SEQ                  11
                         note = MISC_FEATURE - S or A
source                   1..11
                         mol_type = protein
                         organism = synthetic construct
SEQUENCE: 4
XASQXXXSXL X                                                              11
```

-continued

```
SEQ ID NO: 5           moltype =   length =
SEQUENCE: 5
000

SEQ ID NO: 6           moltype = AA   length = 9
FEATURE                Location/Qualifiers
VAR_SEQ                1
                       note = synthetic - L or Q
VAR_SEQ                4
                       note = synthetic - G or S
VAR_SEQ                5
                       note = synthetic - E or S
VAR_SEQ                7
                       note = synthetic - P or S
source                 1..9
                       mol_type = protein
                       organism = synthetic construct
SEQUENCE: 6
XQYXXSXYT                                                              9

SEQ ID NO: 7           moltype = AA   length = 5
FEATURE                Location/Qualifiers
source                 1..5
                       mol_type = protein
                       organism = Mus musculus
SEQUENCE: 7
SFGMH                                                                  5

SEQ ID NO: 8           moltype = AA   length = 17
FEATURE                Location/Qualifiers
source                 1..17
                       mol_type = protein
                       organism = Mus musculus
SEQUENCE: 8
YISSGSSTIH YADTVKG                                                    17

SEQ ID NO: 9           moltype = AA   length = 13
FEATURE                Location/Qualifiers
source                 1..13
                       mol_type = protein
                       organism = Mus musculus
SEQUENCE: 9
RHYGSSRYWY FDV                                                        13

SEQ ID NO: 10          moltype = AA   length = 11
FEATURE                Location/Qualifiers
source                 1..11
                       mol_type = protein
                       organism = Mus musculus
SEQUENCE: 10
KASQDIKSYL S                                                          11

SEQ ID NO: 11          moltype = AA   length = 7
FEATURE                Location/Qualifiers
source                 1..7
                       mol_type = protein
                       organism = Mus musculus
SEQUENCE: 11
YATSLAG                                                                7

SEQ ID NO: 12          moltype = AA   length = 9
FEATURE                Location/Qualifiers
source                 1..9
                       mol_type = protein
                       organism = Mus musculus
SEQUENCE: 12
LQYGESPYT                                                              9

SEQ ID NO: 13          moltype = AA   length = 122
FEATURE                Location/Qualifiers
source                 1..122
                       mol_type = protein
                       organism = synthetic construct
SEQUENCE: 13
EVQLVESGGG LVQPGGSLRL SCAASGFTFS SFGMHWVRQA PGKGLEWVAY ISSGSSTIHY      60
ADSVKGRFTI SRDNAKNSLY LQMNSLRAED TAMYYCARRH YGSSRYWYFD VWGQGTTVTV     120
SS                                                                   122

SEQ ID NO: 14          moltype = AA   length = 122
```

```
FEATURE                 Location/Qualifiers
source                  1..122
                        mol_type = protein
                        organism = synthetic construct
SEQUENCE: 14
EVQLVESGGG LVQPGGSLRL SCAASGFTFS SYSMHWVRQA PGKGLEWVSY ISSGSSTIHY   60
ADSVKGRFTI SRDNAKNSLY LQMNSLRAED TAVYYCARRH YGSSRYWYFD VWGQGTTVTV  120
SS                                                                 122

SEQ ID NO: 15           moltype = AA  length = 122
FEATURE                 Location/Qualifiers
source                  1..122
                        mol_type = protein
                        organism = synthetic construct
SEQUENCE: 15
EVQLVESGGG LVQPGGSLRL SCAASGFTFS SYSMHWVRQA PGKGLEWVSY ISSSSSTIYY   60
ADSVKGRFTI SRDNAKNSLY LQMNSLRAED TAVYYCARRH YGSSRYWYFD VWGQGTTVTV  120
SS                                                                 122

SEQ ID NO: 16           moltype = AA  length = 122
FEATURE                 Location/Qualifiers
source                  1..122
                        mol_type = protein
                        organism = synthetic construct
SEQUENCE: 16
QVQLVESGGG VVQPGGSLRL SCAASGFTFS SFGMHWVRQA PGKGLEWVAY ISSGSSTIHY   60
ADSVKGRFTI SRDNSKNTLY LQMNSLRAED TAMYYCARRH YGSSRYWYFD VWGQGTTVTV  120
SS                                                                 122

SEQ ID NO: 17           moltype = AA  length = 122
FEATURE                 Location/Qualifiers
source                  1..122
                        mol_type = protein
                        organism = synthetic construct
SEQUENCE: 17
QVQLVESGGG VVQPGRSLRL SCAASGFTFS SYGMHWVRQA PGKGLEWVAY ISSGGSTKHY   60
ADSVKGRFTI SRDNSKNTLY LQMNSLRAED TAVYYCARRH YGSSRYWYFD VWGQGTTVTV  120
SS                                                                 122

SEQ ID NO: 18           moltype = AA  length = 122
FEATURE                 Location/Qualifiers
source                  1..122
                        mol_type = protein
                        organism = synthetic construct
SEQUENCE: 18
QVQLVESGGG VVQPGRSLRL SCAASGFTFS SYGMHWVRQA PGKGLEWVAV ISYDGSTKYY   60
ADSVKGRFTI SRDNSKNTLY LQMNSLRAED TAVYYCARRH YGSSRYWYFD VWGQGTTVTV  120
SS                                                                 122

SEQ ID NO: 19           moltype = AA  length = 122
FEATURE                 Location/Qualifiers
source                  1..122
                        mol_type = protein
                        organism = synthetic construct
SEQUENCE: 19
QVQLVQSGAE VKKPGASVKV SCKASGYTFT SFGMHWVRQA PGQGLEWMGY ISSSSSTIHY   60
AQKVKGRFTI TRDNSTNTLY LEMSSLRSED TAMYYCARRH YGSSRYWYFD VWGQGTTVTV  120
SS                                                                 122

SEQ ID NO: 20           moltype = AA  length = 122
FEATURE                 Location/Qualifiers
source                  1..122
                        mol_type = protein
                        organism = synthetic construct
SEQUENCE: 20
QVQLVQSGAE VKKPGASVKV SCKASGYTFT SYGMHWVRQA PGQGLEWMGY ISSSGSSTHY   60
AQKFQGRFTM TRDTSTSTVY MELSSLRSED TAVYYCARRH YGSSRYWYFD VWGQGTTVTV  120
SS                                                                 122

SEQ ID NO: 21           moltype = AA  length = 122
FEATURE                 Location/Qualifiers
source                  1..122
                        mol_type = protein
                        organism = synthetic construct
SEQUENCE: 21
QVQLVQSGAE VKKPGASVKV SCKASGYTFT SYYMHWVRQA PGQGLEWMGI ISPSGGSTSY   60
AQKFQGRVTM TRDTSTSTVY MELSSLRSED TAVYYCARRH YGSSRYWYFD VWGQGTTVTV  120
SS                                                                 122
```

-continued

```
SEQ ID NO: 22            moltype = AA   length = 107
FEATURE                  Location/Qualifiers
source                   1..107
                         mol_type = protein
                         organism = synthetic construct
SEQUENCE: 22
DIQMTQSPST LSASVGDRVT ITCRASQDIK SYLSWYQQKP GKAPKTLIYY ATSLAGGVPS    60
RFSGSGSGQE YTLTISSLQP DDFATYYCLQ YGESPYTFGQ GTKLEIK                 107

SEQ ID NO: 23            moltype = AA   length = 107
FEATURE                  Location/Qualifiers
source                   1..107
                         mol_type = protein
                         organism = synthetic construct
SEQUENCE: 23
DIQMTQSPST LSASVGDRVT ITCRASQSIK SYLAWYQQKP GKAPKLLIYY ASSLASGVPS    60
RFSGSGSGTE FTLTISSLQP DDFATYYCQQ YGESSYTFGQ GTKLEIK                 107

SEQ ID NO: 24            moltype = AA   length = 107
FEATURE                  Location/Qualifiers
source                   1..107
                         mol_type = protein
                         organism = synthetic construct
SEQUENCE: 24
DIQMTQSPST LSASVGDRVT ITCRASQSIS SWLAWYQQKP GKAPKLLIYY ASSLESGVPS    60
RFSGSGSGTE FTLTISSLQP DDFATYYCQQ YGSSSYTFGQ GTKLEIK                 107

SEQ ID NO: 25            moltype = AA   length = 107
FEATURE                  Location/Qualifiers
source                   1..107
                         mol_type = protein
                         organism = synthetic construct
SEQUENCE: 25
EIVMTQSPAT LSLSPGERAT LSCRASQDIK SYLSWYQQKP GQAPRTLIYY ATSLAGGIPA    60
RFSGSGSGQD YTLTISSLEP EDFAVYYCLQ YGESPYTFGQ GTKLEIK                 107

SEQ ID NO: 26            moltype = AA   length = 107
FEATURE                  Location/Qualifiers
source                   1..107
                         mol_type = protein
                         organism = synthetic construct
SEQUENCE: 26
EIVLTQSPAT LSLSPGERAT LSCRASQSVK SYLAWYQQKP GQAPRLLIYY ASSRATGIPA    60
RFSGSGSGTD FTLTISSLEP EDFAVYYCQQ YSESPYTFGQ GTKLEIK                 107

SEQ ID NO: 27            moltype = AA   length = 107
FEATURE                  Location/Qualifiers
source                   1..107
                         mol_type = protein
                         organism = synthetic construct
SEQUENCE: 27
EIVLTQSPAT LSLSPGERAT LSCRASQSVS SYLAWYQQKP GQAPRLLIYD ASSRATGIPA    60
RFSGSGSGTD FTLTISSLEP EDFAVYYCQQ YSESPYTFGQ GTKLEIK                 107

SEQ ID NO: 28            moltype =   length =
SEQUENCE: 28
000

SEQ ID NO: 29            moltype = AA   length = 17
FEATURE                  Location/Qualifiers
VAR_SEQ                  1
                         note = MISC_FEATURE - Y or V
VAR_SEQ                  4
                         note = MISC_FEATURE - S or Y
VAR_SEQ                  5
                         note = MISC_FEATURE - S or G
VAR_SEQ                  6
                         note = MISC_FEATURE - S or G
VAR_SEQ                  9
                         note = MISC_FEATURE - I or K
VAR_SEQ                  14
                         note = MISC_FEATURE - T or S
VAR_SEQ                  14
                         note = MISC_FEATURE - T or S
source                   1..17
                         mol_type = protein
                         organism = synthetic construct
SEQUENCE: 29
XISXXXSTXY YADXVKG                                                   17
```

```
SEQ ID NO: 30           moltype = AA  length = 13
FEATURE                 Location/Qualifiers
source                  1..13
                        mol_type = protein
                        organism = synthetic construct
SEQUENCE: 30
RHYGRSRYWY FDV                                                          13

SEQ ID NO: 31           moltype = AA  length = 11
FEATURE                 Location/Qualifiers
VAR_SEQ                 1
                        note = MISC_FEATURE - K or R
VAR_SEQ                 5
                        note = MISC_FEATURE - D or S
VAR_SEQ                 6
                        note = MISC_FEATURE - I or V
VAR_SEQ                 7
                        note = MISC_FEATURE - K or S
VAR_SEQ                 11
                        note = MISC_FEATURE - S or A
source                  1..11
                        mol_type = protein
                        organism = synthetic construct
SEQUENCE: 31
XASQXXXSYL X                                                            11

SEQ ID NO: 32           moltype =     length =
SEQUENCE: 32
000

SEQ ID NO: 33           moltype = AA  length = 9
FEATURE                 Location/Qualifiers
VAR_SEQ                 1
                        note = MISC_FEATURE - L or Q
VAR_SEQ                 7
                        note = MISC_FEATURE - P or S
source                  1..9
                        mol_type = protein
                        organism = synthetic construct
SEQUENCE: 33
XQYGESXYT                                                               9

SEQ ID NO: 34           moltype = AA  length = 5
FEATURE                 Location/Qualifiers
source                  1..5
                        mol_type = protein
                        organism = synthetic construct
SEQUENCE: 34
SFGMH                                                                   5

SEQ ID NO: 35           moltype = AA  length = 17
FEATURE                 Location/Qualifiers
source                  1..17
                        mol_type = protein
                        organism = synthetic construct
SEQUENCE: 35
YISSGSSTIY YADTVKG                                                      17

SEQ ID NO: 36           moltype = AA  length = 13
FEATURE                 Location/Qualifiers
source                  1..13
                        mol_type = protein
                        organism = synthetic construct
SEQUENCE: 36
RHYGRSRYWY FDV                                                          13

SEQ ID NO: 37           moltype = AA  length = 11
FEATURE                 Location/Qualifiers
source                  1..11
                        mol_type = protein
                        organism = Mus musculus
SEQUENCE: 37
KASQDIKSYL S                                                            11

SEQ ID NO: 38           moltype = AA  length = 7
FEATURE                 Location/Qualifiers
source                  1..7
                        mol_type = protein
```

```
                            organism = Mus musculus
SEQUENCE: 38
YATSLAD                                                                    7

SEQ ID NO: 39           moltype = AA   length = 9
FEATURE                 Location/Qualifiers
source                  1..9
                        mol_type = protein
                        organism = synthetic construct
SEQUENCE: 39
LQYGESPYT                                                                  9

SEQ ID NO: 40           moltype = AA   length = 122
FEATURE                 Location/Qualifiers
source                  1..122
                        mol_type = protein
                        organism = synthetic construct
SEQUENCE: 40
EVQLVESGGG LVQPGGSLRL SCAASGFTFS SFGMHWVRQA PGKGLEWVAY ISSGSSTIYY          60
ADTVKGRFTI SRDNPKNSLY LQMTSLRAED TAVYYCTRRH YGRSRYWYFD VWGQGTTVTV         120
SS                                                                       122

SEQ ID NO: 41           moltype = AA   length = 122
FEATURE                 Location/Qualifiers
source                  1..122
                        mol_type = protein
                        organism = synthetic construct
SEQUENCE: 41
EVQLVESGGG LVQPGGSLRL SCAASGFTFS SYSMHWVRQA PGKGLEWVSY ISSSSSTIYY          60
ADSVKGRFTI SRDNAKNSLY LQMTSLRAED TAVYYCARRH YGRSRYWYFD VWGQGTTVTV         120
SS                                                                       122

SEQ ID NO: 42           moltype = AA   length = 122
FEATURE                 Location/Qualifiers
source                  1..122
                        mol_type = protein
                        organism = synthetic construct
SEQUENCE: 42
QVQLVESGGG LVKPGGSLRL SCAASGFTFS SFGMHWIRQA PGKGLEWVAY ISSGSSTIYY          60
ADTVKGRFTI SRDNPKNSLY LQMTSLRAED TAVYYCTRRH YGRSRYWYFD VWGQGTTVTV         120
SS                                                                       122

SEQ ID NO: 43           moltype = AA   length = 122
FEATURE                 Location/Qualifiers
source                  1..122
                        mol_type = protein
                        organism = synthetic construct
SEQUENCE: 43
QVQLVESGGG LVKPGGSLRL SCAASGFTFS SYGMHWIRQA PGKGLEWVSY ISSSGSTIYY          60
ADSVKGRFTI SRDNAKNSLY LQMTSLRAED TAVYYCARRH YGRSRYWYFD VWGQGTTVTV         120
SS                                                                       122

SEQ ID NO: 44           moltype = AA   length = 122
FEATURE                 Location/Qualifiers
source                  1..122
                        mol_type = protein
                        organism = synthetic construct
SEQUENCE: 44
QVQLVESGGG LVKPGGSLRL SCAASGFTFS SYYMSWIRQA PGKGLEWVSY ISSSGSTIYY          60
ADSVKGRFTI SRDNAKNSLY LQMTSLRAED TAVYYCARRH YGRSRYWYFD VWGQGTTVTV         120
SS                                                                       122

SEQ ID NO: 45           moltype = AA   length = 122
FEATURE                 Location/Qualifiers
source                  1..122
                        mol_type = protein
                        organism = synthetic construct
SEQUENCE: 45
QVQLVESGGG VVQPGRSLRL SCAASGFTFS SFGMHWVRQA PGKGLEWVAY ISSGSSTIYY          60
ADTVKGRFTI SRDNPKNTLY LQMTSLRAED TAVYYCTRRH YGRSRYWYFD VWGQGTTVTV         120
SS                                                                       122

SEQ ID NO: 46           moltype = AA   length = 122
FEATURE                 Location/Qualifiers
source                  1..122
                        mol_type = protein
                        organism = synthetic construct
SEQUENCE: 46
QVQLVESGGG VVQPGRSLRL SCAASGFTFS SYAMHWVRQA PGKGLEWVAY ISSGGSTIYY          60
```

```
ADSVKGRFTI SRDNSKNTLY LQMTSLRAED TAVYYCARRH YGRSRYWYFD VWGQGTTVTV    120
SS                                                                 122

SEQ ID NO: 47            moltype = AA  length = 122
FEATURE                  Location/Qualifiers
source                   1..122
                         mol_type = protein
                         organism = synthetic construct
SEQUENCE: 47
QVQLVESGGG VVQPGRSLRL SCAASGFTFS SYAMHWVRQA PGKGLEWVAV ISYGGSTKYY    60
ADSVKGRFTI SRDNSKNTLY LQMTSLRAED TAVYYCARRH YGRSRYWYFD VWGQGTTVTV    120
SS                                                                 122

SEQ ID NO: 48            moltype = AA  length = 107
FEATURE                  Location/Qualifiers
source                   1..107
                         mol_type = protein
                         organism = synthetic construct
SEQUENCE: 48
EIQMTQSPST LSASVGERVT ITCRASQDIK SYLSWYQQKP GKAPKTLIYY ATSLADGVPS    60
RFSGSGSGQE YTLTISSLQP EDFATYYCLQ YGESPYTFGQ GTKLEIK                 107

SEQ ID NO: 49            moltype = AA  length = 107
FEATURE                  Location/Qualifiers
source                   1..107
                         mol_type = protein
                         organism = synthetic construct
SEQUENCE: 49
EIQMTQSPST LSASVGERVT ITCRASQDIK SYLAWYQQKP GKAPKLLIYY ASSLASGVPS    60
RFSGSGSGTE FTLTISSLQP EDFATYYCLQ YGESSYTFGQ GTKLEIK                 107

SEQ ID NO: 50            moltype = AA  length = 107
FEATURE                  Location/Qualifiers
source                   1..107
                         mol_type = protein
                         organism = synthetic construct
SEQUENCE: 50
EIQMTQSPST LSASVGERVT ITCRASQSIS SYLAWYQQKP GKAPKLLIYY ASSLESGVPS    60
RFSGSGSGTE FTLTISSLQP EDFATYYCQQ YGESSYTFGQ GTKLEIK                 107

SEQ ID NO: 51            moltype = AA  length = 107
FEATURE                  Location/Qualifiers
source                   1..107
                         mol_type = protein
                         organism = synthetic construct
SEQUENCE: 51
EIVMTQSPGT LSLSPGERAT LSCRASQDIK SYLSWYQQKP GQAPRTLIYY ATSLADGIPS    60
RFSGSGSGQE YTLTISRLEP EDFAVYYCLQ YGESPYTFGQ GTKLEIK                 107

SEQ ID NO: 52            moltype = AA  length = 107
FEATURE                  Location/Qualifiers
source                   1..107
                         mol_type = protein
                         organism = synthetic construct
SEQUENCE: 52
EIVLTQSPGT LSLSPGERAT LSCRASQDVK SYLAWYQQKP GQAPRLLIYY ASSRATGIPS    60
RFSGSGSGTE FTLTISRLEP EDFAVYYCLQ YGESPYTFGQ GTKLEIK                 107

SEQ ID NO: 53            moltype = AA  length = 107
FEATURE                  Location/Qualifiers
source                   1..107
                         mol_type = protein
                         organism = synthetic construct
SEQUENCE: 53
EIVLTQSPGT LSLSPGERAT LSCRASQSVS SYLAWYQQKP GQAPRLLIYG ASSRATGIPS    60
RFSGSGSGTE FTLTISRLEP EDFAVYYCQQ YGESPYTFGQ GTKLEIK                 107

SEQ ID NO: 54            moltype = AA  length = 24
FEATURE                  Location/Qualifiers
source                   1..24
                         mol_type = protein
                         organism = synthetic construct
SEQUENCE: 54
EGNKPVLFQG NTNPTDVVVA VFPK                                          24
```

```
SEQ ID NO: 55          moltype = AA   length = 19
FEATURE                Location/Qualifiers
source                 1..19
                       mol_type = protein
                       organism = synthetic construct
SEQUENCE: 55
EGNKPVLFQG NTNPTDVVC                                              19
```